United States Patent
Wilson et al.

(10) Patent No.: US 10,260,065 B2
(45) Date of Patent: Apr. 16, 2019

(54) RANDOM RNA LIBRARIES, METHODS OF GENERATING SAME, AND SCREENING METHODS UTILIZING SAME

(71) Applicant: THE TRUSTEES OF THE UNIVERSITY OF PENNSYLVANIA, Philadelphia, PA (US)

(72) Inventors: Robert B. Wilson, Wynnewood, PA (US); Yongping Wang, Wynnewood, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 406 days.

(21) Appl. No.: 14/910,369

(22) PCT Filed: Aug. 5, 2014

(86) PCT No.: PCT/US2014/049672
§ 371 (c)(1),
(2) Date: Feb. 5, 2016

(87) PCT Pub. No.: WO2015/020990
PCT Pub. Date: Feb. 12, 2015

(65) Prior Publication Data
US 2016/0177294 A1 Jun. 23, 2016

Related U.S. Application Data

(60) Provisional application No. 61/862,241, filed on Aug. 5, 2013.

(51) Int. Cl.
*C12N 15/10* (2006.01)
*C12N 15/66* (2006.01)

(52) U.S. Cl.
CPC ......... *C12N 15/1068* (2013.01); *C12N 15/10* (2013.01); *C12N 15/1058* (2013.01); *C12N 15/1093* (2013.01); *C12N 15/66* (2013.01)

(58) Field of Classification Search
CPC .................. C12N 15/1068; C12N 15/1058; C12N 15/10; C12N 15/1093; C12N 15/66
See application file for complete search history.

(56) References Cited

U.S. PATENT DOCUMENTS

| 2004/0152172 A1 | 8/2004 | Geppert et al. |
| 2009/0285788 A1* | 11/2009 | Wilson ............... C12N 15/1086 424/93.21 |
| 2012/0258892 A1 | 10/2012 | Wang et al. |

FOREIGN PATENT DOCUMENTS

| CN | 102925987 | 2/2013 |
| WO | WO 2007/103365 | 9/2007 |

OTHER PUBLICATIONS

Wu et al. (PLoS ONE, 2011, 6:12 e28580) (Year: 2011).*

(Continued)

*Primary Examiner* — Jeremy C Flinders
(74) *Attorney, Agent, or Firm* — Pearl Cohen Zedek Latzer Baratz LLP; Mark S. Cohen

(57) ABSTRACT

This invention provides sets and libraries of short hairpin ribonucleic acid (shRNA) molecules comprising a double-stranded region of random sequence containing random mismatches, methods of generating same, sets and libraries of expression vectors for same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

28 Claims, 15 Drawing Sheets

Specification includes a Sequence Listing.

(56) References Cited

OTHER PUBLICATIONS

Wang et al., "A random shRNA-encoding library for phenotypic selection and hit-optimization", PLoS ONE 3: e3171, 2008.
Tindall and Kunkel "Fidelity of DNA synthesis by the Thermus aquaticus DNA polymerase", Biochemistry 27:6008-13, 1988.
Goodman et al., "Error-prone repair DNA polymerases in prokaryotes and eukaryotes", Annu. Rev. Biochem. 71:17-50, 2002.
Ohmori et al., "The Y-family of DNA polymerases", Mol. Cell. 8:7-8, 2001.
Enright et al., "MicroRNA targets in *Drosophila*", Genome Biol 2003;5(1):R1).
Megraw et al., "miRGen: a database for the study of animal microRNA genomic organization and function", (2006). Nucleic Acids Res, 35: D149-D155.
Lewis et al., "Conserved seed pairing, often flanked by adenosines, indicates that thousands of human genes are microRNA targets", Cell, 120:15-16 (2005).
Lim et al., "The microRNAs of Caenorhabditis elegans", 2003, Genes & Dev. 17, 991.
Krek et al, "Combinatorial microRNA target predictions", Nature Genetics 37:495-500 (2005).
Rusinov et al., "MicroInspector: a web tool for detection of miRNA binding sites in an RNA sequence", Nucleic Acids Res 2005;33: W696-700.
Palliser et al., "An siRNA-based microbicide protects mice from lethal herpes simplex virus 2 infection", Nature. Jan. 5, 2006;439(7072):89-94.
Banan M et al (The ins and outs of RNAi in mammalian cells. Curr Pharm Biotechnol. Oct. 2004;5(5):441-50.
Wadhwa R et al (Vectors for RNA interference. Curr Opin Mol Ther. Aug. 2004;6(4):367-72).
Griffiths-Jones S, Grocock RJ, van Dongen S, Bateman A, Enright AJ. Nucl Acids Res, 2006, 34: D140-D144.
Griffiths-Jones S (Nucl Acids Res, 2004, 32: D109-D111.
Jaronczyk K et al (Exploring the functions of RNA interference pathway proteins: some functions are more RISCy than others. Biochem J. May 1, 2005;387(Pt 3):561-71.
Chambers et al (Functional expression cloning of Nanog, a pluripotency sustaining factor in embryonic stem (ES) cells. Cell 113, 643-55 (2003).
Lehtovaara et. al. ((1988) *Protein Eng* 2: 63-68 )(Materials and Methods, Figure 13A.

* cited by examiner

Strategy II, Part I
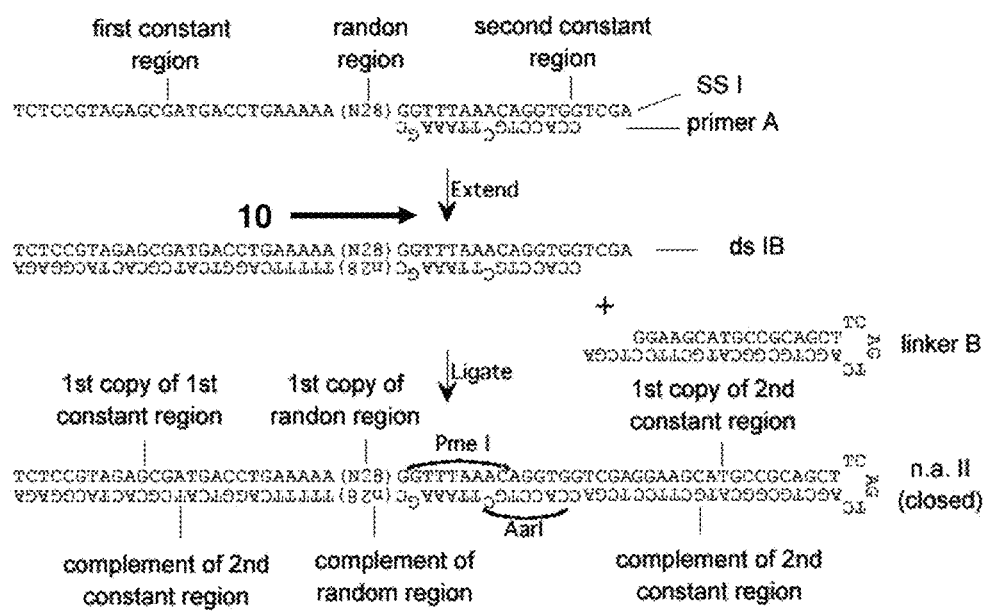
FIGURE 3
Continued on Figure 4

A

B

Hits from the 3M mismatch library

| | | |
|---|---|---|
| 3 | CGTAGGTTACTGGGCACAATGGTCATACGG CTAAAC | (SEQ ID No: 164) |
| | GCATTCAATGACCCGTGTTACCAGGGTGC- | (SEQ ID No: 156) |
| 6 | AGGCATCGATTTATAAGGCATACAGCCAG CTAAAC | (SEQ ID No: 165) |
| | TCCGCAGCTAAATATTCCGTCTGCCGGTC | (SEQ ID No: 157) |
| 10 | TAGAAGGTTGATATATGAGTTAGGGTATG CTAAAC | (SEQ ID No: 166) |
| | GTCTTCCAACTATGTACTCGGTCCCATAC | (SEQ ID No: 158) |

Hits from the 300K non-mismatch library

| | | |
|---|---|---|
| 1p | GGGTAGCTACATTTGCATATGTGGATATG CTAAAC | (SEQ ID No: 167) |
| | CCCATCGATGTAAACGTATACACCTATAC | (SEQ ID No: 159) |
| 3p | GTGGATCAGTGTGTTATAGCTCGGGCAGG CTAAAC | (SEQ ID No: 168) |
| | CACCTAGTCACACAATATCGAGCCCGTCC | (SEQ ID No: 160) |
| 5 | GGTAGAGGGGATGTCAAACTTGATTGATG CTAAAC | (SEQ ID No: 169) |
| | CCATCTCCCCTACAGTTTGAACTAACTAC | (SEQ ID No: 170) |

Fig. 15C

RANDOM RNA LIBRARIES, METHODS OF GENERATING SAME, AND SCREENING METHODS UTILIZING SAME

CROSS-REFERENCE TO RELATED APPLICATIONS

This application is a National Phase Application of PCT International Application No. PCT/US14/49672, International Filing Date Aug. 5, 2014, claiming priority of U.S. Provisional Patent Application No. 61/862,241, filed Aug. 5, 2013, which is/are hereby incorporated by reference.

GOVERNMENT INTEREST STATEMENT

This invention was made with government support under Grant Number 5R01-GM090304 and K08-DK-085152, both awarded by the National Institutes of Health. The government has certain rights in the invention.

FIELD OF INVENTION

This invention provides expression vectors for a short hairpin ribonucleic acid (shRNA) molecule comprising a double-stranded region of random sequence containing random mismatches, sets and libraries of same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

BACKGROUND OF THE INVENTION

Libraries of random, inhibitory hairpin RNA and methods for constructing such libraries have important applications in identifying therapeutic RNA molecules and RNA molecules with biological activity; but the libraries have been extremely difficult to synthesize because of the limitations of conventional procedures for randomization and generation of RNA libraries. Applicants have provided the foregoing as described in U.S. Published Application No. 2009-0285788, which is hereby incorporated by reference in its entirety. Random mutagenesis on hit sequences from one of the foregoing libraries to improve them, and an improved sequence had a key mismatch, and it was shown that that mismatch per se contributed to potency (Wang et al., PLoS ONE 3: e3171, 2008). In addition, endogenous miRNAs almost invariably have mismatches. There exists a further long-standing need in the art for methods of constructing random, inhibitory hairpin RNA libraries where the random duplex RNA itself contains random mismatches. Such libraries have important applications in identifying therapeutic RNA molecules and RNA molecules with biological activity, but are even more difficult to synthesize because of the limitations of conventional procedures for their generation.

SUMMARY OF THE INVENTION

Provided herein are expression vectors for a short hairpin ribonucleic acid (shRNA) molecule comprising a double-stranded region of random sequence containing random mismatches, sets and libraries of same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

In one aspect, provided here are sets or libraries of recombinant expression vectors, wherein a set or library of recombinant expression vectors expresses a set or library of short hairpin ribonucleic acid (shRNA) molecules. Individual shRNA molecules of the set or library of shRNA molecules comprise contiguously: (a) a variable region consisting of a sequence, wherein said sequence is either (I) substantially random; or (II) comprises a first sub-region and a second sub-region, wherein said first sub-region is substantially random and said second sub-region has a first sequence common to said set or library of shRNA molecules; (b) a non self-complementary region, preferably consisting of a second sequence common to said library; and (c) a complementary region consisting of a sequence, wherein said sequence is the reverse complement of the variable region except for containing at least one mismatch in at least 10% of the shRNA molecules. Thus, the set or library of shRNA molecules includes individual shRNA molecules where the variable region and the complementary region can form a double-stranded secondary structure (also referred to herein as "ds region") of random sequence containing one or more random mismatched basepairs.

In another aspect, provided herein are methods of generating a set or library of recombinant expression vectors, wherein the set or library of recombinant expression vectors is capable of expressing a set or library of shRNA molecules, the methods comprising the steps of:

a. providing a nucleic acid intermediate I, wherein said single-stranded nucleic acid intermediate I comprises:
  (i) a first constant region;
  (ii) a variable region consisting of a sequence, wherein said sequence is either (I) substantially random; or (II) comprises a first sub-region and a second sub-region, wherein said first sub-region is substantially random and said second sub-region has a first sequence common to said set or library of shRNA molecules; and
  (iii) a second constant region;

b. annealing a first primer to said second constant region of said single-stranded nucleic acid intermediate I;

c. obtaining double-stranded intermediates I B for each of the four nucleotides (A, C, T and G) by extending said primer hybridized to nucleic acid intermediate I with the following polymerization reaction:
  (i) using a high-fidelity polymerase to extend said first primer in the absence of one of the four nucleotides;
  (ii) using a low-fidelity polymerase to continue the polymerization reaction in the absence of one of the four nucleotides;
  (iii) using a high-fidelity polymerase to continue the polymerization reaction in the presence of all four nucleotides;
  thereby obtaining double-stranded intermediates I B from said single-stranded nucleic acid intermediate I, said double-stranded intermediate I B comprising said single-stranded nucleic acid intermediate I and an additional single-stranded nucleic acid molecule, wherein said additional single-stranded nucleic acid molecule hybridizes with said single-stranded nucleic acid intermediate I;

d. obtaining nucleic acid intermediates II from said double-stranded intermediates I B, and wherein said nucleic acid intermediates II comprise:

(i) said single-stranded nucleic acid intermediate I;
(ii) an intervening region; and
(iii) a region that hybridizes with said single-stranded nucleic acid intermediate I;
e. obtaining double-stranded intermediates III from nucleic acid intermediates II, comprising said nucleic acid intermediate II and an additional nucleic acid molecule that hybridizes with said nucleic acid intermediate II, and wherein said double-stranded intermediates III comprise:
(i) a first, double-stranded copy of said first constant region or a fragment thereof;
(ii) a first, double-stranded copy of said variable region;
(iii) a first, double-stranded copy of said second constant region;
(iv) a double-stranded copy of said intervening region;
(v) a second, inverted double-stranded copy of said second constant region;
(vi) a second, inverted double-stranded copy of said variable region; and
(vii) a second, inverted double-stranded copy of said first constant region or a fragment thereof;
wherein when said first, double-stranded copy of said variable region and said second, inverted double-stranded copy of said variable region from one strand of double-stranded intermediates III are hybridized a region of double-stranded secondary structure is formed where at least 10% contain at least one mismatched basepair; and wherein said first, double-stranded copy of said second constant region and said second, inverted double-stranded copy of said second constant region have a restriction enzyme site asymmetry, such that
(A) said first, double-stranded copy of said second constant region, but not said second, inverted double-stranded copy of said second constant region, is a substrate for a first restriction enzyme, and;
(B) said second, inverted, double-stranded copy of said second constant region, but not said first double-stranded copy of said second constant region, is a substrate for a second restriction enzyme;
thereby generating a set or library of recombinant expression vectors, wherein said set or library of recombinant expression vectors is capable of expressing a set or library of shRNA molecules.

In a further aspect, provided herein are sets or libraries of recombinant viruses, the recombinant viruses generate shRNA molecules comprising a region of random sequence with double-stranded secondary structure containing one or more random mismatched basepairs. The set or library of recombinant viruses may be generated by a method according to embodiments of the present invention.

In still another aspect, provided herein are expression vectors for shRNA molecules comprising a double-stranded region of random sequence containing one or more random mismatched basepairs, wherein the shRNA molecules have an ability to affect a biological parameter of interest. The expression vector may be identified by a method according to embodiments of the present invention.

In an additional aspect, provided herein are methods of conferring upon a cell a protection against a viral infection, the methods comprising: contacting the cell with an expression vector or RNA molecule according to embodiments of the present invention.

In yet another aspect, provided herein are methods of inhibiting or impeding an ability of a virus to replicate in a subject, the methods comprising: contacting the subject with an expression vector according to embodiments of the present invention.

In yet a further aspect, provided herein are methods of inducing a differentiation of a cell into a cell type of interest, the methods comprising: contacting the cell with an expression vector or RNA molecule according to embodiments of the present invention.

In yet an additional aspect, provided herein are methods of inducing a long-term proliferation or sustaining a pluripotency of a cell, the methods comprising: contacting the cell with an expression vector or RNA molecule according to embodiments of the present invention.

In still an additional aspect, provided herein are sets or libraries of expression vectors, wherein the expression vectors generate shRNA molecules comprising a double-stranded region of random sequence containing one or more random mismatched basepairs, and wherein the set or library of expression vectors is generated by a method according to embodiments of the present invention.

In still a further aspect, provided herein are expression vectors for shRNA molecules comprising a double-stranded region of random sequence containing one or more random mismatched basepairs, wherein the expression vectors are identified by a method according to embodiments of the present invention.

In yet still another aspect, provided herein are shRNA molecules that are encoded by expression vectors according to embodiments of the present invention.

In yet still a further aspect, provided herein are RNA molecules comprising a double-stranded region of random sequence containing one or more random mismatched basepairs, wherein the RNA molecules are identified by a method according to embodiments of the present invention.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3. Additional strategy (Strategy II) for creation of a library of expression vectors for partially self-complementary RNA molecules, part I. Described in Example 4. Sequences of 10 or more nt and not previously assigned a SEQ ID No are listed as SEQ ID No: 13-17.

Figure 1:
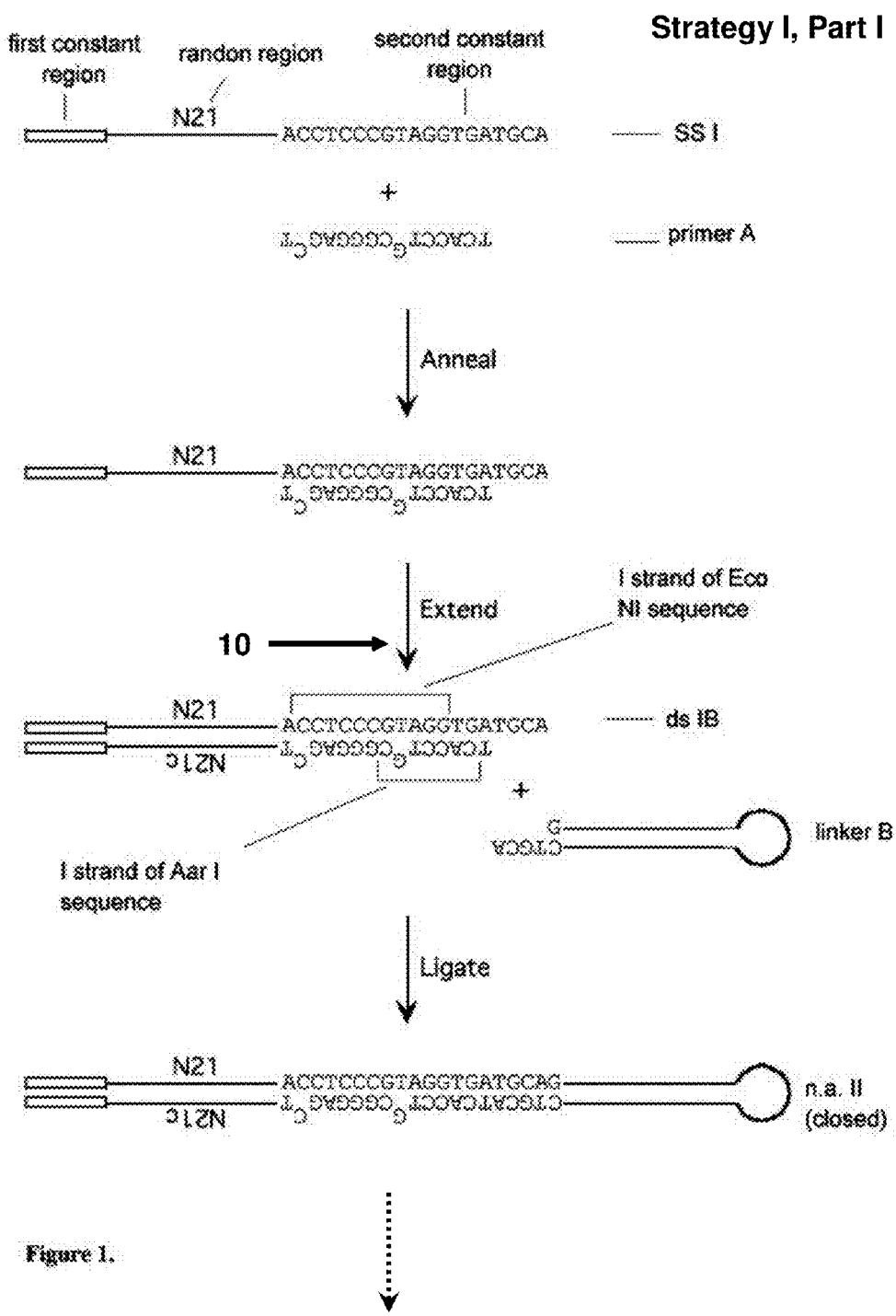
FIG. 1: Strategy (Strategy I) for creation of a library of expression vectors for partially self-complementary RNA molecules, part I. Described in Example 3. Sequences of 10 or more nt are listed as SEQ ID No: 3-6.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

Provided herein are expression vectors for a short hairpin ribonucleic acid (shRNA) molecule comprising a double-stranded region of random sequence containing random mismatches, sets and libraries of same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

In one aspect, provided here are sets or libraries of recombinant expression vectors, wherein a set or library of recombinant expression vectors expresses a set or library of short hairpin ribonucleic acid (shRNA) molecules. Individual shRNA molecules of the set or library of shRNA molecules comprise contiguously: (a) a variable region consisting of a sequence, wherein said sequence is either (I) substantially random; or (II) comprises a first sub-region and a second sub-region, wherein said first sub-region is substantially random and said second sub-region has a first sequence common to said set or library of shRNA molecules; (b) a non self-complementary region, preferably consisting of a second sequence common to said library; and (c) a complementary region consisting of a sequence, wherein said sequence is the reverse complement of the variable region except for containing at least one mismatch in at least 10% of the shRNA molecules. Thus, the set or library of shRNA molecules includes individual shRNA molecules where the variable region and the complementary region can form a double-stranded secondary structure (also referred to herein as "ds region") of random sequence containing one or more random mismatched basepairs.

In some embodiments, the sequences of the variable regions are generated by adding a mixture of nucleotides to an oligonucleotide synthesizer. In some embodiments, the sequences are computer-generated.

In some embodiments, the variable region of the shRNA molecules is substantially random sequence throughout its length. In some embodiments, the variable region comprises a first sub-region and a second sub-region, where the first sub-region is substantially random and the second sub-region has a sequence common to said set or library of shRNA molecules.

The length of the sub-region of substantially random sequence may be 6, 7, 8, 9, 10, 11, 12, 13, 14, 15, 16, 17, 18, 19, 20, 21, 22, 23, 24, 25, 26, 27, 28, or 29 nucleotides (nt) long. Additionally, the length of this substantially random sub-region may range in length between 6-29 nt, 7-29 nt, 8-29 nt, 10-29 nt, 11-29 nt, 12-29 nt, 13-29 nt, 14-29 nt, 15-29 nt, 7-25 nt, 8-25 nt, 9-25 nt, 10-25 nt, 11-25 nt, 12-25 nt, 13-25 nt, 14-25 nt, 15-25 nt, 7-21 nt, 8-21 nt, 9-21 nt, 10-21 nt, 11-21 nt, 12-21 nt, 13-21 nt, 14-21 nt, 15-21 nt, 7-19 nt, 8-19 nt, 9-19 nt, 10-19 nt, 11-19 nt, 12-19 nt, 13-19 nt, 14-19 nt, 15-19 nt, 7-17 nt, 8-17 nt, 9-17 nt, 10-17 nt, 11-17 nt, 12-17 nt, 13-17 nt, 14-17 nt, 7-15 nt, 8-15 nt, 9-15 nt, 10-15 nt, 11-15 nt, 7-13 nt, 8-13 nt, 9-13 nt, 10-13 nt.

In some embodiments, the number of mismatches is one. In some embodiments, the number of mismatches is two. In some embodiments, the number of mismatches is three. In some embodiments, the number of mismatches is four. In some embodiments, the number of mismatches is five. In some embodiments, the number of mismatches is six. In some embodiments, the number of mismatches is seven. In some embodiments, the number of mismatches is at least two. In some embodiments, the number of mismatches is at least three. In some embodiments, the number of mismatches is at least four. In some embodiments, the number of mismatches is at least five. In some embodiments, the number of mismatches is at least six. In some embodiments, the number of mismatches is at least seven. In some embodiments, the number of mismatches is more than seven.

At least 10% of the set or library of shRNA molecules contains mismatches. In some embodiments, at least 20%, at least 25%, at least 30%, at least 40%, at least 50%, at least 55%, at least 60%, at least 65%, at least 70%, at least 75%, at least 80%, at least 85%, at least 90%, at least 95%, at least 98%, or even approximately 100% of the set or library of shRNA molecules contains mismatches. In some embodiments, at most 50%, at most 55%, at most 60%, at most 65%, at most 70%, at most 75%, at most 80%, at most 85%, at most 90%, at most 95%, at most 98%, or even approximately 100% of the set or library of shRNA molecules contains mismatches.

The term "substantially random" or "random" as used herein refers to a sequence constructed by a random process, e.g., use of pools of mixed nt in an oligonucleotide synthesizer or use of low-fidelity polymerases. It will be appreciated that the term encompasses a lack of detectable sequence bias, as well as a minimal sequence bias. It will also be appreciated that the term encompasses sequence bias that results from the process or conditions used. For example, when using a low-fidelity polymerase with the nucleotide G omitted, the ratio of an A/C/T with a C mismatch may be skewed because the polymerase has certain preferences for "wrongly" incorporating each of A/C/T opposite a C.

The term "non self-complementary" as used herein refers to a sequence that is not palindromic.

"Mismatches" refers to hybridized nucleic acid duplexes where the 2 strands are not 100% complementary. Lack of total homology is due, for example, to a deletion, insertion, inversion, or substitution.

As used herein, the term "substantially complementary" is used to indicate a sufficient degree of complementarity or precise pairing such that stable and specific binding occurs between a nucleic acid and a nucleic acid containing the target sequence. It is understood in the art that the sequence of a nucleic acid need not be 100% complementary to that of its target. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches.

In some embodiments, the recombinant expression vectors further comprise an RNA polymerase promoter.

In some embodiments, the recombinant expression vectors of methods and compositions according to embodiments of the present invention are capable of expressing a set or library of shRNA molecules. In some embodiments, the recombinant expression vectors are capable of expressing the set or library of shRNA molecules when a cell population is contacted with them or transduced with them.

In some embodiments, the recombinant expression vectors further comprise a gene encoding an inhibitory RNA (RNAi) molecule of known function. In some embodiments, each of the recombinant expression vectors further comprises a gene encoding an RNAi molecule of known function. In some embodiments, a majority of the set or library of recombinant expression vectors further comprises a gene encoding an RNAi molecule of known function.

The term "palindromic" as used herein refers to a single-stranded nucleic acid molecule having a sequence that is the same sequence as the reverse complement of itself. The sequence AAGGCCTT is an example of a palindrome.

In another aspect, as exemplified herein in Examples 5 and 6, provided herein are methods of generating a set or library of recombinant expression vectors, wherein the set or library of recombinant expression vectors is capable of expressing a set or library of shRNA molecules, the methods comprising the steps of:

a. providing a nucleic acid intermediate I, wherein said single-stranded nucleic acid intermediate I comprises:
   (i) a first constant region;
   (ii) a variable region consisting of a sequence, wherein said sequence is either (I) substantially random; or (II)

comprises a first sub-region and a second sub-region, wherein said first sub-region is substantially random and said second sub-region has a first sequence common to said set or library of shRNA molecules; and
(iii) a second constant region;
b. annealing a first primer to said second constant region of said single-stranded nucleic acid intermediate I;
c. obtaining double-stranded intermediates I B for each of the four nucleotides (A, C, T and G) by extending said primer hybridized to nucleic acid intermediate I with the following polymerization reaction:
  (i) using a high-fidelity polymerase to extend said first primer in the absence of one of the four nucleotides;
  (ii) using a low-fidelity polymerase to continue the polymerization reaction in the absence of one of the four nucleotides;
  (iii) using a high-fidelity polymerase to continue the polymerization reaction in the presence of all four nucleotides;
  thereby obtaining double-stranded intermediates I B from said single-stranded nucleic acid intermediate I, said double-stranded intermediate I B comprising said single-stranded nucleic acid intermediate I and an additional single-stranded nucleic acid molecule, wherein said additional single-stranded nucleic acid molecule hybridizes with said single-stranded nucleic acid intermediate I;
d. obtaining nucleic acid intermediates II from said double-stranded intermediates I B, and wherein said nucleic acid intermediates II comprise:
  (i) said single-stranded nucleic acid intermediate I;
  (ii) an intervening region; and
  (iii) a region that hybridizes with said single-stranded nucleic acid intermediate I;
e obtaining double-stranded intermediates III from nucleic acid intermediates II, comprising said nucleic acid intermediate II and an additional nucleic acid molecule that hybridizes with said nucleic acid intermediate II, and wherein said double-stranded intermediates III comprise:
  (i) a first, double-stranded copy of said first constant region or a fragment thereof;
  (ii) a first, double-stranded copy of said variable region;
  (iii) a first, double-stranded copy of said second constant region;
  (iv) a double-stranded copy of said intervening region;
  (v) a second, inverted double-stranded copy of said second constant region;
  (vi) a second, inverted double-stranded copy of said variable region; and
  (vii) a second, inverted double-stranded copy of said first constant region or a fragment thereof;
  wherein when said first, double-stranded copy of said variable region and said second, inverted double-stranded copy of said variable region from one strand of double-stranded intermediates III are hybridized a region of double-stranded secondary structure is formed where at least 10% contain at least one mismatched basepair; and wherein said first, double-stranded copy of said second constant region and said second, inverted double-stranded copy of said second constant region have a restriction enzyme site asymmetry, such that
  (A) said first, double-stranded copy of said second constant region, but not said second, inverted double-stranded copy of said second constant region, is a substrate for a first restriction enzyme, and;
  (B) said second, inverted, double-stranded copy of said second constant region, but not said first double-stranded copy of said second constant region, is a substrate for a second restriction enzyme;
thereby generating a set or library of recombinant expression vectors, wherein said set or library of recombinant expression vectors is capable of expressing a set or library of shRNA molecules. In another embodiment, the 3 components listed above of the single-stranded nucleic acid intermediate I are ordered in the single-stranded nucleic acid intermediate I in 5' to 3' order as listed. In another embodiment, the 3 components listed above of the nucleic acid intermediate II are ordered in the nucleic acid intermediate II in 5' to 3' order as listed. In another embodiment, the 7 components listed above of the double-stranded intermediate III are ordered in the double-stranded intermediate III in order as listed.

In some embodiments, each end of the double-stranded product further comprises a feature independently selected from a restriction enzyme recognition site and a sticky end. In some embodiments, the features flank the double-stranded copies of the variable region, the constant, non-palindromic region, and the complementary region. The term "end" encompasses any positions flanking the double-stranded copies of the variable region, the constant, non-palindromic region, and the complementary region. End generally refers to a position within about 10 nucleotides of the absolute end. In some instances, an end will be a position at the absolute end.

In some embodiments, the variable region of an shRNA molecule of the present invention exhibits substantially random sequence throughout its length. In some embodiments, the variable region comprises a first sub-region of substantially random sequence and a second sub-region common to said set or library of recombinant expression vectors.

In some embodiments, methods of the present invention comprise the step of opening a partial double-stranded structure of nucleic acid intermediate II, to facilitate a subsequent step.

An example, without limitation, of a first and a second restriction enzyme are PmeI and AarI, respectively (see Example 5). It will be understood to those skilled in the art that a variety of restriction enzymes are suitable for this method.

In some embodiments, a method of generating a set or library of recombinant expression vectors, wherein the set or library of recombinant expression vectors expresses a set or library of shRNA molecules, further comprises the step of: engineering a set or library of recombinant expression vectors to contain the double-stranded intermediate III or a fragment thereof, thereby generating a set or library of recombinant expression vectors, wherein the set or library of recombinant expression vectors expresses a set or library of shRNA molecules.

"Single-stranded," as used herein, refers to a nucleic acid molecule wherein all the nucleotide bases are connected to one another by covalent bonds.

The terms "first copy[/copies]," "second copy[/copies]," refer to "copy" refers to an approximate copy, which may be an identical copy, of a region, nucleotide molecule, etc. In some cases, a second copy of a sequence may contain a mismatch with respect to the first copy of the sequence. In some cases, the second copy of a sequence may contain 2 mismatches relative to the first copy In some cases, the second copy of a sequence may contain more than 1 mismatch relative to the first copy. In some cases, the second copy of a sequence may contain more than 2 mismatches relative to the first copy. In some cases, the first and second copies are at least 60% homologous to one another. In some cases, the copies are at least 70% homologous to one another. In some cases, the copies are at least 80% homologous to one another. In some cases, the copies are at least 90% homologous to one another. In some cases, the copies are 100% homologous to one another.

In some embodiments of methods and compositions of the present invention, the second, inverted double-stranded copy of the second constant region is an exact copy of the first copy of the second constant region. In some embodiments, the second, inverted double-stranded copy is an approximate copy of the first copy.

In alternative embodiments, the nucleic acid intermediates II are obtained from nucleic acid intermediate I without utilizing a double-stranded intermediate I B as described above. (e.g., by using a 2nd constant region that is hairpin shaped).

In some embodiments of methods of the present invention, the first primer contains one or more mismatched residues with respect to the second constant region. In some embodiments, the 5' end of the first primer does not align precisely with the 3' end of the single-stranded nucleic acid intermediate I.

In some embodiments, the step of obtaining the nucleic acid intermediates II from the double-stranded intermediates I B comprises ligating a linker nucleic acid molecule to the 3' end of the single-stranded nucleic acid intermediate I and the 5' end of the additional single-stranded nucleic acid molecule (i.e., the 5' end of the first primer). In some embodiments, the linker nucleic acid molecule is hairpin-shaped. In other embodiments, the linker nucleic acid molecule is not hairpin-shaped.

In some embodiments of methods of the present invention, the double-stranded intermediates I B and linker nucleic acid molecule each contain half sites of different restriction enzymes, having different consensus sequences, with blunt ends or with compatible sticky ends; thus, the properly ligated product is not a substrate for either of the enzymes, while homodimers of either the extended primer or the hairpin loop linker are cut; then size separation is used to purify properly ligated products. A sticky end was used in Examples 3-5 for convenience only and is not critical to methods of present invention.

The nucleic acid intermediates II of methods and compositions according to embodiments of the present invention have a hairpin structure. In some embodiments, the nucleic acid intermediates II have a double-stranded structure. In some embodiments, the nucleic acid intermediates II have a single-stranded structure. In some embodiments, the nucleic acid intermediates II are single stranded, but have double-stranded secondary structure (Example 5). In some embodiments, the nucleic acid intermediates II initially have a double-stranded structure, but are opened into a single-stranded structure in the course of a method according to embodiments of the present invention (Examples 3 and 4).

In some embodiments of methods and compositions of the present invention, circular intermediates IV are obtained from the double-stranded (ds) intermediates III, the circular intermediates IV comprising an expression vector backbone and, as an insert, either: (a) the ds intermediates III; or (b) a fragment of the ds intermediates III, wherein the fragment comprises the first, ds copy of the region of random sequence and the second, inverted ds copy of the region of random sequence. In some embodiments, the fragment of ds intermediates III further comprise all the sequence of ds intermediates III between the first and second ds copies of the region of random sequence. In some embodiments, the circular intermediates IV comprise (a) the first, ds copy of the region of random sequence; (b) the second, inverted ds copy of the region of random sequence; and (c) a fragment of the sequence of ds intermediate III therebetween. In some embodiments, the circular intermediates IV are obtained from the ds intermediates III by ligation.

In some embodiments of methods and compositions of the present invention, the circular intermediates IV are digested with the first restriction enzyme and the second restriction enzyme described herein, thereby generating linear intermediates V.

In some embodiments of methods and compositions of the present invention, the linear intermediates V are intra-molecularly ligated, thereby generating circular products VI. In some embodiments, the intra-molecular ligation generates an expression vector that expresses a transcript comprising the following three regions contiguously: (i) the region of random sequence of single-stranded nucleic acid intermediate I; (ii) a non-palindromic intervening region; and (iii) a region that hybridizes with the region of random sequence and contains at least one mismatch. In some embodiments, the non-palindromic intervening region is a fragment of the intervening region of nucleic acid intermediates II. In some embodiments, the non-palindromic intervening region is capable of forming a loop. In some embodiments, the 3 components listed above of the linear intermediate V are ordered in the transcript in 5' to 3' order as listed.

In some embodiments, individual shRNA molecules encoded by the set or library according to embodiments of the present invention comprise a double-stranded region of random sequence containing at least one mismatch and a loop forming region between the 2 complementary strands of the region of random sequence containing at least one mismatch.

The single-stranded nucleic acid intermediate I may be generated by programming a nucleotide synthesizer to synthesize the following: 1) the sequence of the first constant region, 2) the random region, using a mixture of nucleotides at each position, 3) and the sequence of the second constant region. However, other methods of generating a single-stranded nucleic acid intermediate I are known in the art.

In some embodiments of methods and compositions of the present invention, the nucleic acid molecules and intermediates utilized in a method of the present invention is composed of DNA or of a version of DNA with an altered backbone or base composition (e.g., a phosphorothioate bond) along part or all of its length The term "constant" as used herein refers to a region that is unchanged or invariant within a library or set of nucleic acid molecules. It is understood that the term "constant" also encompasses a region that is unchanged or invariant within a subset of a library of nucleic acid molecules. For example, the starting nucleotide molecule in the methods depicted in FIGS. 1-8 each has 2 constant regions, one 5' to the random region and one 3' to the random region. In some embodiments, the term encompasses slight variations that occur between otherwise constant regions within a library.

In some embodiments, the present invention provides methods for generating an expression vector for an shRNA molecule comprising a double-stranded region of random sequences, similar to the above methods, but wherein the double-stranded intermediates III are digested or otherwise treated to remove most of the intervening sequence between the 2 copies of the region of random sequence, prior to insertion into the expression vector backbone.

In another embodiment of the methods mentioned above, the fragment of ds intermediates III that is used to form circular intermediate IV comprise the first, ds copy of the region of random sequence and the second, inverted ds copy of the region of random sequence. In another embodiment, the fragment comprises the 5 middle parts of ds intermediates III (e.g., (ii) a first, ds copy of the region of random sequence; (iii) a first, ds copy of the second constant region; (iv) a ds copy of the intervening region; (v) a second, inverted ds copy of the second constant region; and (vi) a second, inverted ds copy of the region of random sequence). In another embodiment, the fragment comprises all 7 of the parts of ds intermediates III (e.g., (i) a first, ds copy of the first constant region or a fragment thereof; (ii) a first, ds copy of the region of random sequence; (iii) a first, ds copy of the second constant region; (iv) ads copy of the intervening region; (v) a second, inverted ds copy of the second constant region; (vi) a second, inverted ds copy of the region of random sequence; and (vii) a second, inverted ds copy of the first constant region or a fragment thereof). In another embodiment, as exemplified herein in Example 5, the fragment comprises 6 of the 7 parts of ds intermediates III (e.g., (ii) a first, ds copy of the region of random sequence; (iii) a first, ds copy of the second constant region; (iv) a ds copy of the intervening region; (v) a second, inverted ds copy of the second constant region; (vi) a second, inverted ds copy of the region of random sequence; and (vii) a fragment of a second, inverted ds copy of the first constant region.

"Hybridizes," refers to the formation of a double stranded region from a single stranded nucleic acid molecule with a target molecule under the conditions wherein the method is carried out. For example, as exemplified herein in Examples 3-6, each of the double-stranded intermediates utilized comprises a new strand that hybridizes with the previous intermediate. Depending on the context, the term refers to hybridization under stringent conditions or under moderate conditions. As used herein, the term "hybridizes under stringent conditions" refers to conditions for hybridization and washing under which a double-stranded nucleotide molecule 18 residues in length and 60% self-complementary typically remains hybridized. Preferably, a double-stranded nucleotide molecule 18 residues in length and 70% self-complementary is utilized. More preferably, a double-stranded nucleotide molecule 18 residues in length and 80% self-complementary is utilized.

In some embodiments, the first constant region of the methods mentioned above or a corresponding constant region of an analogous method of the present invention, when in double-stranded form, is a substrate for a nicking endonuclease. In some embodiments, the nicking endonuclease is a DNA nicking endonuclease (e.g., Nb.BbvC I). In some embodiments, as exemplified herein in Example 5, the step of obtaining the double-stranded intermediates III comprises contacting the nucleic acid intermediates II with the nicking endonuclease, thereby generating a 3' end suitable for use as a primer; and extending that primer. In another embodiment, the nucleic acid intermediates II are digested with the nicking endonuclease.

"Strand displacement activity" refers to an ability to displace downstream DNA encountered during synthesis.

"Highly processive" refers to a polymerase capable of continuous synthesis of long stretches of DNA under the conditions utilized. Preferably, the polymerase is capable of continuous synthesis of over 1 kilobase of DNA.

"Fidelity," when used in reference to a polymerase, refers to the accuracy of template-directed incorporation of complementary bases in a synthesized DNA strand relative to the template strand. Fidelity is measured based on the frequency of incorporation of incorrect bases in the newly-synthesized nucleic acid strand. The incorporation of incorrect bases can result in point mutations, insertions or deletions. Fidelity can be calculated according to the procedures described in Tindall and Kunkel (Biochemistry 27:6008-13, 1988). Methods for determining fidelity are well known in the art. A polymerase can exhibit high fidelity or low fidelity. As used herein, the term "high fidelity" is intended to mean a frequency of accurate base incorporation that exceeds a predetermined value. Similarly, the term "low fidelity" is intended to mean a frequency of accurate base incorporation that is lower than a predetermined value. The predetermined value can be, for example, a desired frequency of accurate base incorporation or the fidelity of a known polymerase. It has been suggested that a significant proportion of mutations arise when damaged genomic DNA is replicated in an error-prone manner by one or more low-fidelity polymerases (Goodman et al., Annu. Rev. Biochem. 71:17-50, 2002). These polymerases appear to have evolved to specifically facilitate replication of a wide variety of DNA lesions that might otherwise block the high fidelity replication machinery. Most of these specialized polymerases are phylogenetically related to each other and have been collectively termed "Y-family" polymerases (Ohmori et al., Mol. Cell. 8:7-8, 2001).

Examples of polymerases that has a strand displacement activity that are suitable for use according to embodiments of the present invention include, but are not limited to, the DNA polymerases phi29, Bst, Vent (e.g., exo-), 9 oNm. In some embodiments, the polymerase is a highly processive polymerase. In some embodiments, a DNA polymerase that can perform strand displacement replication in the presence of a strand displacement factor is suitable for use in the method, even if the DNA polymerase does not perform strand displacement replication in the absence of such a factor.

In some embodiments, the nicking endonuclease utilized in methods and compositions of the present invention is Nb.Bsm I. In some embodiments, the nicking endonuclease is Nt.Alw I. In some embodiments, the nicking endonuclease is Nt.BbvC I. In some embodiments, the nicking endonuclease is Nt.BstNB I. In some embodiments, the nicking endonuclease is Nb.BsrDI. In some embodiments, the nicking endonuclease is Nb.BtsI.

In some embodiments, as exemplified herein in Examples 3-5, the 5' end of a primer used in methods and compositions of the present invention does not align precisely with the 3' end of its target nucleic acid molecule. In some embodiments, this intentional mis-alignment generates a double stranded (ds) nucleic acid molecule that contains a "sticky end" that is useful in sub-cloning. "Sticky end" refers to an end with an overhang. "Blunt end" refers to an end without an overhang.

In some embodiments, as exemplified herein in Examples 3-5, the step of obtaining the nucleic acid intermediates II of the methods of the present invention comprises ligating a linker nucleic acid molecule to the 3' end of the single-stranded nucleic acid intermediate I and the 5' end of the additional single-stranded nucleic acid molecule. In another embodiment, the linker nucleic acid molecule is hairpin-shaped. In another embodiment, the linker nucleic acid molecule is single-stranded. In another embodiment, the linker nucleic acid molecule, together with the single-stranded nucleic acid intermediate I and additional single-stranded nucleic acid molecule, forms a larger hairpin-shaped structure.

In other embodiments, if homo-dimers of the hairpin-loop linker anneal inter-molecularly and extend, this occurrence is minimized by pre-heating them to melting temperature, cooling them, and then bringing them up to ligation temperature.

In some embodiments, as exemplified herein in Example 3, the step of obtaining the ds intermediates III of the methods of the present invention comprises annealing a second primer to the nucleic acid intermediates II and extending the second primer, thereby synthesizing a third single-stranded nucleic acid molecule. In some embodiments, the step of extending is performed with a strand displacing polymerase In some embodiments, the second primer contains one or more mismatches with respect to nucleic acid intermediates II. In some embodiments, the mismatch(es) creates a restriction enzyme site asymmetry between nucleic acid intermediates II and the third ss nucleic acid molecule.

As an example of restriction site asymmetry, the circular intermediate IV has a restriction site asymmetry, such that the first copy of the second constant region is a substrate for Aar I (but not Pme I), and the second copy of the second constant region is a substrate for Pme I (but not Aar I). In this case, the asymmetry was created by the mismatched first primer used to generate ss I B. It will be understood to those skilled in the art that a variety of restriction enzymes are suitable for this method.

In some embodiments of methods and compositions of the present invention, restriction enzyme site asymmetry is generated by incorporating a mismatched residue(s) between 2 otherwise complementary nucleotide molecules utilized in methods and compositions of the present invention, in a region that will correspond to a recognition site or a cutting site of a restriction enzyme, such that the product of subsequently copying each strand has an asymmetric sequence. For example, a mismatched residue(s) is incorporated between the ss nucleic acid intermediate I and it complementary strand. Consequently, in ds intermediates III, the first, double-stranded copy of the second constant region has a different sequence from the second, inverted double-stranded copy of the second constant region.

In some embodiments of methods and compositions of the present invention, restriction enzyme site asymmetry is generated by incorporating a residue with an altered backbone or base composition into a nucleotide molecule of the present invention, in a region that will correspond to a recognition site or a cutting site of a restriction enzyme. An example of an altered backbone is the phosphorothioate linkages of single-stranded nucleic acid intermediate I. It will be understood to those skilled in the art that a variety of types of altered backbones are suitable for this method.

In some embodiments, a residue with an altered backbone or base composition is incorporated into ss nucleic acid intermediate I. In some embodiments, a residue with an altered backbone or base composition is incorporated into the complement of ss nucleic acid intermediate I. Consequently, in ds intermediates III, either (i) the first, double-stranded copy of the second constant region or (ii) the second, inverted double-stranded copy of the second constant region comprises the residue with an altered backbone or base composition. In some embodiments, 1 bond of the backbone is altered. In another embodiment, 2 bonds of the backbone are altered. In another embodiment, more than 2 bonds of the backbone are altered.

An altered backbone utilized in methods and compositions of the present invention is, for example, a phosphorothioate backbone. In another example, the altered backbone is a methyl phosphonate linkage. An altered base is, for example, any type of modified nucleoside, nucleoside analogue, or nucleic acid modification known in the art that impedes restriction enzyme cutting.

Furthermore, restriction enzyme site asymmetry is generated by a combination of incorporation of a mismatched residue(s) and incorporation of a residue(s) with an altered backbone or base composition into a nucleotide molecule of the present invention. It will apparent to those skilled in the art that either or both methods can be used in methods of the present invention.

In some embodiments, intermediates utilized in methods and compositions of the present invention comprise an additional restriction enzyme site asymmetry between the first and second ds copies of the first constant region. In some embodiments, in the case of ds intermediates III, the first, ds copy of the first constant region or fragment thereof, but not the second, inverted ds copy of the first constant region or fragment thereof, is a substrate for a third restriction enzyme. In some embodiments, the additional restriction enzyme site asymmetry causes the second, double-stranded copy of the first constant region or fragment thereof ds intermediate III, but not the first, inverted double-stranded copy of the first constant region or fragment thereof, is a substrate for the third restriction enzyme.

Figure 4:
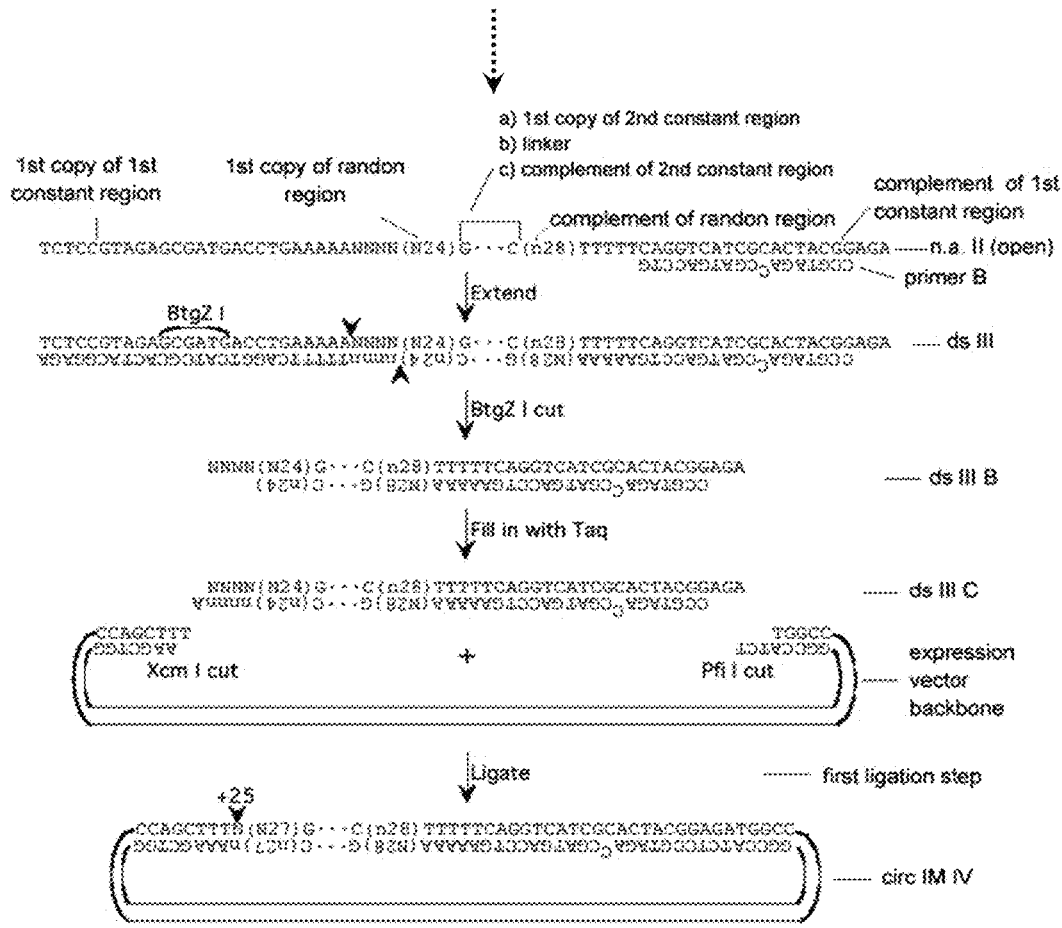
FIG. 4. Additional approach (Strategy II) for creation of a library of partially self-complementary RNA molecules, part II. Described in Example 4. Sequences of 10 or more nt and not previously assigned a SEQ ID No are listed as SEQ ID No: 18-27.

For example, as exemplified herein in Example 5, the double-stranded intermediate III (ds III) has a restriction site asymmetry, such that the first copy of the first constant region is a substrate for BtgZ I (and, initially, Not I as well), and the second copy of the first constant region is a substrate for Not I (but not BtgZ I). In this case, the BtgZ I asymmetry was created by incorporation of phosphorothioate containing residues in ss nucleic acid intermediate I. Following asymmetric digestion of ds III with BtgZ I (generating ds IIIB), the Not I site was eliminated from the first copy of the first constant region, thus allowing asymmetric digestion of ds IIIB with Not I (FIG. 7). dsIII of the method described in Example 4 has an additional restriction enzyme site asymmetry, in this case generated by a mismatch in primer B (FIG. 4).

In some embodiments, a method of the present invention further comprises contacting the double-stranded intermediates III of the methods of the present invention with the third restriction enzyme described above. In some embodiments, the step of contacting is performed prior to the step of obtaining the circular intermediates IV. In another embodiment, the double-stranded intermediates III are digested with the third restriction enzyme. In some embodiments, the step of contacting or digesting eliminates from the double-stranded intermediates III a fragment thereof or residue that is unfavorable for accurate transcription initiation from the expression vector. For example, the unfavorable fragment is a stretch of one or more consecutive purines (e.g., adenine, such as a stretch of 2, 3, 4, 5 or 6 consecutive adenines) residues. In some embodiments, the unfavorable fragment is an adenine-enriched region. In some embodiments of methods of the present invention, the promoter on the vector backbone is a promoter for transcription from the strand that formerly contained the adenine or 5 consecutive adenines. In some embodiments, the promoter in the vector initiates transcription from the strand that corresponds to the first single-stranded DNA molecule.

In some embodiments, a stretch of 5 thymidines (e.g., produced by copying the 5 adenines in the first ss DNA molecule) follows the reverse complement of the region of random sequence in the gene encoding an shRNA molecule of the present invention, allowing for termination immediately following same. In some embodiments, the stretch of thymidines immediately follows the reverse complement of the region of random sequence. Thymidine residues in the coding strand of the DNA correspond to uridine residues in the transcribed RNA; thus, in this embodiment, the RNA contains a stretch of uridine residues. In another embodiment, transcription termination after the second uridine of a uridine stretch results in a 2-nt overhang on the shRNA molecule.

In some embodiments, the additional restriction enzyme site asymmetry is generated by incorporating a residue with an altered backbone or base composition in the single-stranded nucleic acid intermediate I or the additional single-stranded nucleic acid molecule, wherein, in the double-stranded intermediates III, (i) the first, double-stranded copy of the first constant region or fragment thereof, or (ii) the second, inverted double-stranded copy of the first constant region or fragment thereof comprises the residue with an altered backbone or base composition. In another embodiment, the additional restriction enzyme site asymmetry is generated by a combination of incorporation of a mismatched residue(s) and incorporation of a residue(s) with an altered backbone or base composition into a nucleotide molecule of the present invention.

In some embodiments, expression vectors of the present invention further comprise a promoter of an RNA polymerase. In some embodiments, the expression vectors or set or library thereof are contacted with an RNA polymerase, thereby generating the shRNA molecule or set or library thereof. In some embodiments, the expression vector or set or library thereof are introduced into a population of cells, wherein it is transcribed by an endogenous RNA polymerase.

In some embodiments, an expression vector of methods and compositions of the present invention further comprises a gene encoding an RNAi molecule of known function.

In some embodiments, the set or library of the expression vectors is a set or library of recombinant viruses. In another embodiment, the set of expression vectors is packaged as a set if recombinant virus.

In some embodiments, an shRNA molecule obtained by methods and compositions of the present invention is digested, wherein the digestion generates a short hairpin RNA (shRNA) molecule. In some embodiments, the digestion occurs inside a target cell. In some embodiments, the digestion utilizes an endonuclease.

In some embodiments, the present invention provides a method for identifying an shRNA molecule that has an ability to affect a biological parameter of interest, comprising the steps of (a) contacting a cell population with a set or library of the expression vectors of the present invention, wherein the set or library of the expression vectors, or a fraction thereof, is taken up by the cell population; and (b) determining or measuring the biological parameter of interest or a readout thereof in the cell population; wherein, if a cell in the cell population exhibits an alteration of the biological parameter of interest or readout thereof, then the cell carries a particular expression vector that encodes a particular shRNA molecule that affects the biological parameter of interest.

In some embodiments of methods and compositions of the present invention, the RNA molecule functions via a known or understood mechanism of action. In some embodiments, the shRNA molecule functions via a mechanism that is understood only following discovery of the shRNA molecule. In some embodiments, the shRNA molecule functions via an unknown mechanism. In some embodiments, screening methods of the present invention do not require knowledge or understanding of the mechanism of the shRNA molecule, and thus allow function-based screening, substantially eliminating or reducing bias from the sequences screened.

In some embodiments of methods and compositions of the present invention, a particular expression vector found to have biological activity or a fragment thereof is isolated or amplified, then the vector or a fragment thereof is sequenced. In some embodiments, the fragment comprises the coding sequence for the particular shRNA molecule.

In some embodiments of methods and compositions of the present invention, an additional cell is contacted with the particular expression vector, then the biological parameter of interest or readout thereof is determined or measured in the additional cell.

In some embodiments of methods and compositions of the present invention, a copy of the particular shRNA molecule found to have biological activity is generated, an additional cell is contacted with the copy of the particular shRNA molecule, then the biological parameter of interest or readout thereof is determined or measured in the additional cell.

In some embodiments of methods and compositions of the present invention, a sequence that encodes the particular shRNA molecule found to have biological activity, or a fragment thereof, is inserted or subcloned into a second expression vector backbone, thereby generating a second expression vector, wherein the second expression vector encodes either (i) the particular shRNA molecule; or (ii) an altered version of the particular shRNA molecule. In some embodiments, an additional cell is contacted with the second expression vector, and then the biological parameter of interest or readout thereof is determined or measured in the additional cell.

In some embodiments, the altered version of the particular shRNA molecule comprises a region that shares homology with the region of random sequence containing at least one mismatch of the particular shRNA molecule. In some embodiments, the homology-sharing region of the altered version of the particular shRNA molecule is double stranded.

In some embodiments, the ds regions of the particular shRNA molecule and the altered version of same share at least 70%, at least 75%, at least 80%, at least 85%, at least 90%, at least 95%, or at least 97% homology. In some embodiments, the altered version of the particular shRNA molecule comprises a ds region that is identical with the ds region of the particular shRNA molecule. In some embodiments, the second expression vector backbone is different from the expression vector backbone utilized in the first round of screening.

In some embodiments, methods of the present invention further comprise the steps of a. isolating or amplifying a particular expression vector found to have biological activity, its insert, or a fragment thereof (the "first round of selection"); b. mutagenizing a fragment of the particular expression vector, wherein the fragment comprises a region encoding the double-stranded region of random sequence containing at least one mismatch contained in the expression vector, thereby generating a sub-library of nucleotide molecules, the nucleotide molecules comprising variants of the region of random sequence; c. inserting or subcloning the sub-library into an expression vector backbone, thereby generating a sub-library of expression vectors; d. contacting a second cell population with the sub-library of expression vectors (the "second round of selection"), wherein the sub-library of expression vectors, or a fraction thereof, is taken up by the second cell population; and e. determining or measuring the biological parameter of interest or a readout thereof in the second cell population. In this embodiment, if the biological parameter of interest or readout thereof is further altered in a particular cell in the second cell population, then the particular cell carries an improved expression vector.

In some embodiments, the step of mutagenizing comprises the step of copying a fragment of the particular expression vector by a low-fidelity method. In some embodiments, the mutagenized sequences are generated by a computer.

In some embodiments, the mutagenesis is performed using a computational method. In some embodiments, the computational method comprises generating each possible single mutation of the RNAi molecule identified. In some embodiments, double mutations are also generated. In some embodiments, triple mutations are also generated.

In some embodiments, wherein a mutation is introduced into a residue in the ds portion of the RNAi, a corresponding mutation is introduced in the complementary residue, to maintain base pairing. In another embodiment, a corresponding mutation is not introduced.

In some embodiments, the entire sequence encoding the shRNA molecule is mutagenized. In some embodiments, both strands of the double-stranded region are mutagenized. In another some embodiments, 1 strand (a "half-book") of the double-stranded region is mutagenized. In some embodiments, a portion of 1 strand of the double-stranded region is mutagenized.

In some embodiments, a method of the present invention further comprises the step of identifying 1 or more putative target mRNAs of an RNAi molecule with biological activity, and creating a sub-library of sequences predicted to bind more strongly to the targets. In some embodiments, the sub-library comprises sequences predicted to bind more strongly to 1 of the predicted targets. In some embodiments, the sub-library comprises sequences predicted to bind more strongly to a subset of the predicted targets. In some embodiments, the sub-library comprises sequences predicted to bind more strongly to most of the predicted targets. In some embodiments, the sub-library comprises sequences predicted to exhibit greater preferential binding to 1 or a subset of the predicted targets, relative to a different subset of the predicted targets. In some embodiments, binding of RNAi molecules in the sub-library to targets is tested directly in an in vitro RNAi assay.

Methods for putative target mRNAs of an RNAi molecule are well known in the art, and include, but are not limited to computer programs, such as miRanda (Enright A J, John B, Gaul U, Tuschl T, Sander C, Marks D S. MicroRNA targets in *Drosophila*. Genome Biol 2003; 5(1):R1); miRGen (M. Megraw, P. Sethupathy, B. Corda, and A. G. Hatzigeorgiou (2006). Nucleic Acids Res, 35: D149-D155); TargetScan (Lewis B P, Burge C B, Bartel D P. Cell, 120:15-16 (2005); MiRscan (Lim, L P, Lau, N C, Weinstein, E, Abdelhakim, A, Yekta, S, Rhoades, M W, Burge, C B and Bartel, D P (2003). The microRNAs of *Caenorhabditis elegans*. Genes & Dev. 17, 991); PicTar (Krek et al, Nature Genetics 37:495-500 (2005)); MicroInspector (Rusinov V, Baev V, Minkov I N, Tabler M. Nucleic Acids Res 2005; 33: W696-700).

In some embodiments, methods of present invention further comprise contacting an additional cell or cell population with a particular expression vector found to exhibit biological activity in the above methods and determining or measuring the biological parameter of interest or readout thereof in the additional cell, wherein, if the biological parameter of interest or readout thereof is altered in the additional cell, then the efficacy of the shRNA molecule encoded by the expression vector is confirmed. In some embodiments, the insert sequences are isolated from the cell population. In some embodiments, a fragment comprising the coding sequence for the shRNA molecule found to exhibit biological activity in the first round of selection is excised or amplified from the expression vector, or synthesized de novo after sequencing, subcloned into the same expression vector or a different expression vector, then used to contact an additional cell(s), for which the biological parameter of interest or readout thereof is determined or measured.

Methods for (1) modifying an shRNA molecule containing a double-stranded region, and for (2) expressing an shRNA molecule containing a double-stranded region in various types of vectors, are well known in the art, and are described, for example, in Palliser D et al (An siRNA-based microbicide protects mice from lethal herpes simplex virus 2 infection. Nature. 2006 Jan. 5; 439(7072):89-94).

In some embodiments, one or more additional rounds of enrichment are performed after the second round. In some embodiments, the use of multiple rounds of enrichment increases the fraction of true positive clones.

In some embodiments, the expression vector used in the first round of selection is an integrating vector. For example, an integrating vector facilitates identification of true positives because of the irreversible nature of its effects.

In some embodiments, a different expression vector used in the second or a subsequent round of selection and produces a different form of the RNA molecule (e.g., RNAi, siRNA, microRNA, or shRNA) identified in the first round of selection (having essentially the same double-stranded region of random sequence containing at least one mismatch), after which the different form of the RNA molecule itself (e.g., an siRNA) is brought into contact with an additional cell(s), for which the biological parameter of interest or readout thereof is determined or measured. In some embodiments, contacting the additional cell(s) with the RNA molecule itself facilitates observation of the phenotype conferred by the RNA molecule in a majority of the target cells. In some instances, the phenotype is observed in over 60%, 70%, in over 80%, in over 90%, in over 95%, in over 97%, or in over 99% of the cells in the second or subsequent round of enrichment.

In some embodiments, the different form of the RNA molecule used in the second or a subsequent round of selection exerts its effects in a reversible manner. In some embodiments, use of a reversible form of inhibitory RNA in methods of the present invention allows further study of the effects of the RNA molecule (e.g., a temporal study of its effects, or an observation of reversing or halting its effects by removing the RNA molecule). In some embodiments, an expression vector with an inducible or repressible promoter is used as an alternative to a reversible form of RNAi.

In some embodiments, only the first half of the region encoding the double-stranded region of random sequence (i.e. the region encoding one strand of the double-stranded region of random sequence; or "half-book") is placed between the first and second constant regions used for the original single-stranded DNA template and copied by a low-fidelity method, thereby generating a sub-library of half books that is used to create an shRNA-expressing sub-library by one of the methods described herein. Then the sub-library is tested for a biological parameter by a method of the present invention.

In some embodiments, the improved expression vector encodes an improved shRNA molecule that affects the biological parameter of interest more than the particular shRNA molecule originally identified. In some embodiments, the improved expression vector exhibits greater tissue specificity than the originally identified shRNA molecule. In some embodiments, a lower dosage is required of the improved expression vector or the corresponding shRNA molecule encoded thereby, than the originally identified shRNA molecule. In some embodiments, the improved expression vector exhibits any other improved property known in the art, relative to the originally identified shRNA molecule.

In some embodiments of methods and compositions of the present invention, an improved expression vector identified by the above method, its insert, or a fragment thereof is isolated or amplified. In some embodiments, either the improved expression vector is sequenced or a fragment thereof is sequenced, wherein the fragment comprises the coding sequence for the improved shRNA molecule. In some embodiments, an additional cell is contacted with the improved expression vector its encoded RNA, or another type of RNA molecule having the same or a homologous double-stranded region, and the biological parameter of interest or readout thereof is determined or measured in the additional cell.

The method of low-fidelity copying utilized in methods of the present invention is, in some embodiments, random mutagenesis by PCR (e.g., error-prone PCR). In some embodiments, the method is mutagenesis with degenerate oligonucleotides. In some embodiments, the method is linker-scanning mutagenesis.

In some embodiments, the present invention provides methods of identifying a drug target for a disease or disorder of interest, comprising the steps of (a) identifying an RNA molecule that affects a biological parameter of interest by methods of the present invention, wherein the biological parameter of interest is altered in the disease or disorder of interest; and (b) identifying a cellular RNA molecule whose expression is altered by the RNA molecule, wherein the cellular RNA molecule is identified as a drug target for the disease or disorder of interest.

In some embodiments, the present invention provides methods of identifying a variant of an RNA molecule that affects a biological parameter of interest, wherein the variant has an altered ability to affect the biological parameter of interest, comprising the steps of:
a. copying a nucleic acid molecule encoding the shRNA molecule by a low-fidelity method, thereby generating a sub-library of nucleotide molecules, the nucleotide molecules comprising variants of the shRNA molecule;
b. subcloning the sub-library into an expression vector backbone, thereby generating a sub-library of expression vectors;
c. contacting a cell population with the sub-library of expression vectors, wherein the sub-library of expression vectors, or a fraction thereof, is taken up by the cell population; and
d. determining or measuring the biological parameter of interest or a readout thereof in the cell population.

By this method, in some embodiments, if a cell in the cell population exhibits an alteration of the biological parameter of interest or readout thereof, then the cell carries a particular expression vector that encodes a particular variant of the shRNA molecule that has an altered ability to affect the biological parameter of interest.

In some embodiments, the present invention provides an altered RNA molecule that has an ability to affect a biological parameter of interest, wherein the altered RNA molecule is identified by methods of the present invention.

In some embodiments of methods of the present invention, the altered ability to affect a biological parameter of interest is altered relative to the original shRNA molecule.

As used herein, the term "altered" encompasses, depending on the specific context as will be understood to one of skill in the art, to an increased potency, a decreased potency, an increased tissue specificity, an increased biological half-life, a decreased biological half-life, an increased bioavailability and/or any other biological or therapeutic parameter of interest.

In some embodiments, a library of shRNA molecules comprising a double-stranded region of random sequence containing at least one mismatch, not inserted into an expression vector backbone, is generated by methods of the present invention. All the embodiments enumerated herein for generating a set of recombinant expression vectors apply to this method, where appropriate. The library is then used, in some embodiments, to screen for RNA molecules. In some embodiments, the present invention provides a library of shRNA molecules generated by these methods.

In some embodiments, the present invention provides an expression vector for an shRNA molecule comprising a double-stranded region of random sequence, wherein the expression vector is generated by a method of the present invention.

In some embodiments, the present invention provides an expression vector for an shRNA molecule comprising a double-stranded region of random sequence containing at least one mismatch, wherein the expression vector is identified by a method of the present invention.

In some embodiments, the present invention provides an shRNA molecule that is encoded by an expression vector of the present invention.

In some embodiments, the present invention provides an shRNA molecule that is produced by an expression vector of the present invention.

In some embodiments, the present invention provides an shRNA molecule comprising a double-stranded region of random sequence containing at least one mismatch, wherein the RNA molecule is identified by a method of the present invention.

In some embodiments, the present invention provides methods of conferring upon a cell a protection against a viral infection, comprising contacting the cell with an expression vector or RNA molecule of the present invention, thereby conferring upon a cell a protection against a viral infection. In some embodiments, the present invention provides methods of inhibiting or impeding an ability of a virus to replicate in a subject, comprising contacting the subject with an expression vector or RNA molecule of the present invention, thereby inhibiting or impeding an ability of a virus to replicate in a subject. In some embodiments, the present invention provides methods of inhibiting or impeding viral entry into a cell, comprising contacting the cell with an expression vector or RNA molecule of the present invention. In some embodiments, the expression vector or RNA molecule down-regulates a viral receptor(s) in the cell. In some embodiments, the expression vector or RNA molecule down-regulates a protein required for viral replication.

In some embodiments, the present invention provides methods of inducing a differentiation of a cell into a cell type of interest, comprising contacting the cell with an expression vector or RNA molecule of the present invention, thereby inducing a differentiation of a cell into a cell type of interest.

"Differentiation of a cell into a cell type of interest" encompasses a full differentiation or a partial differentiation. "Cell type of interest" refers, for example, to a cell type that is required for a therapeutic or research application or to an intermediate, or partially differentiated cell type that is a precursor to the cell type required for a therapeutic or research application.

In some embodiments, the present invention provides methods of inducing a long-term proliferation of a cell, comprising contacting the cell with an expression vector or RNA molecule of the present invention, thereby inducing a long-term proliferation of a cell. In some embodiments, the present invention provides methods of sustaining a pluripotency of a cell, comprising contacting the cell with an expression vector or RNA molecule of the present invention, thereby sustaining a pluripotency of a cell.

In some embodiments, methods of the present invention utilize a particular recombinant expression vector or an RNA molecule encoded thereby, wherein the particular recombinant expression vector has been selected by a method of the present invention.

In some embodiments, the present invention provides a set or library of expression vectors, wherein the expression vectors generate shRNA molecules comprising a double-stranded region of random sequence containing at least one mismatch, and wherein the set or library of expression vectors is generated by a method of the present invention.

In some embodiments, the present invention provides a set or library of recombinant viruses, wherein the recombinant viruses generate shRNA molecules comprising a double-stranded region of random sequence containing at least one mismatch, and wherein the set or library of recombinant viruses is generated by a method of the present invention.

In some embodiments, the present invention provides an expression vector for an shRNA molecule comprising a double-stranded region of random sequence containing at least one mismatch, wherein the shRNA molecule has an ability to affect a biological parameter of interest, and wherein the expression vector is identified by a method of the present invention.

In some embodiments, a method of the present invention utilizes an improved vector identified by a second screening, following generating copies of an insert of a vector or a fragment of the insert by a low-fidelity improvement method, as described herein.

The particular polymerases, restriction enzymes, restriction sites, vectors, primers, enzymes etc. utilized in the Examples herein are merely exemplary. Any suitable polymerase, restriction enzyme, restriction site, vector, primer, enzyme etc. can be utilized in accordance with the methods disclosed herein.

In some embodiments of methods of the present invention, the second and/or third recognition site described above is not derived entirely from the sequence from the first single-stranded DNA molecule, but rather takes all or part of its sequence from the hairpin-shaped DNA molecule.

In some embodiments, the present invention provides methods of generating an shRNA molecule comprising a double-stranded region of random sequence, the methods comprising the steps of:

a. obtaining a first single-stranded DNA molecule, wherein the first single-stranded DNA molecule comprises, in 5' to 3' order, (i) a first constant region, wherein the first constant region comprises a first recognition site, which, when in double-stranded form, is a substrate for a first restriction enzyme, wherein the first constant region ends in one or more adenines;

(ii) a region of random sequence; and (iii) a second constant region, wherein the second constant region comprises a second recognition site, which, when in double-stranded form, is a substrate for a second restriction enzyme;

b. annealing a first primer to the second constant region, wherein (i) the first primer contains mismatch(es) with respect to the second constant region;

(ii) the first primer, when in double-stranded form, is not a substrate for the second restriction enzyme;

(iii) the first primer, when in double-stranded form, is a substrate for a third restriction enzyme; and (iv) the second constant region, when in double-stranded form, is not a substrate for the third restriction enzyme;

c. for each of the four nucleotides (A, C, T and G), extending the first primer with the following steps:

(1) using a high-fidelity polymerase to extend said first primer in the absence of one of the four nucleotides;

(2) using a low-fidelity polymerase to continue the polymerization reaction in the absence of one of the four nucleotides;

(3) using a high-fidelity polymerase to continue the polymerization reaction in the presence of all four nucleotides;

thereby generating double-stranded intermediates I B, comprising the first single-stranded DNA molecule and a second single-stranded DNA molecule, wherein the second single-stranded DNA molecule comprises a reverse complement containing one or more mismatches of the region of random sequence and the first constant region;

d. ligating a hairpin-shaped DNA molecule to the 3' end of the first single stranded DNA molecule and the 5' end of the second single-stranded DNA molecule, thereby converting the double-stranded intermediates I B into a hairpin-shaped intermediates II;

e. annealing a second primer to the reverse complement of the first constant region, wherein:

(i) the second primer contains mismatches with respect to the reverse complement of the first constant region; and (ii) the second primer, when in double-stranded form, is not a substrate for the first restriction enzyme;

f. extending the second primer, thereby generating double-stranded intermediates III, comprising the hairpin-shaped intermediates II and a third single-stranded DNA molecule;

g. digesting the double-stranded intermediates III with the first restriction enzyme, thereby generating a double-stranded intermediates IV, wherein the double-stranded intermediates IV do not comprise the one or more adenines on its strand that corresponds to the first single-stranded DNA molecule;

h. ligating the double-stranded intermediates IV into a linearized vector backbone, wherein the linearized vector backbone comprises an RNA polymerase promoter, thereby generating circular intermediates V;

i. digesting the circular intermediates V with the second restriction enzyme and the third restriction enzyme, thereby generating linear intermediates VI; and
j. intra-molecularly ligating linear intermediates VI, thereby generating expression vectors for an shRNA molecule comprising a double-stranded region of random sequence containing at least one mismatch.

In some embodiments, the intervening sequence of partially self-complementary RNA molecules of the present invention forms a stem-loop structure when the random sequence and its complement are annealed. In some embodiments of methods of present invention, the loop-forming region is not palindromic. In some embodiments, the loop-forming region is not self-complementary.

In some embodiments, the RNA molecule expressed by a vector of the present invention is a short hairpin RNA (shRNA). In some embodiments, the RNA molecule is a small inhibitory RNA (siRNA). In some embodiments, the RNA molecule is an inhibitory RNA (RNAi). In some embodiments, the RNA molecule is an agRNA (antigenic RNA). "agRNA" refers to a double stranded RNA capable of interacting with mRNA and silencing gene transcription. In some embodiments, the RNA molecule is a microRNA (miRNA). In some embodiments, the RNA molecule is an anti-sense locked-nucleic acid (LNA) oligonucleotide. Other types of inhibitory RNA are enumerated and described in Banan M et al (The ins and outs of RNAi in mammalian cells. Curr Pharm Biotechnol. 2004 October; 5(5):441-50.

In some embodiments, the first residue of the second constant region of ss intermediate I determines the identity of the complementary nucleotide pair flanking the loop sequence in a ds RNA produced by a recombinant expression vector of the present invention. In some embodiments, a method of the present invention is repeated with 4 sets of first single-stranded DNA molecule, wherein the second constant region begins with 4 different nucleotides in the four groups. In some embodiments, the 4 pools are combined to generate a library wherein every residue of the "stem" is randomized.

In some embodiments of methods of the present invention, the mismatched residue in the first primer (or, if more than one, the mismatch closest to the 3' end) is 1 nucleotide (nt) away from the 3' end of the first primer. In some embodiments, the distance is 2 nt or less. In some embodiments, the distance is 3 nt or less. In some embodiments, the distance is 4 nt or less. In some embodiments, minimizing this distance reduces the amount of sequence in the stem of the RNA molecules that is derived from the primer (and that is therefore constant).

"Expression vector" refers to a means of expressing an RNA molecule. For example, the expression vector is a plasmid. In another example, the vector is a recombinant viral vector. In another example, the vector is a recombinant bacterial vector. In another example, the vector is a naked DNA vector. In another example, the vector is a self-replicating nucleic molecule, or virus comprising same, that is capable of expressing an RNA molecule.

Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York).

The expression vectors and shRNA molecules provided herein may be being packaged in recombinant virus (e.g., a packaging cell line). In some embodiments, a library of expression vectors, encoding shRNA molecules that contain a number of regions of random sequence, is generated by methods of the present invention. In some embodiments, the library is in retrovirus form (e.g., in the form of RNA that is reverse-transcribed upon transduction to generate the DNA form of the vector).

The expression vectors provided herein may be integrated into the genome of cells (e.g., in the cell population used to test and/or identify the vectors). In some embodiments, the expression vectors integrate into the genome of the target cells (e.g., for a therapeutic utility). In some embodiments, the expression vectors are carried in cells in the cell population episomally. In some embodiments, the expression vectors are carried in cells in the cell population as extra-chromosomal vectors. In some embodiments, a drug resistance gene or other selectable marker is used to select for cells that retain the expression vector.

The expression vectors provided herein may further comprise a gene encoding a marker protein; e.g., enhanced green fluorescent protein (eGFP) or enhanced farnesylated green fluorescent protein (eGFPf). In some embodiments, a marker protein is used to detect transfected or transduced cells in subsequent steps of methods provided herein (e.g., library screening or selection methods).

The expression vectors provided herein may further comprise a gene encoding a protein that confers a phenotype of interest. In some embodiments, the gene confers a disease phenotype. In some embodiments, the expression vector is used to identify therapeutic RNA molecules that ameliorate, alleviate, or treat the disease or disease phenotype.

The expression vectors provided herein may further comprise a gene encoding an inhibitory RNA molecule (e.g., a short-interfering (siRNA) molecule) of known function. In some embodiments, the inhibitory RNA molecule of known function is used to confer a phenotype (e.g., a phenotype of a disease of interest) on the cells that are being screened with the library. In some embodiments, an siRNA molecule added exogenously is used to confer the phenotype. In some embodiments, the library is used to identify RNA molecules that treat the phenotype or disease of interest conferred by the inhibitory RNA molecule of known function.

In some embodiments, shRNA sequences that are lost from a pool are identified using negative selection. In another embodiment, negative selection is used to identify shRNAs that are selectively toxic to cells with cancer-associated mutations, thereby improving therapeutic indices.

In some embodiments, the 2 RNAi molecules (the RNAi of known function and the RNA molecule containing a double-stranded region of random sequence containing at least one mismatch) are encoded by 2 H1-promoter cassettes. In some embodiments, the 2 H1-promoter cassettes can be independently subcloned into the vector. In some embodiments, one of the 2 H1-promoter cassettes comprises a double-stranded region of random sequence containing at least one mismatch.

In some embodiments of methods of the present invention, asymmetric digestion of a circular intermediate results in unequal portions of the first and second copies of the second constant region on the 2 ends of a linear intermediate generated thereby. In some embodiments, the unequal portions allow the loop sequence to be non-self-complementary.

The promoter of an RNA polymerase present in a linearized vector backbone may be an RNA pol III promoter. For example, the promoter is an H1 promoter or a U6 promoter. It will be appreciated that a variety of promoters are well known in the art.

The promoter in the expression vector may be 25 nt upstream of the beginning of the region of random sequence in the expression plasmid. In some cases, one or more consecutive pyrimidines (e.g., 4) immediately precedes the transcription start site in the expression plasmid. In some embodiments, the string consists of 2 pyrimidines. In some embodiments, the string consists of 4 pyrimidines. In some embodiments, the string consists of 3 pyrimidines. In some embodiments, the string consists of 5 pyrimidines.

Methods of present invention may include contacting the expression vector or set or library of expression vectors with an RNA polymerase performed in the presence of ribonucleotide precursors, thereby generating the shRNA molecule or library thereof.

In some embodiments, methods of present invention further comprise performing multiple times, with a set of random sequences, a method of generating an expression vector for an RNA molecule of the present invention, thereby generating a set or library of the expression vectors. In some embodiments, a method of present invention further comprises packaging the set or library of expression vectors as a set or library of recombinant viruses. In some embodiments, the set or library of expression vectors is a set or library of recombinant viruses.

In some embodiments, the recombinant viruses used to package the set or library of expression vectors are recombinant retroviruses. In some embodiments, the recombinant viruses are recombinant lentiviruses. In some embodiments, the recombinant viruses are recombinant adenoviruses. Other recombinant viruses are described in Wadhwa R et al (Vectors for RNA interference. Curr Opin Mol Ther. 2004 August; 6(4):367-72). Other recombinant viruses known in the art may be used as long as the virus has the ability to infect or transduce a eukaryotic cell.

In some embodiments, the biological parameter of interest or readout thereof is a derivation of a cell type with repopulating capacity from a stem cell. In some embodiments, the cell type that is derived from the stem cell is a hematopoietic stem cell. In some embodiments, the cell type that is derived from the stem cell exhibits long-term repopulating capacity. In some embodiments, the cell type that is derived is any other cell type known in the art with repopulating capacity.

In some embodiments, the biological parameter of interest or readout thereof is ability of a cell (either the cell used in the assay or a biologically relevant target cell) to survive under a defined set of adverse conditions. In some embodiments, the biological parameter of interest or readout thereof is ability of the cell to maintain growth under a defined set of conditions. In some embodiments, the conditions are not lethal to wild-type cells, but are lethal to cells that are a disease model (e.g., cells comprising a mutation or cells in which expression of a protein or enzyme has been repressed—e.g., by inhibitory RNA).

In some embodiments, the biological parameter of interest or readout thereof is susceptibility of a cell (either the cell used in the assay or a biologically relevant target cell) to a pathogen, toxin or toxic insult. In some embodiments, the toxin or toxic insult is an oxidant. In some embodiments, the toxin or toxic insult is a stress. In some embodiments, the biological parameter of interest or readout thereof is survival of the cell despite the presence of a pathogen. In some embodiments, the biological parameter of interest or readout thereof is ability of a pathogen to replicate in the cell. In some embodiments, the pathogen is an intracellular pathogen. In some embodiments, the intracellular pathogen is a virus. In some embodiments, the intracellular pathogen is an intracellular bacterium.

In some embodiments, the biological parameter of interest or readout thereof is ability to kill a cancer cell (either the cell used in the assay or a biologically relevant target cell). In some embodiments, the biological parameter of interest or readout thereof is ability to sensitize the cancer cell to a pro-apoptotic or pro-necrotic stimulus.

In some embodiments, the biological parameter of interest or readout thereof is an expression or expression level of a protein of interest. In some embodiments, the biological parameter of interest or readout thereof is an expression or expression level of an mRNA of interest.

In some embodiments, the RNA molecule that affects susceptibility to a pathogen or replication of the pathogen hybridizes with nucleic acids specific to the pathogen. In some embodiments, the RNA molecule hybridizes with cellular nucleic acids utilized by the pathogen. In some embodiments, the RNA molecule upregulates cellular defense mechanisms. In some embodiments, the RNA molecule functions via another mechanism. In some embodiments, the RNA molecule functions via an unknown mechanism.

In some embodiments, the biological parameter of interest or readout thereof is a differentiation of the cell into a cell type of interest. In some embodiments, the biological parameter of interest or readout thereof is maintenance of a cell or cell type in an undifferentiated state. In some embodiments, the biological parameter of interest or readout thereof is ability to induce long-term proliferation or sustain pluripotency of the cell. In some embodiments, the biological parameter of interest or readout thereof is maintenance of a stem cell in an undifferentiated state.

The cell type of interest includes, but is not limited to, a heart muscle cell, neuron, skeletal muscle cell, hepatocyte, skin cell, renal tubule epithelial cell, pancreatic islet cell, glomerular cell, endothelial cell, osteocyte, chondrocyte, B or T lymphocyte, neutrophil, basophil, eosinophil, monocyte, red blood cell, dendritic cell, thyroid cell, adrenal cell, megakaryocyte. In some embodiments, the cell type of interest is any other cell damaged in a disease or disorder.

"Biological parameter" refers to any measurable or observable phenotype of a cell, e.g., a morphological characteristic, differentiation state, growth rate, cell cycle characteristic, biochemical characteristic, or another phenotype.

The cell that is the target of methods of the present invention is, in some embodiments, a stem cell. In some embodiments, the cell is an embryonic stem cell. In some embodiments, the cell is a partially differentiated cell type. In some embodiments, the cell is a precursor of a cell type of interest. In some embodiments, the cell is a model for a disease phenotype. In some embodiments, the cell is an adult stem cell. In some embodiments, the cell is a tissue-specific stem cell. In some embodiments, the cell is a cell type that is susceptible to viral infection.

RNA molecules described herein may be used to convert one cell type into another cell type.

In some embodiments, differentiation into the cell type of interested is determined morphologically. In some embodiments, differentiation is determined by measuring or assaying expression of one or more marker proteins, such as tissue-specific surface marker proteins.

Methods for determining an expression of a protein of interest are well known in the art, and include, for example, Western blot and fluorescence-activated cell sorting (FACS). Methods for determining an expression of an mRNA of interest are well known in the art, and include, for example, Northern blot.

"Readout" refers to any means known in the art of determining, assessing, measuring, or observing a biological phenotype. It will be appreciated that the term includes biochemical assays, morphological observation, cell staining, cell sorting, and the like. The term also encompasses survival under a defined set of conditions.

In some embodiments, a subset or plurality of cells exhibits the alteration in the biological parameter of interest or readout thereof that is measured. In some embodiments, multiple cells exhibit the alteration in the biological parameter of interest or readout thereof that is measured. In some embodiments, the cells contain more than one particular expression vector. In some embodiments, the particular expression vectors contained in the cells, biological activity, their inserts, or fragments thereof are each isolated and/or sequenced, thus identifying more than one RNA molecule that affects the biological parameter of interest or readout thereof.

In some embodiments, methods of the present invention further comprise isolating or amplifying the particular expression vector that mediates the alteration in the biological parameter of interest. In some embodiments, the insert of the particular expression vector is isolated or amplified. In some embodiments, a fragment of the particular expression vector is isolated or amplified. In some embodiments, the expression vector, insert, or fragment is amplified by PCR. In some embodiments, methods of present invention further comprise sequencing the particular expression vector that is isolated or amplified, its insert, or a fragment thereof. In some embodiments, the fragment comprises the coding sequence for the RNA molecule identified to have biological activity (e.g., the RNA molecule that affects the biological parameter of interest).

In some embodiments, the sequencing step comprises amplifying the coding sequence for the RNA molecule with biological activity by PCR. In some embodiments, the PCR utilizes primers from sequences in the vector that flank the coding sequence for the RNA molecule of the present invention. In some embodiments, PCR can be performed on either an integrated- or non-integrated vector.

In some embodiments of methods of the present invention, after sequencing the PCR product, the ends of an aliquot of the product are digested in a PCR tube, subcloned back into the parent vector, and the shRNA construct, or a corresponding RNAi molecule with the same or a homologous double-stranded region, or a construct encoding the corresponding RNAi molecule, (and the control shRNAs) is re-added to the test cells. In this confirmatory testing, populations of cells are compared, rather than small numbers of individual survivors. This method reduces the unlikely occurrence of false positives in screening or selection methods of the present invention.

In some embodiments, a restriction enzyme utilized herein may cut its substrate outside of its recognition sequence, for example, at least 1 nt, at least 2 nt, at least 3 nt, at least 4 nt, at least 5 nt, at least 6 nt, at least 7 nt, at least 8 nt, at least 9 nt, at least 10 nt away from the end of the recognition sequence. In some embodiments, the cut is a staggered cut whose closer cut is at least one of the above distances away from the end of the recognition sequence. In some embodiments, the distance is 10/14 nt away (i.e. 10 nt on one strand, and 14 on the other). In some embodiments, the distance is 25/27 nt away. In some embodiments, the use of a restriction enzyme that cuts outside of its recognition sequence allows the removal (on one half of the DNA molecule only) of the 5 or more consecutive adenines on the 3' end of the first constant sequence. In some embodiments, the use of such an enzyme allows the removal (on one half of the DNA molecule) of a portion of the 5 or more consecutive adenines.

In some embodiments, methods of the present invention allow for the identification of a therapeutic RNA molecule that targets more than one gene. In some embodiments, the therapeutic RNA molecule is not substantially homologous (e.g., not more than 10%, 20%, 30%, 40%, 50%, 60%, or 70% homologous) to known cDNA sequences. Libraries generated by methods of the present invention may exhibit an advantage over libraries generated by other methods because the stem regions or self-complementary regions of the RNA molecules generated thereby are random and contain at least one mismatch and thus allow for screening the RNA molecules generated thereby by function, without any other significant sequence or expectation bias. In some embodiments, the advantage is the lack of self-complementarity in the loop region. In some embodiments, the advantage is the length of the stem region.

In some embodiments, the numbers of random sequences generated and/or of cells screened is designed to cover all possible sequences of the ds region of the RNA or a fragment thereof. For example, to cover all possible seed sequences (approximately residues 1-8 of the ds region), 65,500 sequences need be generated. In some embodiments, the seed sequence is held constant based on the previous RNA molecule obtained in a subsequent round of mutagenesis, while the remainder of the ds region is mutagenized. In some embodiments, the seed sequence is varied, while the remainder of the ds region is kept constant. In some embodiments, residues 2-8 of the seed sequence are kept constant, while residues 1, and 9 onward are varied.

In some embodiments, a method of the present invention avoids use of a high salt solution, such as those found in commercial kits for gel purification of DNA fragments from an agarose gel, during library construction. In some embodiments, electric current is run through the gel piece to elute the DNA into a dialysis membrane bag with pore sizes smaller than the DNA. In some embodiments, the method further comprises ethanol precipitation of the DNA. In some embodiments, all steps in the library purification (excepting enzyme digests) are performed at 0-4° C. In some embodiments, pH buffer is present during all times during the library construction. In some embodiments, use of bromophenol blue is avoided during library construction. In some embodiments, 1 of the above precautions reduces the likelihood of formation of intramolecular hairpins during library construction. In some embodiments, flanking sequences on both sides of the stem loop cassette, as introduced during methods of the present invention, prevent formation of intramolecular hairpins during subsequent steps.

In some embodiments, the length of the stem or self-complementary region of shRNA molecules of the present invention may be 6, 7, 8, 9, 10, 11, 12, 13, 14, 15, 16, 17, 18, 19, 20, 21, 22, 23, 24, 25, 26, 27, 28, 29, 30 or even more than 30 nucleotides (nt) long.

In some embodiments, the shRNA molecules have a 3' overhang (in some embodiments, a 2 nt 3' overhang). In some embodiments, shRNA molecules of the present invention have a stem or self-complementary region of 29 nt with a 3' overhang. In some embodiments, the overhang is 2 nt. In some embodiments, the shRNA molecules have a stem or self-complementary region of 27 nt with a 3' overhang. In some embodiments, the overhang is 2 nt. In some embodiments, the shRNA molecules have a stem or self-complementary region of 19 nt with a 3' overhang. In some embodiments, the overhang is 2 nt.

In some embodiments, shRNA molecules of the present invention have a stem or self-complementary region of 21-23 nt (e.g., 22 nt) with an intervening loop sequence of 15-25 nt (e.g., 19 nt). In some embodiments, the intervening loop sequence is 1-30 nt. In some embodiments, the shRNA molecules have a mismatch of one or more base pairs in the self-complementary region. In some embodiments, the shRNA molecules have a deletion in one strand of the self-complementary region. In some embodiments, the deletion causes an internal loop that is recognized by a cellular enzyme.

In some embodiments, the length of the loop region of shRNA molecules of the present invention may range between 3-20 nt, 4-20 nt, 5-20 nt, 6-20 nt, 7-20 nt, 8-20 nt, 9-20 nt, 10-20 nt, 3-15 nt, 4-15 nt, 5-15 nt, 6-15 nt, 7-15 nt, 8-15 nt, 10-15 nt, 3-12 nt, 4-12 nt, 5-12 nt, 6-12 nt, 7-12 nt, 8-12 nt, 10-12 nt, 3-10 nt, 4-10 nt, 5-10 nt, 6-10 nt, 7-10 nt, 8-10 nt, or 6-8 nt in length. In some embodiments, the length may be 6, 7, 8, 9, 10, 11, 12, 13, 14, 15, 16, 17, 18, 19, 20, 21, 22, 23, 24, 25, 26, 27, 28, 29, 30 or even more than 30 nucleotides (nt) long.

The loop region of RNAi molecules described herein may be taken from a known or naturally occurring RNAi molecule. In some embodiments, the loop sequence is not from a known or naturally occurring RNAi molecule. It will be understood to those skilled in the art that a variety of loop sequences, including previously unrecognized ones, are suitable for methods of the present invention.

Naturally occurring RNAi molecules are well known in the art, and are described for example, in Griffiths-Jones et al (Griffiths-Jones S, Grocock R J, van Dongen S, Bateman A, Enright A J. Nucl Acids Res, 2006, 34: D140-D144) and in Griffiths-Jones S (Nucl Acids Res, 2004, 32: D109-D111).

RNA molecules of the present invention may be a substrate for an RNA-induced silencing complex (RISC). In some embodiments, methods of the present invention further comprise digesting an RNA molecule of the present invention to obtain a short-interfering (siRNA) molecule. RNA molecules of the present invention may be a substrate for an RNase III family enzyme. In some embodiments, the enzyme is a Class I RNase III family enzyme. In some embodiments, the enzyme is a Class II RNase III family enzyme. In some embodiments, the enzyme is a Class III RNase III family enzyme. In some embodiments, the enzyme is Dicer. In some embodiments, the enzyme is Drosha. In some embodiments, processing by a RISC or RNase III family enzyme converts the RNA molecule to a form with a biological activity. Substrates for RISC and RNase III family enzymes are well known in the art, and are described, for example, in Jaronczyk K et al (Exploring the functions of RNA interference pathway proteins: some functions are more RISCy than others. Biochem J. 2005 May 1; 387(Pt 3):561-71) and in Banan M et al (The ins and outs of RNAi in mammalian cells. Curr Pharm Biotechnol. 2004 October; 5(5):441-50). In some embodiments, an RNA molecule of the present invention is cleaved by one of the above enzymes or complexes into a double-stranded RNA with a stem or self-complementary region of 20 nt and a 3' overhang (e.g., a 2 nt 3' overhang). In some embodiments, the digestion occurs inside a target cell.

In some embodiments, RNA molecules of the present invention mimic a product of an RNase III family enzyme. In some embodiments, the RNA molecules have a 20 nucleotide ds region and a 2 nucleotide 3' overhang.

In some embodiments, biologically active RNA molecules of the present invention bind to a sequence shared by several genes. In some embodiments, the shared sequence is found in the 3' untranslated region (UTR) of the target mRNAs. In some embodiments, the shared sequence is found in the 5' UTR of the target mRNAs. In some embodiments, the shared sequence is found in the coding portion of the target mRNAs. In some embodiments, the shared sequence is found in an intron. In some embodiments, the shared sequence is found in a combination of the above regions.

In some embodiments, the target of an RNA molecule of the present invention is an mRNA molecule. In some embodiments, the target is another type of RNA. In some embodiments, the target is ribosomal RNA (rRNA), transfer RNA (tRNA), messenger RNA (mRNA), small nuclear RNA (snRNA), small nucleolar RNA (snoRNA), microRNA (miRNA), or XIST RNA. In some embodiments, the target is a deoxyribonucleotide molecule. In some embodiments, the target is another type of nucleotide molecule. In some embodiments, the target is a protein molecule. In some embodiments, the target is a cofactor. In some embodiments, the target is a lipid. In some embodiments, the target is another type of cellular non-nucleotide molecule.

The complementary region between RNA molecules of the present invention and its target sequence may be 6, 7, 8, 9, 10, 11, 12, 13, 14, 15, 16, 17, 18, 19, 20, 21, 22, 23, 24, 25, 26, 27, 28, 29, 30 or even more than 30 nucleotides (nt) long. In some embodiments, an RNA molecule of the present invention binds different target sequences on different genes. In some embodiments, the different target sequences are not all the same length.

In some embodiments, the RNA molecule expressed by a vector of the present invention is fully complementary to its target sequence. In some embodiments, the RNA molecule is partially complementary to its target sequence. In some embodiments, the RNA molecule is complementary to its target sequence along most of the length of the RNA molecule, with a non-complementary overhang region. In some embodiments, the RNA molecule expressed by a vector of the present invention has one or more mismatched residues with respect to its target sequence. In some embodiments, the RNA molecule hybridizes to its target sequence under physiological conditions. In some embodiments, the RNA hybridizes to its target sequence under stringent conditions.

In some embodiments, expression of an RNA molecule of the present invention inside a cell causes translational repression of the target RNA molecule. In some embodiments, expression of the RNA molecule causes cleavage or degradation of the target RNA molecule. In some embodiments, whether translational repression, cleavage or degradation occurs depends on the level of complementarity between the RNA molecule of the present invention and the target RNA molecule, and the length of the complementary region.

In other embodiments, methods of present invention are used to identify sequences that influence cell survival, cell health, cell death, cell differentiation, or any other assayable phenotypic change. In some embodiments, sequences influencing stem-cell differentiation into cell types of medical interest are identified using the library. In some embodiments, the RNA molecules identified have utility as siRNAs for stem-cell therapeutics.

In one embodiment, delivery of shRNA or siRNA therapeutics provided herein to specific tissues is beneficial for protecting against infectious agents. In another embodiment, delivery of shRNA or siRNA therapeutics provided herein to specific tissues is beneficial for reversing cellular defects associated with genetic disorders. In another embodiment, delivery of shRNA or siRNA therapeutics provided herein to specific tissues is beneficial for the control of cellular differentiation states.

In one embodiment, any cellular system with a selectable phenotype, such as survival, enhanced growth, or a flow-sortable marker, and with a reasonable signal-to-noise ratio, is amenable to shRNA or siRNA therapeutics using the compositions and methods provided herein.

All sequence citations, accession numbers, references, patents, patent applications, scientific publications or other documents cited are hereby incorporated by reference.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

Example 1

Dual RNAi Expression by a Retroviral Vector

A retroviral vector was designed to express simultaneously two shRNAs. The vector contained enhanced, farnesylated green-fluorescent protein (eGFPf), which allows straightforward flow-sorting of infected or transfected cells, and a G418 resistance gene, which facilitates selection of infected or transfected cells. The eGFP gene of the retroviral vector pQCXIX® (Clontech) was replaced with eGFPf, and two copies of a Pol III-dependent H1-promoter cassette (from pSuper-Retro) were cloned into the inactivated long-terminal repeat of pQCXIX, to create the vector pQe2. In each H1-promoter cassette of pQe2, 2 unique restriction enzyme sites were incorporated to allow independent cloning of shRNA constructs into each cassette. pQe2 was used to knock down expression of proteins important in spindle-checkpoint function; both shRNA knockdown (by Western and other analyses) and eGFP expression was validated. Thus, expression of target genes can be knocked down by RNA molecules. In addition, expression of both a particular gene of interest (e.g., frataxin) can be suppressed in normal cells to induce a phenotype, including a disease phenotype, and one or more random targets can be suppressed as well to alter or reverse the phenotype.

Example 2

Vector Modification pSuper-Retro (Oligoengine®, Seattle, Wash.), which can be packaged as a retrovirus and includes the gene encoding enhanced green fluorescent protein (eGFP) and a G418-resistance gene, was used in the cloning methods below. The Bgl I fragment of the spacer sequence was replaced with a Bgl II-Bbs I-Mlu I fragment. By then cutting with Bbs I, filling in with Klenow, and cutting with Not I, the linearized vector depicted in FIG. 5 was created. Other than Pme I, which was eliminated in creating the spacer sequence, pSuper-Retro lacked all the relevant restriction enzyme sites needed for the procedure shown in FIGS. 6-8, and thus was suitable for the procedure.

In the development of alternate vectors, the Bgl II cloning site and the spacer sequence between Bgl II and Hind III of pSuper-Retro were replaced with Xcm I and Sfi I to eliminate the unique Pme I site. (The region from just before the Bgl II site back to the unique BlpI site was PCR amplified, using a primer with a tail containing the sequences for Xcm I, Sfi I, and Hind III, and the vector's Blp I-Hind III fragment was replaced with the PCR product digested with Blp I and Hind III). A spacer sequence was added between XcmI and SfiI by amplifying the old spacer sequence, up to but not including the PmeI site, using primers with tails containing the sequences for XcmI and SfiI. The rationale for adding back a spacer sequence was, in this experiment, to simplify the elimination of single-cut vector and thereby maximize the efficiency of the library ligation. Other than Pme I, which was eliminated as described above, pSuper-Retro lacked all the relevant restriction enzyme sites needed for the procedure shown in FIGS. 3, 4, and 5, and thus was suitable for the procedure.

Many other vectors could be used and many other restriction enzyme combinations are suitable for the methods in this and the other Examples herein. For example, enzyme pairs that can be used to create non-complementary loop sequences (with the resulting loop sequences in parentheses) include, EcoN I/Aar I (CCTCCCGC), Sma I/Aar I (CCCC), Stu I/Apa I (AGGC), Bsu36 I/Aar I (CCTCAC), Bbv Cl/Aar I (CCTCAC), Ear I/Aar I (TCTTCCGC), etc.

Example 3

Creation of a Library of Partially Self-Complementary RNA Molecules

A set of single-stranded (ss) DNA molecules was obtained, comprising, from 5' to 3', a first constant region, followed by a region of random sequence, in this embodiment a random sequence of 21 nucleotides (nt) ("N21"), followed by a second constant region containing 1 strand of a site of a first restriction enzyme (in this case EcoNI). A representation of a single ss molecule from the set is depicted in FIG. 1 as "ssI," also referred to herein as "single-stranded nucleic acid intermediate I." A primer mismatched at two positions ("primer A" in FIG. 1) was annealed to the oligo, such that the complementary strand, when in double-stranded form, is a substrate for a second restriction enzyme (in this case AarI), but not the first restriction enzyme, as depicted in FIG. 1. One round of extension generated a complementary strand to most of ssI (bottom strand of ssIB in FIG. 1). After the single extension, a hairpin-loop linker ("linker B" in FIG. 1) was ligated to the staggered, complementary end of the extended oligonucleotide, generating nucleic acid intermediate II ("n.a. II" in FIG. 1). Nucleic acid intermediate II contains, in 5'-3' order, (a) a first copy of the first constant region; (b) a first copy of N21; (c) a first copy of the second constant region; (d) the hairpin-loop linker; (e) the reverse complement of the second constant region; (f) the reverse complement of the region of random sequence ("N21c"); and (g) the reverse complement of the first constant region (depicted in bottom of FIG. 3).

Figure 2:
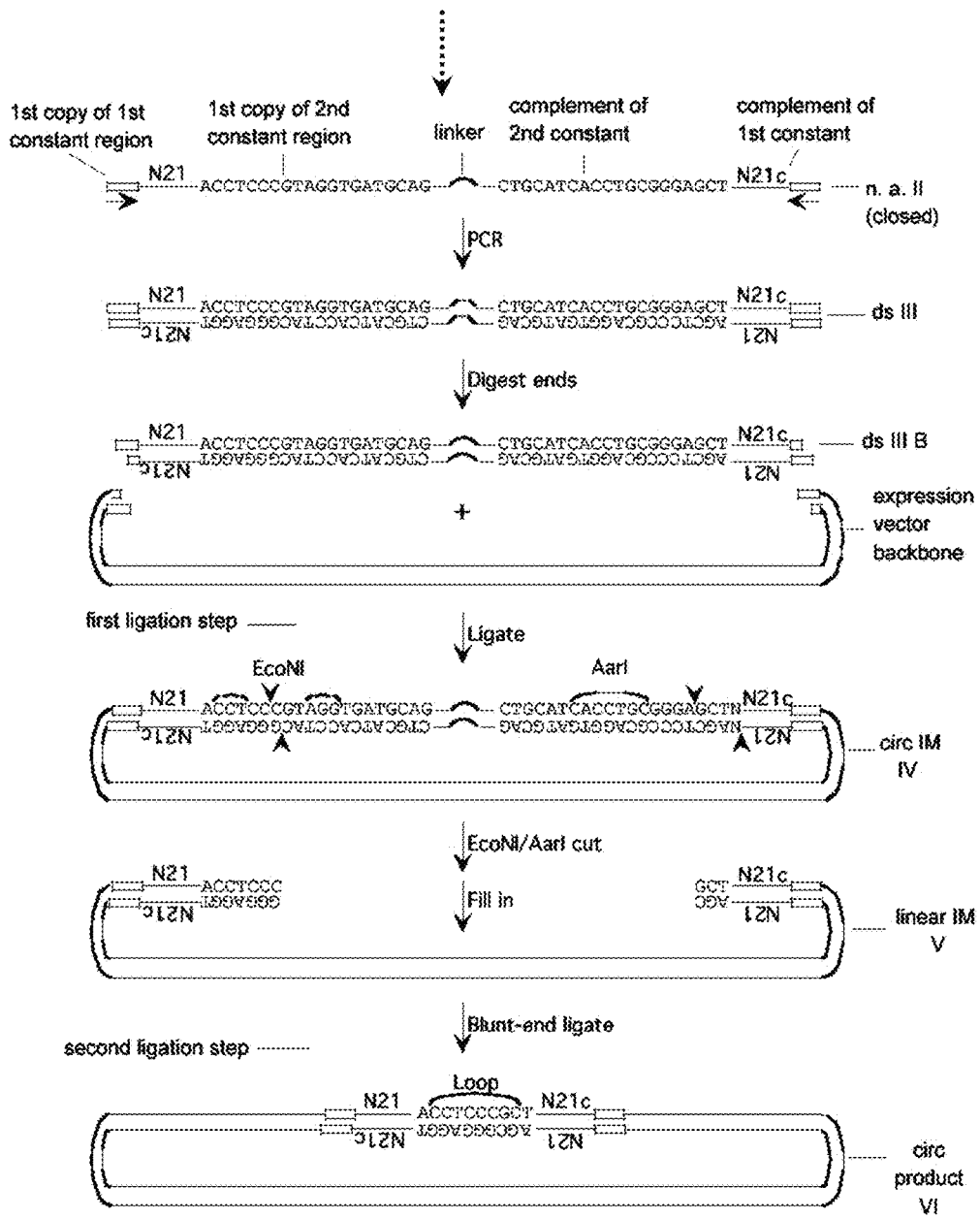
FIG. 2: Strategy (Strategy I) for creation of a library of expression vectors for partially self-complementary RNA molecules, part II. Described in Example 3. Sequences of 10 or more nt and not previously assigned a SEQ ID No are listed as SEQ ID No: 7-12.

As depicted in FIG. 2, the single-stranded product depicted at the bottom of FIG. 1 is suitable for amplification by PCR, thereby generating a double-stranded intermediate IR ("ds III" in FIG. 2). ds III contains, in 5'-3' order with respect to the top strand, (a) a first, double-stranded copy of the first constant region; (b) a first, double-stranded copy of N21; (c) a first, double-stranded copy of the second constant region; (d) a double-stranded copy of the hairpin-loop linker; (e) a second, inverted double-stranded copy of the second constant region; (f) a second, inverted double-stranded copy of N21c; and (g) a second, inverted double-stranded copy of the first constant region.

After PCR, the ends are restriction-enzyme digested, using a restriction enzyme site in the first constant region, and the product is ligated into a vector (first ligation step, FIG. 2), downstream of the polymerase-III H1-RNA promoter, thereby generating circular intermediate IV ("circ intermediate IV"). The resulting plasmid is then restriction digested with EcoNI and AarI. As a result of the original mismatched primer, only 1 of the 2 restriction enzyme sites is found on each side of the plasmid insert. Both enzymes leave overhanging 5' ends. After filling in to create blunt ends, the plasmid is ligated back into a circle in a unimolecular, blunt-end ligation (second ligation step, FIG. 2), thereby generating a circular product VI ("circ product VI"). The resulting plasmids contain regions of random sequence, each followed by a downstream non-conserved loop sequence, and then followed by a reverse complement of the random sequence, all in the same, coding strand of DNA, and thus expressed a library of shRNA molecules with a 22-base-pair stem containing a random, 21-base-pair region followed by a TA pair, and a non-complementary, 8 nt loop.

In this embodiment, there is a complementary T-A flanking the loop (bottom of FIG. 2). This is necessitated by the need to match the lead base-pair in the original mismatch extension shown at the top of FIG. 1. In additional experiments, by creating 4 libraries, each with a different base at this position, and then mixing them, all possibilities of a random 22-base-pair sequence in the stem are made. These constructs thus express an shRNA with a random, 22-base-pair stem, and a non-complementary, 8 nt loop.

Example 4

Figure 5:
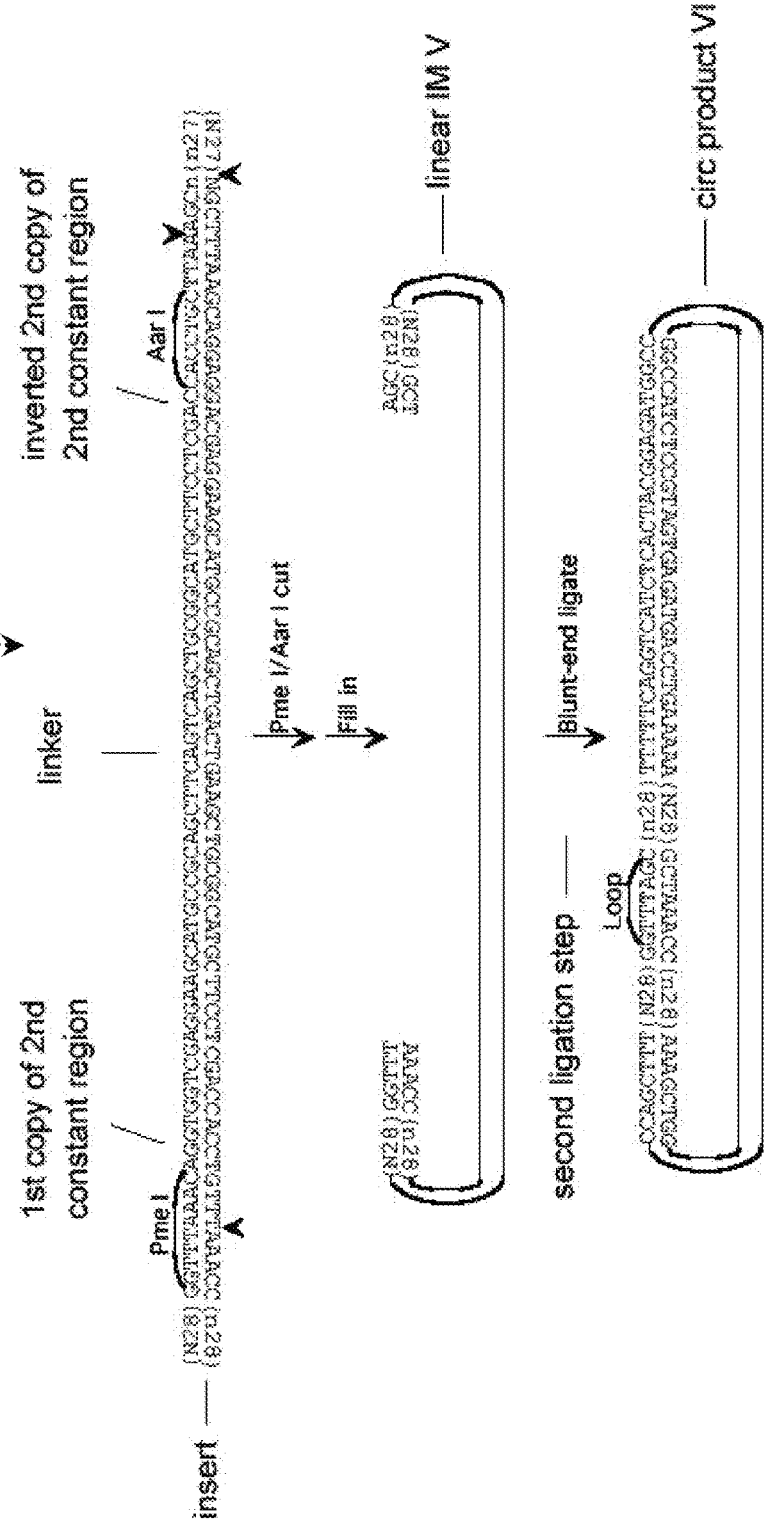
FIG. 5. Additional approach (Strategy II) for creation of a library of partially self-complementary RNA molecules, part III, creation of the non-complementary loop sequence. Described in Example 4. Sequences of 10 or more nt and not previously assigned a SEQ ID No are listed as SEQ ID No: 28-33.

An Additional Approach for Creation of a Library of Partially Self-Complementary RNA Molecules FIGS. 3, 4, and 5 illustrate an additional approach for generating the library of expression vectors for RNAi. The DNA oligomer ("oligo") ssI on the top line of FIG. 3 is similar to ssI of FIG. 1; "N28" refers to 28 random nucleotides. ssI contains one strand of a PmeI site in the second constant region, just downstream of the N28 sequence. Simple extension from a primer (with 2 mismatches; "primer A" in FIG. 3) created the reverse complement of most of the first constant region, the region of random sequence ("n28"); and the second constant region of ssI, thereby generating double-stranded intermediate IB ("ds IB"). Ligation of a hairpin-loop linker to 1 end of the extended oligonucleotide covalently linked the 2 strands of ds Ib containing the N28 and n28 sequences, thereby generating nucleic acid intermediate II ("n.a. II"). (The compatible sticky ends of the extended oligonucleotide and the hairpin-loop linker were from SalI and Xho I sites, respectively; digestion with Sal I and Xho I cut homodimers of the extended oligonucleotide or hairpin-loop linker, respectively, but did not cut the desired, heterodimeric product, thereby allowing gel separation by size.) n.a. II contains, in 5'-3' order, (a) a first copy of the first constant region; (b) a first copy of the region of random sequence "N28"; (c) a first copy of the second constant region; (d) the hairpin-loop linker; (e) the reverse complement of the second constant region; (f) the reverse complement of the region of random sequence "n28"; and (g) the reverse complement of the first constant region.

Use of a mismatched primer created one strand of an Aar I recognition sequence in the reverse complement of the second constant region, just upstream of the n28 sequence; which was not present in the first copy of the second constant region. In addition, the mismatched primer eliminated the Pme I recognition sequence in the reverse complement of the second constant region. This created the asymmetry used to generate a non-complementary loop between N28 and n28 after insertion into the vector (see hereinbelow and FIG. 5).

Creating the Reverse Complement of the Random Stem Sequence and Covalently Linking the Two.

As depicted in FIG. 4, n.a. II is suitable for simple extension from mismatched primer B (top of FIG. 4), thereby generating double-stranded intermediate III ("ds III"). The primer is recessed to create a 5' overhang (AGA) in dsIII (see below). The mismatch in the primer eliminates the BtgZ I site at one end of dsIII. ds III contains, in 5'-3' order with respect to the top strand, (a) a first, double-stranded copy of the first constant region; (b) a first, double-stranded copy of N28; (c) a first, double-stranded copy of the second constant region; (d) a double-stranded copy of the hairpin-loop linker; (e) a second, inverted double-stranded copy of the second constant region; (f) a second, inverted double-stranded copy of n28; and (g) a second, inverted double-stranded copy of the first constant region.

As noted above, dsIII contains a 5' overhang (AGA) compatible with the 5' overhang in the expression vector backbone digested with Sfi I (FIG. 4), and contains an BtgZ I site on the other end of the molecule. Digestion of ds III with BtgZ I, which cuts 10 and 14 nt away from the recognition site, cuts the DNA immediately before the first random nt of the original N28, as well as 4 nt further in on the opposite strand, leaving a recessed 3' end (ds IIIB). Filling in with Taq polymerase regenerates the 4 nt in the strand opposite the original N28, plus a 3' adenine overhang (ds IIIC), which is compatible with the 3' thymidine overhang in the expression vector backbone digested with Xcm I. dsIIIC is then ligated into the expression vector backbone (first ligation step, FIG. 4), to generate circular intermediate IV ("circ IM IV"). A variety of expression vector backbones are suitable for this step, e.g., Modified pSuper-Retro (Example 2).

Creating the Vector Insert and Insertion into the Vector

The purpose of the BtgZ I digestion and filling in is to retain the 5 thymidines that serve as the pol III transcription termination signal immediately downstream of the original n28 sequence, while eliminating the adenines upstream of the original N28 sequence and replacing them with pyrimidines (from the vector). Because pol III tends to initiate transcription early when purines are available immediately upstream of the normal start site, pyrimidines immediately upstream favor initiation of transcription at the normal start site, which is 25 nucleotides downstream of the TATA box in the H1 promoter. Thus, in circ IM IV, the normal start site falls on the first nucleotide of the original N28 sequence, which is marked "+25" at the bottom of FIG. 4 (see below).

Creation of the Non-self-complementary Loop Sequence

The top of FIG. 5 depicts the vector insert sequence of circ IM IV between the N28 and n28 sequences. The insert sequence contains a PmeI/AarI restriction site asymmetry as a result of the restriction site asymmetry in n.a. II (described hereinabove). Digestion of circ IM IV with Pme I creates a blunt end preceded by GGTTT in the sense strand. Digestion with Aar I cuts the DNA three nt before the first random nucleotide of the original n28, as well as 4 nucleotides further in on the opposite strand, leaving a recessed 3' end. Filling in with Klenow creates a blunt end followed by AGC in the sense strand ("linear intermediate V" in FIG. 5). Uni-molecular, blunt-end ligation of linear IM V (second ligation step, FIG. 4), yields circular product VI ("circ product VI"), containing a non-self-complementary loop region with sequence GTTTAG between N28 and n28.

Use of a matching lead base-pair in the original primer extension shown at the top of FIG. 3 was the reason for the complementary G-C flanking the non-self-complementary loop depicted in FIG. 5. In another embodiment, by repeating the procedure shown in FIGS. 3, 4, and 5, each time with a different base at the lead position for the first primer extension, 4 sub-libraries are created, which, when mixed, constitute an shRNA library with a random 29-base-pair stem and a non-self-complementary loop of GTTTAG. A pol III promoter (H1), ending in 4 pyrimidines, precedes each shRNA construct in the library, with the transcriptional start site falling on the first random nucleotide. Five thymidines immediately downstream of the second half of the 29-base-pair stem serve as the transcription termination signal.

Example 5

Figure 6:
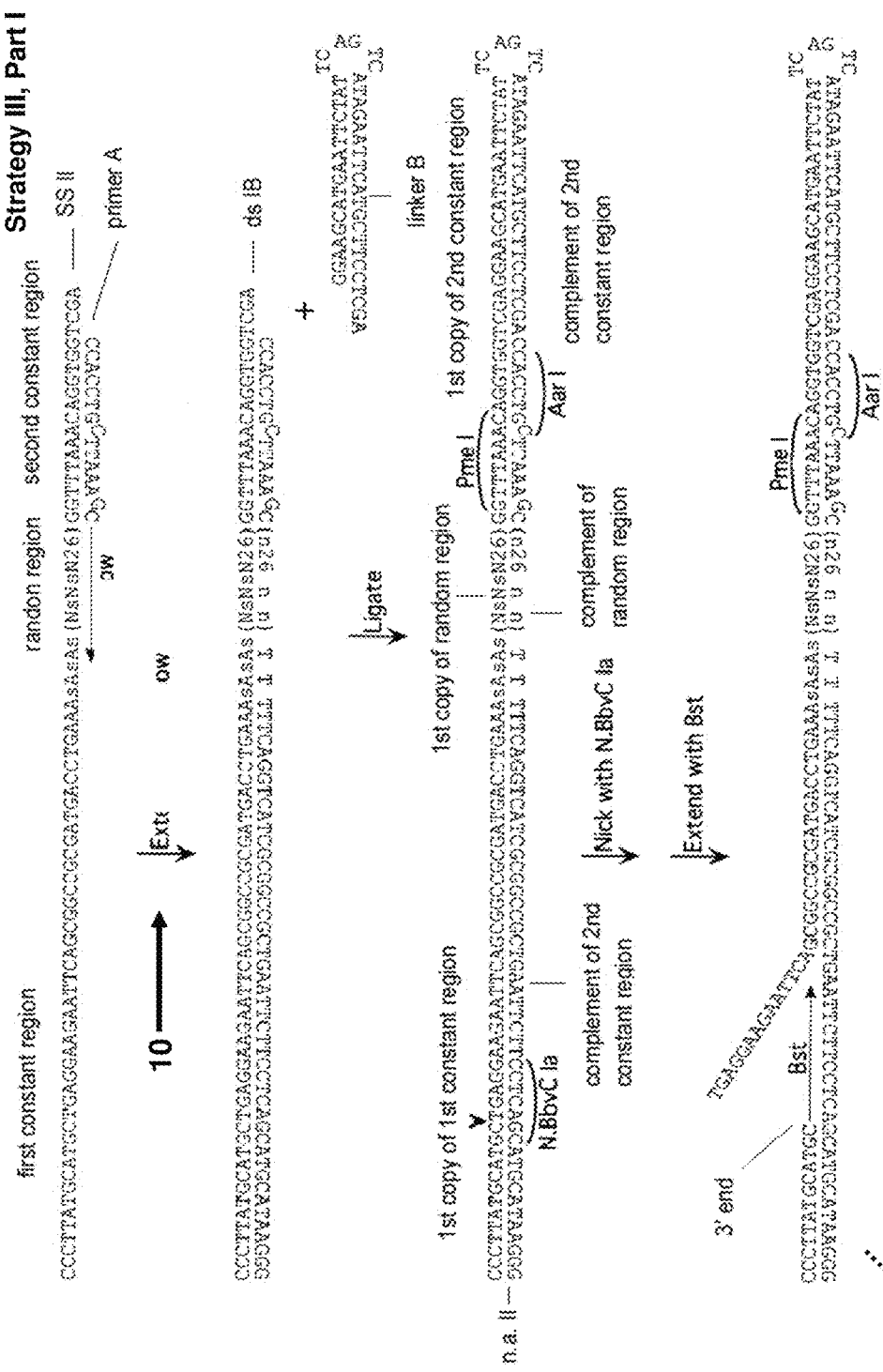
FIG. 6. Third approach (Strategy III) for creation of a library of partially self-complementary RNA molecules, part I. Described in Example 5. Sequences of 10 or more nt and not previously assigned a SEQ ID No are listed as SEQ ID No: 34-37.
Figure 7:
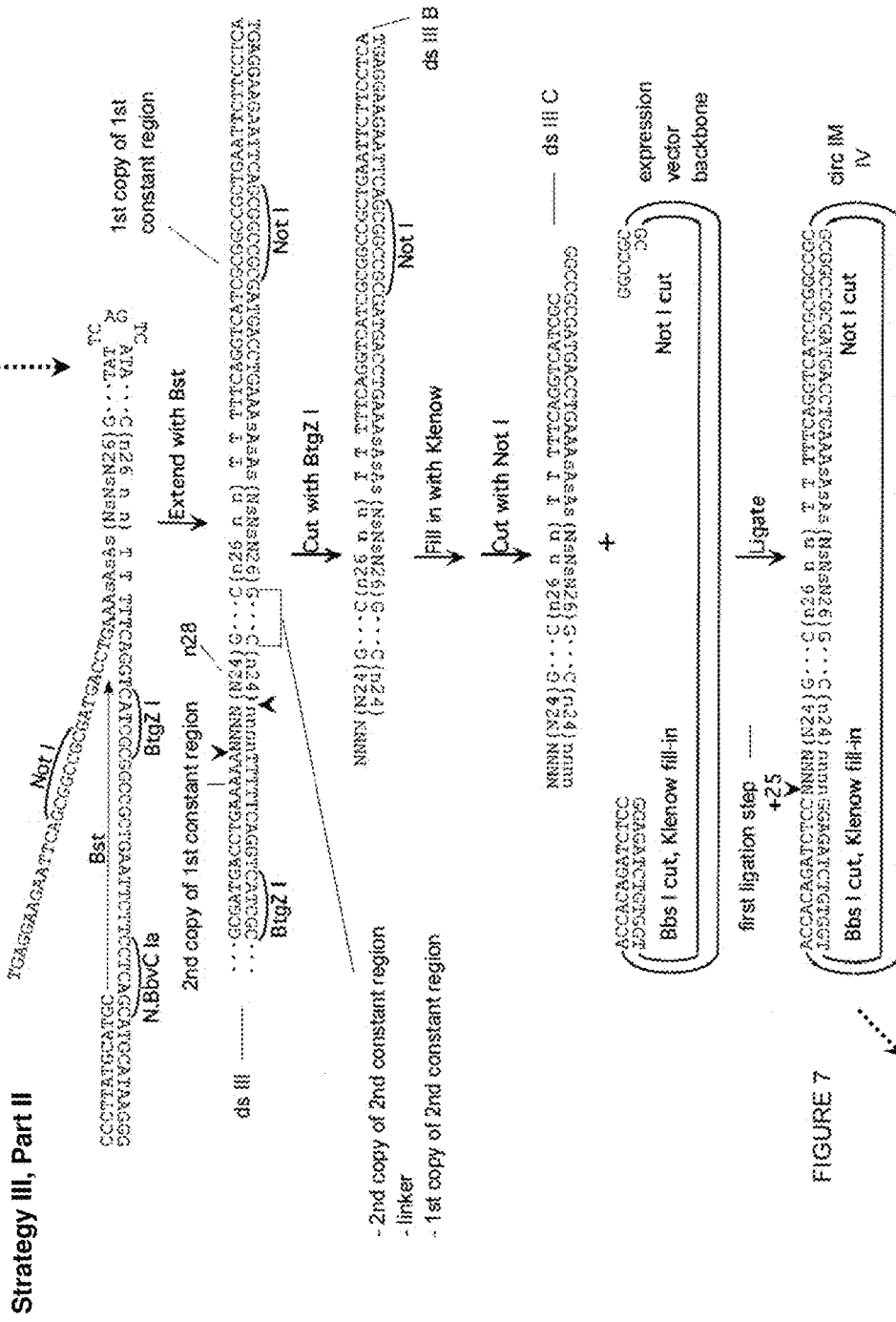
FIG. 7. Third approach (Strategy III) for creation of a library of partially self-complementary RNA molecules, part II. Described in Example 5. Sequences of 10 or more nt and not previously assigned a SEQ ID No are listed as SEQ ID No: 38-51.
Figure 8:
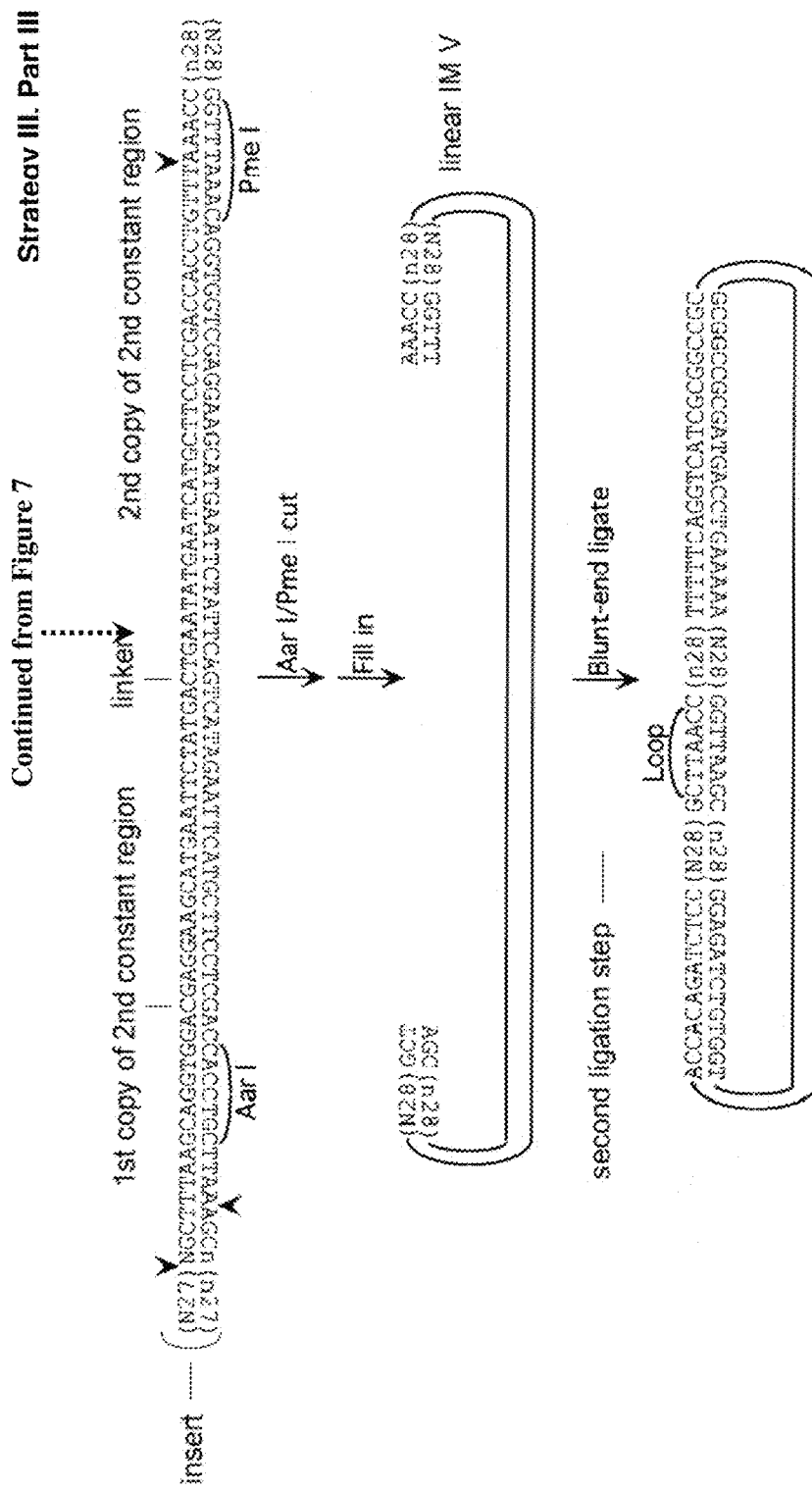
FIG. 8. Third approach (Strategy III) for creation of a library of partially self-complementary RNA molecules, part III. Described in Example 5. Sequences of 10 or more nt and not previously assigned a SEQ ID No are listed as SEQ ID No: 52-53.

A Third Approach for Creation of a Library of Partially Self-Complementary RNA Molecules FIGS. 6-8 illustrate a third approach used for generating the library of expression vectors for RNAi:

Creating the Reverse Complement of the Random Stem Sequence, Covalently Linking the Two, and Starting the Second Extension As in the previous method, a single-stranded DNA molecule "single-stranded nucleic acid intermediate I" with a region of random sequence sandwiched between 2 constant regions ("first constant region" and "second constant region," 5' and 3', respectively, to region of the random sequence) was synthesized (referred to as "ss I" in FIG. 6). The second constant region contains 1 strand of a Pme I recognition site just downstream of the NsNsN26 sequence. In ss I, "NsNsN26" refers to 28 random nt, the first 2 of which are followed by phosphorothioate bonds (to create asymmetric BtgZ I cutting after the second extension, as described hereinbelow and depicted in FIG. 7). ss I also contained 1 strand of Not I and BtgZ I recognition sequences, as depicted for ds Ib in FIG. 6.

Simple extension from a recessed primer, containing 2 mismatches, created ds Ib, containing the reverse complements of: (a) a fragment of the first constant region, (b) the NsNsN26 sequence, and (c) the second constant region.

Use of a mismatched primer created one strand of an Aar I recognition sequence in the reverse complement of the second constant region, just upstream of the n26nn sequence; which was not present in the first copy of the second constant region. In addition, the mismatched primer eliminated the Pme I recognition sequence in the reverse complement of the second constant region. This created the asymmetry used to generate a non-complementary loop between NsNsN26 and n26nn after insertion into the vector (see hereinbelow and FIG. 8).

Ligation of a hairpin-loop linker ("linker B") to the recessed-primer end of ds Ib covalently linked the 2 strands of ds Ib, containing the NsNsN26 and n26nn sequences, and completed the reverse complement of the first constant region, thereby generating nucleic acid intermediate II ("n.a. II"). (The compatible sticky ends of ds Ib and linker B are from Sal I and Xho I sites, respectively; digestion with Sal I and Xho I cut homodimers of ds Ib or linker B, respectively, but did not cut the desired, heterodimeric product, thereby facilitating gel separation by size.) n.a. II contains, in 5'-3' order, (a) a first copy of the first constant region; (b) a first copy of the region of random sequence ("NsNsN26"); (c) a first copy of the second constant region; (d) the hairpin-loop linker; (e) the reverse complement of the second constant region; (f) the reverse complement of the region of random sequence ("n26nn"); and (g) the reverse complement of the first constant region.

To facilitate the second extension (starting at the bottom of FIG. 6 and continuing at the top of FIG. 7), a nick site was created with the nicking enzyme N.BbvC, which cuts only 1 strand of DNA (indicated by arrowhead in FIG. 6), then the resulting 5' fragment was extended with the strand-displacing DNA polymerase Bst (depicted at bottom of FIG. 6 and top of FIG. 7) to create the reverse complement of n.a. II, thereby generating double-stranded intermediate III (ds III). ds III contains, in 5'-3' order with respect to the top strand, the following regions, all double-stranded: (a) a second, inverted copy of the first constant region; (b) a second, inverted copy of the random region (n28); (c) a second, inverted copy of the second constant region; (d) a copy of the hairpin-loop linker; (e) a first copy of the second constant region; (f) a first copy of the random region (N28); and (g) a first copy of the first constant region. In ds III of this embodiment, the regions are synthesized in the reverse order from the previous Example, and thus are depicted in the reverse order from the previous Example.

The phosphorothioate bonds originally appearing in ssI (top of FIG. 6) created a restriction site asymmetry in ds III, wherein BtgZ I only cuts 1 end of ds III. Digestion of ds III with BtgZ I cut the DNA immediately before the first random nucleotide of the newly synthesized N28, as well as 4 nucleotides further in on the opposite strand, leaving a recessed 3' end (FIG. 7; ds IIIB) Filling in with Klenow regenerated the four nucleotides in the strand opposite the newly synthesized N28, creating a blunt end. As described for the above Example, the asymmetric BtgZI digestion enabled inclusion of a TTTTT termination sequence after the last random nucleotide while changing the complementary AAAAA to 5 pyrimidines just upstream of the H1 transcription start site at the first random nucleotide.

Finishing the Second Extension to Create the Vector Insert, and Insertion into the Vector The asymmetric BtgZ I digestion also eliminated 1 of the 2 Not I sites. Digestion with Not I created the library insert (ds IIIC), which was ligated into the vector backbone (first ligation step, FIG. 7), thereby generating circular intermediate IV. The top of FIG. 8 depicts the vector insert sequence between the N28 and n28 sequences. As a result of the mismatch in primer A (FIG. 6), a unique Aar I site was present at 1 end of the insert and a unique Pme I site at the other end. Digestion with Pme I created a blunt end followed by AAACC in the sense strand. Digestion with Aar I cut the DNA 3 nucleotides before the first random nucleotide of the original n28, as well as 4 nucleotides further in on the opposite strand, leaving a recessed 3' end Filling in with Klenow fragment created a blunt end with GCT in the transcribed strand immediately following N28 ("linear intermediate V"). Uni-molecular, blunt-end ligation of linear intermediate V (second ligation step, FIG. 8), generated circular product VI, containing a non-complementary CTAAAC loop sequence between N28 and n28.

The transcribed strands of the inserts contained 5 pyrimidines upstream of the transcription start site (to increase the efficiency of starting transcription at +1, which pol III prefers to be a purine), followed by a 29-nt stem containing a 28-nt random sequence, followed by a non-complementary loop sequence, followed by the reverse complement of the 29-nt random sequence, followed by 5 thymidines (to terminate pol III transcription, which occurs after the second thymidine). Thus, the vectors encoded shRNAs with 29-nt stems and 2-nt overhangs.

To test the efficacy of the method, E. coli were transfected with circular IM IV, and 300,000 colonies were plated out. Plasmid DNA from 15 of these colonies was isolated, and inserts were sequenced. The sequences of all 15 inserts contained random sequences and their reverse complements separated by the Aar I-Pme I fragment depicted in the top of FIG. 8, exactly as predicted. In addition, the pool of intermediates was sequenced. The sequence data confirmed the presence of the expected constant sequences, and lack of bias in the random region, verifying the efficacy of the method. The base usage of the random sequences was 50.9% A/T and 49.1% G/C, demonstrating that the random region exhibits random character.

DNA was prepared from the remaining (~300,000) colonies, digested sequentially with Aar I and Pme I. and re-ligated. The ligation mix was used to transfect E. coli, and 1,000,000 colonies were plated out. Plasmid DNA was isolated from 5 of these colonies; all 5 had inserts of the proper size.

Following completion of the method, the random (n29) regions of 14 clones were sequenced. The sequences exhibited no detectable skewing, demonstrating that the method was efficacious, and the final product corresponded exactly to the desired product.

In addition, inserts from individual "clones" from the completed library were sequenced in their entirety. The sequence from these representative "clones" contained the N28 random sequence, followed by a "G" residue (supplied by the 3' constant region of the original ss DNA molecule), followed by the loop sequence, followed by a "C" residue, followed by the reverse complement of N28, (depicted as "n28."). The sequence corresponds to the bottom (upside-down) strand at the bottom of FIG. 8. Thus, the final product corresponded exactly to the desired product, re-confirming that the method was efficacious.

Example 6

Figure 9:
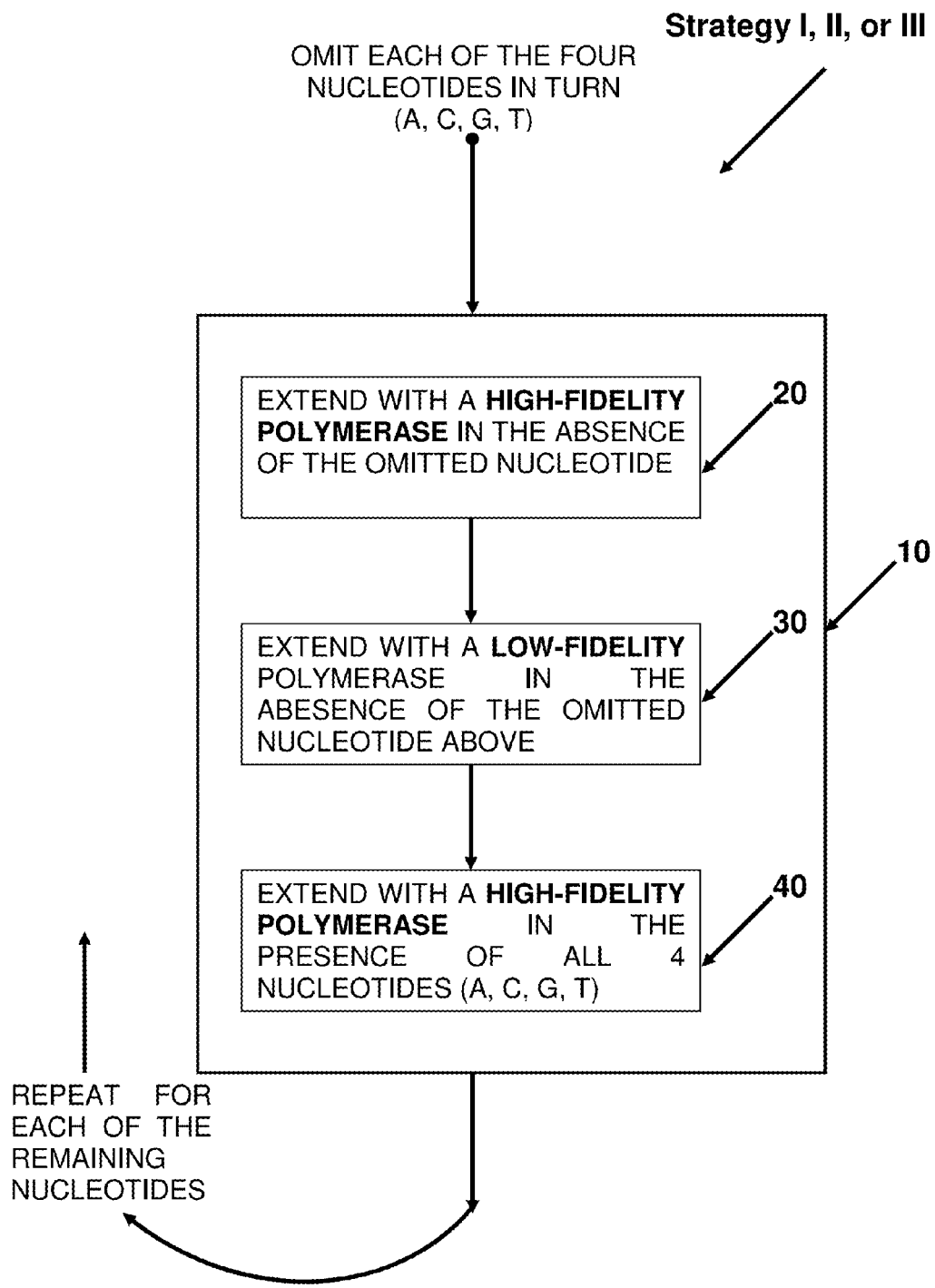
FIG. 9. Block diagram showing the steps for incorporating random mismatches of extension step 10 of Strategies I, II and III.

Creation of a Library of Double-Stranded RNA Molecules of Random Sequence Containing Random Mismatches FIG. 9 shows as a block diagram an approach that can be used in connection with the approaches of Examples 3-5 above for creating a library expression vectors that express shRNA molecules containing double stranded structures of random sequence that contain random mismatches. FIG. 9 shows in block diagram the first extension step 10 from FIG. 1 of Example 3, FIG. 3 of Example 4 and FIG. 6 of Example 5 in greater detail. Instead of using all four nucleotides (A, C, G, and T) during the first extension step 10 of Examples 3-5 to generate double-stranded RNA molecules of random sequence, the first extension step 10 is repeated four times, as described below, once for each of the four nucleotides, to also introduce random mismatches.

Initially, in the first step 20 of extension step 10, the polymerization reaction is conducted using a high-fidelity polymerase, such as Klenow, and one of the nucleotides is intentionally omitted. This causes the DNA polymerase (Klenow) to stall and generate "unfinished" fragments still annealed to the random templates. For example, if G is omitted, then Klenow will stall at the first C it encounters.

Next, in the second step 30 of extension step 10, the high-fidelity is replaced with a low-fidelity or an error prone polymerase, such as M-MuLV reverse transcriptase: RTase. The low-fidelity polymerase is used to continue the reaction with the selected nucleotide still omitted. Using the low-fidelity polymerase in this step 30 "forcefully" incorporates the wrong nucleotide into where the reaction stalled in the previous step 20. In this example, the RTase is used, still only in the presence of A, C, T and not G, to "mistakenly" add an A, C or T opposite C. The ratio of A/C/T here can be calibrated but there will likely be some sequence bias because RTase has certain preferences when incorporating the nucleotides "wrongly." However, the length of this step 30 will determine the number of mutations introduced.

Finally, in the last step 40 of extension step 10, the low-fidelity polymerase is replaced with a high-fidelity polymerase and the extension reaction 10 is finished in the presence of all four nucleotides. The extension reaction 10 is repeated for each of the four nucleotides. The products of the four reactions are combined, to create a pool having mutations against all four nucleotides.

Methods

The following is a detailed step by step protocol for the G-example (shown in bold) above.

Step1: generation of stop fragments

|  | A- | C- | G- | T- |  |
|---|---|---|---|---|---|
| Random oligo template/primer (~4 µg/0.1 nmole→16 µg) | 1 | 1 | 1 | 1 |  |
| Water | 14.5 | 14.5 | 14.5 | 14.5 |  |
| dATP (100 mM) | — | 0.5 | 0.5 | 0.5 | (50 nmole each) |
| dCTP (100 mM) | 0.5 | — | 0.5 | 0.5 |  |
| dGTP (100 mM) | 0.5 | 0.5 | — | 0.5 |  |
| dTTP (100 mM) | 0.5 | 0.5 | 0.5 | — |  |

Boil the above reactants for 3 minutes. Then, centrifuge at 14,000 rpm for 30 seconds, and cool to 37°C. Next add the following:

| NEB Buffer 2 | 2 | 2 | 2 | 2 |
|---|---|---|---|---|
| Klenow (exo-) (5U/λ) | 1 | 1 | 1 | 1 |

Incubate the above at 37°C for 30 minutes in 4 tubes (for a total of 80 µL). Combine and bring the final volume to 100 µL. Isopropanol precipitate using 70% EtOH. Wash twice and air dry.

Step2: RTase force fill

|  | A- | C- | G- | T- | ×4 |
|---|---|---|---|---|---|
| Mix the ~95 μL below first, then use them to resuspend the dried pellet. Template final = 1 μM | | | | | |
| Water | 82 | 82 | 82 | 82 | |
| NEB RTase buffer | 10 | 10 | 10 | 10 | |
| dATP volume used 1 | — | 100 mM→1 mM | 10 mM→0.1 mM | 50 mM→0.5 mM | |
| dCTP volume used 1 | 100 mM→1 mM | — | 100 mM→1 mM | 50 mM→0.5 mM | |
| dGTP volume used 1 | 1 mM→0.01 mM | 20 mM→0.2 mM | — | 100 mM→1 mM | |
| dTTP volume used 1 | 100 mM→1 mM | 0.2 mM→2 μM | 20 mM→0.2 mM | — | |
| After resuspending pellet add RTase | | | | | |
| NEB M-MuLV RTase (200U/λ) | 2.5/1 hr | 2.5 + 2.5/2 + 2 hr | 2.5 + 2.5/1 + 1 hr | 2.5 + 2.5/1 + 1 hr | |

Incubate the above at 42° C. in 4 tubes. Isopropanol precipitate using 70% EtOH. Wash twice and air dry.

Step3: Klenow fill-out

|  | A- | C- | G- | T- | ×4 |
|---|---|---|---|---|---|
| Mix the 50 μL below first, then use them to resuspend the dried pellet At this step, resuspension may be difficult. Solution may appear slightly cloudy. Pipette up/down thoroughly. Template final = 3.3 μM | | | | | |
| Water | 41 | 41 | 41 | 41 | |
| dNTP (10 mM each) | 2 | 2 | 2 | 2 | (final 400 μM each dNTP) |
| NEB Buffer 2 | 5 | 5 | 5 | 5 | |
| Klenow (exo−) (5U/λ) | 2 | 2 | 2 | 2 | |

Incubate the above at 37° C. for 30 minutes in 4 tubes. Combine and bring
the final volume to 100 μL. Isopropanol precipitate using 70% EtOH. Wash twice and air dry.

Library Characterization

Samples were taken of twenty shRNA-encoding DNA hairpin sequences obtained by the above method and sequenced. CTAAAC is the common, non-complementary loop sequence. Out of 92 clones sequenced ~72% have mismatches, ~18% do not have mismatches, and another ~10% do not even form hairpin structures since they are not even complementary.

The complexity of this mismatch library has been increased by 10-fold, from 300,000 (300K or first generation library of Example 5) to 3 million (3M or second generation library of the present Example).

Example 7

Use of the shRNA Library to Identify RNA Molecules with Ability to Inhibit Apoptosis
Materials and Experimental Methods Generation of High-titer Retrovirus High-titer retrovirus was generated by co-transfecting 293T cells with retroviral vector and pCL-Eco, which encodes both ecotropic envelope and gag-pol proteins, using an Effectene® transfection kit (Qiagen). Culture supernatant was harvested each day from 24-72 hours after transfection and used either to infect FL5.12 cells or frozen at −80° C. for future use. 1-2 million cells were seeded in each well of a 24-well plate and were centrifuged at 2500×g for 1 hour with viral supernatant, 5 μg/mL polybrene, and 0.3 ng/mL interleukin-3 (IL-3). Cells were stored in the incubator for 2 hours. Viral supernatant was replaced with fresh batches, and the spin/incubation process was repeated 2 more times. Infection efficiency was determined 24-48 hours later by flow cytometric analysis of GFP expression.

Results

The murine pro-B cell line FL5.12 is IL-3 dependent; 100% of the cells die by apoptosis after IL-3 withdrawal for 3 days, and >90% of cells can be rescued by expression of Bcl-xL59. To define a protocol for identification of RNA molecules that rescued the cells from apoptosis, FL5.12 cells were cultured in medium with IL-3 and switched to medium without IL-3 for 12, 24, 48, or 72 hours, after which the cells were returned to medium with IL-3. Both trypan blue exclusion and re-culturing for several days after switching back to medium with IL-3 demonstrated that either 48 or 72 hours was sufficient to ensure 100% loss of viability.

High-titer retroviral infection was calibrated to 30% GFP-positive FL5.12 cells using pSiren, pCL-Eco in a 2:1 molar ratio as a positive control, indicating that 30% of the cells were transduced with a recombinant RNA-expressing retroviral vector.

30% GFP-positive cells was chosen to avoid saturating the RISC complex. Because there is a finite amount of RISC complex per cell, more than 2 or 3 RNAi constructs present simultaneously may be less effective, unless the RNAi sequences are particularly potent. To maximize the chances of identifying effective shRNA sequences with even weak effects, interrogation of primarily 1 random shRNA per cell was thus performed. From the Poisson distribution, multiplicities of infection of 0.3 and 0.4 are associated with approximately 26% and 33% GFP positive cells, respectively, and associated with approximately 85% and 80% of GFP-positive cells being infected with only 1 shRNA-encoding construct, respectively.

Figure 10:
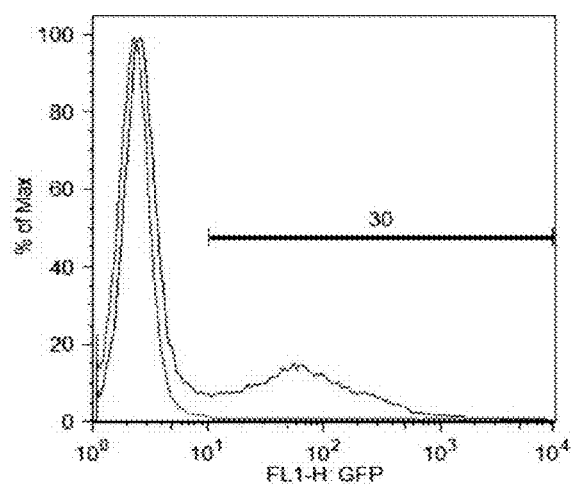
FIG. 10. Retroviral infection of 30% of FL5.12 cells.
Figure 11:
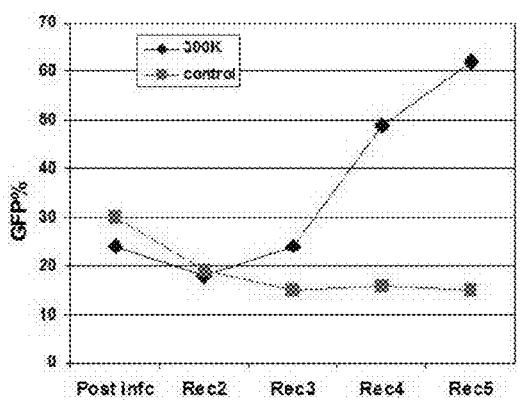
FIG. 11. Enrichment of GFP positive cells infected with the 300K library after multiple rounds of IL-3 withdrawal and recovery.

1 million FL5.12 cells were infected to ~30% GFP positivity with the 300,000 colony library of Example 5; GFP expression after expression is depicted in FIG. 10. IL-3 was withdrawn to select for shRNAs that enhance survival. After 3 days in IL-3-negative medium, cells were transferred back to regular growth medium with 0.3 ng/mL IL-3 for 3 days. To enrich for true positives, the process of withdrawal and return to regular medium was repeated. After 4 rounds of IL-3 withdrawal and recovery, the percentage of GFP-positive cells in the library-infected wells (but not in the control-infected wells) rose to 60%, indicating the presence of RNA molecules that conferred a relative survival advantage (FIG. 11).

Figure 12:
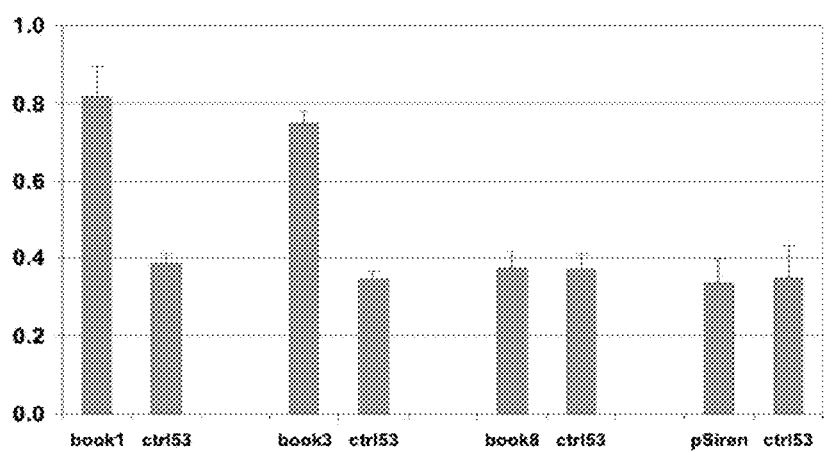
FIG. 12. Percent survival of FL5.12 cells (y-axis) infected with selected shRNA sequences ("books") after 15 hours of IL-3 withdrawal. Similar 2:1 survival ratios were seen after 2 days, though at lower levels. Ctrl53, random book; pSiren, vector.

10 shRNA-encoding sequences ("books") were retrieved by PCR, cloned back into pSiren, and sequenced. Of the 10, two were the same (books 1 and 7), indicating selective enrichment. FL5.12 cells were infected with 3 of the putative shRNA molecules separately (books 1, 3, and 8), each one assayed in 6 independent infections. The cells were subjected to 1 round of IL-3 withdrawal and recovery and subjected to a second withdrawal from IL-3. After 15 hours, cells were analyzed by flow cytometry, identifying infected cells by GFP fluorescence and dead cells by propidium iodide (PI) staining Fractions of GFP-positive (infected), PI-negative (live) cells relative to the start of the experiment (just prior to the first IL-3 withdrawal) are depicted in FIG. 12. Books 1 and 3 conferred a statistically significant improvement in survival relative to cells infected with a random book (ctrl53) or with vector alone (pSiren) (p<0.0001 in each case by Student's t-test). The improved survival with books 1 and 3 correlated with a decrease in caspase 3 enzymatic activity. Because the cycling of IL-3 withdrawal included a recovery segment, books 1 and 3 were tested for effects on growth rate and none were seen. The stem sequences of books 1 and 3 are as follows:

```
                                             (SEQ ID No: 1)
Book 1:      5'-GGGTAGCTACATTTGCATATGTGGATATG-3'.

(SEQ ID No: 2)
Book 3:      5'-GTGGATCAGTGTGTTATAGCTCGGGCAGG-3'
```

Thus, methods of the present invention are efficacious for identification of recombinant RNA molecules with therapeutic activity.

In other experiments, G1E or 293T cells are used to identify RNA molecules that protect against apoptosis, using methods analogous to the above method.

Example 8

Use of the shRNA Library Containing Random Mismatches to Identify RNA Molecules with Ability to Inhibit Apoptosis The 3M library (cherry tagged) of Example 6 with double-stranded RNA of random sequence containing random mismatches was introduced into FL5.12 cells. The cells were subjected to similar IL3 withdrawal/recovery cycles as described above in Example 7 for enrichment of true positives. Unlike the 300K experiment in Example 7 where FL5 cells were starved for 3 days, in this example cells were starved for 4 days at each cycle, to attempt to generate stronger hits with this new library. Enrichment was followed by percentage cells that are Cherry+ after each cycle. The results in FIG. 13 closely mimic the enrichment profile of the 300K library using GFP as a marker.

Some clones from cells that are 70% Cherry+ after 5 cycles have been isolated. They have been sequence and shown to contain mismatches.

Example 9

Confirmation of Function of RNA Molecules

In other experiments, following an RNAi library screening described in the above Example or one of the other Examples, the cell or cells in which the desired effect occurred are isolated, and the effective vector(s) are isolated and re-added to another population of cells. In another embodiment, positive-scoring RNAi sequences are retrieved by PCR (e.g, in the above methods, by using primers overlapping the Mfe I and Blp I sites flanking the shRNA insertion site in the retroviral vector), and the same or another form of inhibitory RNA containing the same random sequence (in other embodiments, shRNA, microRNA, or siRNA) is administered to an additional population of cells. Recapitulation of the phenotype in the additional population of cells confirms the ability of the inhibitory RNA molecule to elicit the desired phenotype. In other experiments, the new form of RNAi is a reversible form of RNAi (in another embodiment, siRNA synthesized in vitro; in another embodiment, a form whose effects are reversed by removing it from the media), and the new form of RNAi is shown to confer the phenotype of interest in a reversible fashion. In other experiments, candidate positive shRNA are tested in model systems other than the one from which they were originally identified.

Example 10

Iterative Pooling and Re-Testing to Enrich for True Positives

In other experiments, 100% loss of viability is not observed in the control cultures of one of the above apoptosis assays. In this case, surviving cells in the library-infected culture are pooled, and the putatively effective shRNA sequences are retrieved by PCR, re-cloned into the parent vector, and re-tested as a sub-library by iterative pooling and re-testing. The iterative pooling and re-testing achieves sequential enrichment of true positives.

For example, a screening assay with a 1% false-positive rate (i.e. that achieves 99% loss of viability) is used to screen an RNAi library of the present invention; 1 in 100,000 of the sequences in the library is a true-positive (e.g., confers significant resistance to apoptosis). 200,000 cells are infected, yielding, on average, two true positives and 2000 false positives. Surviving cells in the library-infected culture are pooled, and the putatively effective shRNA sequences are retrieved by PCR, re-cloned into the parent vector, and re-tested as a sub-library by iterative pooling and re-testing (e.g., in the above method, using primers that introduce Bgl II and Not I sites), yielding 200 true positives (2/2000×200,000) and 2000 false-positives. After a second round of pooling and re-testing, 20,000 true positives (200/2000×200,000) and 2000 false-positives are attained. Thus, after only two rounds of pooling and re-testing, the percentage of true positives (among all positives) can be increased from ~1% to more than 90%. For any of the above selection assays in which the numbers of surviving clones among library-infected cells and among control-infected cells are comparable, an increase in the numbers of surviving clones after re-introduction of pooled positives indicates the presence of true hits. Thus, screening methods of the present invention can be used even in assays with a significant false-positive rate.

Example 11

Use of Additional Apoptosis Assays to Identify RNA Molecules with Ability to Inhibit Apoptosis In Examples 7 and 8, the shRNA libraries were used in conjunction with the murine pro-B cell line, FL.5.12, to identify apoptosis-inhibiting RNA molecules. Conditions have been well established (IL-3 withdrawal) under which 100% of FL.5.12 cells die by apoptosis and >90% of cells are rescued (by Bcl-xL). In other embodiments, a variety of other cell types can be used by modifications of this technique.

In other experiments, staurosporine or another oxidant is used to induce apoptosis in 293T cells. In other experiments, a different IL-3-dependent cell line (e.g., 32D or Ba/F3) is used in place of FL5.12 cells. In other experiments, highly infectable sub-lines of 32D cells (obtainable from Dr. Warren Pear) are utilized. In other experiments, a VSV-G-expressing plasmid, pVSV-G, is used as an alternative to pHIT123. As an alternative to selection for survival selection by flow-sorting, for a surface marker or sortable reporter, is used. In other experiments, a cell line with tet-induced GFP is infected or transfected with the library in the presence of tet, and cells still positive for GFP after removal of tet are sorted and cloned. In other experiments, G1E cells (a murine proerythroblast line) are subjected to apoptosis by withdrawal of stem-cell factor (SCF).

In other experiments, RNAi selection is used in model systems that allow for selection of cells that survive a normally lethal condition. For example, in some genetic diseases, the disease-causing mutation causes cells to die in conditions that normal cells tolerate. By introducing a random shRNA library into the mutant cells, culturing the cells under the selective condition, and then selecting survivors, RNAi sequences that rescue the cells are identified.

Example 12

Use of the shRNA Library to Identify RNA Molecules with Ability to Induce Long-Term Proliferation of Stem Cells The cell-surface marker CD34 is known to be lost from hematopoietic stem cells, as the cells differentiate. In other experiments, these cells are infected or transfected with a random shRNA library, cultured, and then sorted for cells that retain CD34, even after cells in a control culture lose CD34 expression completely, thus enabling determination of RNAi sequences that allow the culturing of hematopoietic stem cells without differentiation. In other experiments, for confirmatory testing, another, reversible form of inhibitory RNA (e.g., siRNA synthesized in vitro) that contains the identified RNAi sequences is generated, as described in Example 9. The new form of RNAi is added to hematopoietic stem cells and shown to maintain CD34 expression in a reversible fashion Example 13

Use of the shRNA Library to Identify RNA Molecules with Ability to Sustain Pluripotency of Stem Cells In other experiments, random RNA libraries of the present invention are used to identify RNA sequences that can sustain pluripotency of stem cells. A stem cell line (e.g., LRK1 cells) is infected or transfected with a random shRNA library and incubated under conditions under which it differentiates (in the case of LRK1 cells, in the absence of IL-6), and formation of stem cell colonies is detected. The vector carried by stem cell colonies is obtained and sequenced to identify RNA sequences that can sustain pluripotency of stem cells. In other experiments, for confirmatory testing, another, reversible form of inhibitory RNA that contains the identified RNAi sequences is generated, as described in Example 9. The new form of RNAi is added to LRK1 cells and shown to maintain self-renewal and/or an undifferentiated state in a reversible fashion.

In other experiments, LRK1 cells are used to identify pluripotency-sustaining sequences using the method described by Chambers et al (Functional expression cloning of Nanog, a pluripotency sustaining factor in embryonic stem (ES) cells. Cell 113, 643-55 (2003)). LRK1 cells are transfected/infected with an RNAi library of the present invention, and self-renewing cells in the absence of cytokines are selected and pooled. shRNA sequences are then retrieved by PCR and re-ligated into the parent vector and the vectors are re-introduced into LRK1 cells one or more times, as necessary to enrich sufficiently for true positives before preparing plasmids from single, undifferentiated colonies. In other experiments, clones containing active sequences are confirmed by the formation of stem-cell colonies (which are identifiable by morphology and alkaline phosphatase staining) in the absence of cytokines.

Example 14

Use of the shRNA Library to Identify RNA Molecules with Ability to Induce Differentiation of Precursor Cells into Cell Types of Interest In other experiments, random RNA libraries of the present invention are used to identify RNA sequences that can induce differentiation of precursor cells into cell types of interest. For example, differentiation of promyeloid HL60 cells (e.g., into neutrophils), differentiation of the leukemic cell line U937 cells (e.g., into monocytes), or the differentiation of the erythroid cell line G1E is determined (e.g., into erythroid cells). Differentiation can be detected by expression of marker proteins (e.g., Ter-119 or CD11b) or by morphological criteria (e.g., adherence to plastic).

In another experiment, cells are incubated in non-differentiation media, and flow cytometry is performed for GFP and CD11b (HL60 and U937 cells) or GFP and Ter-119 (G1E cells). Cells that express both GFP (to confirm the presence of a vector) and the appropriate differentiation marker at levels higher than the highest evident in the control cells are "gated on" (selected). Differentiation of flow-sorted HL60 and U937 cells can be further confirmed by adherence of the cells to plastic. Other markers of differentiation include CD14 expression and cell morphology by Wright-Giemsa staining G1E cells form small, hemoglobinized colonies, become benzidine- and band-3-positive, and shift to a pro-normoblast morphology.

In other experiments, random RNA libraries are used to identify RNA sequences that can induce differentiation of embryonic stem (ES) cells (in other embodiment, human ES cells or murine ES cells). In other embodiments, the transfected ES cells are introduced into mice, the mice are sacrificed several weeks later, and GFP-positive cells are isolated from various tissues, then sequences associated with the cells are retrieved. The sequences play a role in differentiation of the cells into the particular cell type.

In other embodiments, differentiation of ES cells into vascular endothelial, striated muscle, myocardial, skeletal, early embryonic mesoderm, endoderm-derived, primitive endoderm (e.g., hypoblast), yolk sac visceral endoderm, ectoderm derived, neuron-like cell types, or other known cell types is detected. In other experiments, cell sorting is used to select cells that have differentiated to or toward the desired cell type. Precursor cells are infected or transfected with a random shRNA library, and fully or partially differentiated cells are isolated. The vector carried by differentiated cells is obtained and sequenced to identify RNA sequences that can induce differentiation of precursor cells into cell types of interest. In other experiments, for confirmatory testing, another, reversible form of inhibitory RNA that contains the identified RNAi sequences is generated, as described in Example 9. The new form of RNAi is added to precursor cells and shown to induce differentiation.

Example 15

Use of the shRNA Library to Identify RNA Molecules with Ability to Prevent Viral Replication or Protect Cells Against Viral Infection or Cytopathicity In other experiments, random RNA libraries of the present invention are used to identify RNA sequences that can prevent viral replication or protect cells against viral infection or cytopathicity. Primary cells or cell lines are infected or transfected with an RNAi library of the present invention then infected with a cytopathic virus (e.g., human lymphocytes and HIV-1 virus, or duck embryo fibroblast (DEF) cells and AHV-1 are utilized), then survivors are identified. In other experiments, for confirmatory testing, another, reversible form of inhibitory RNA that contains the identified RNAi sequences is generated, as described above. The new form of RNAi is added to the cells and shown to prevent viral replication or protect the cells against viral infection or cytopathicity in a reversible fashion.

Example 16

Further Improvement of RNA Molecules

To identify improvements of sequences identified after RNAi library screening described in one of the above Examples, random mutagenesis is used. In other experiments, an error-prone copying method is utilized. In another embodiment, error-prone PCR is utilized. Random mutagenesis by error-prone PCR takes advantage of the low fidelity of Taq polymerase in the presence of $Mn^{+2}$, high $Mg^{+2}$, and unequal dNTP concentrations, and is well known in the art. Because a randomly mutagenized RNAi sequence requires, under some conditions, a matched reverse complement for shRNA, iterative selection requires a recapitulation of the library synthesis protocol described in above Examples. The cell or cells in which the desired effect occurred are isolated, and using error-prone PCR, the sequence corresponding to that of the oligonucleotide at the top of FIG. 3 or FIG. 6 is amplified, e.g., by using perfectly matched primers that extend from the edge of the N28 sequence, plus one nucleotide on the downstream side (so that the 29th nucleotide in the final shRNA stem is mutagenized as well), all the way to the ends of the oligonucleotide sequence, this creates a library of "half-books."

After random mutagenesis, library construction is performed as described in one of the above Examples. The first, mismatched extension primer is, in another embodiment, an equimolar mix of four primers, each ending in a different nucleotide (complementary to the random nucleotide just downstream of the N28), (without the need for mixing four sub-libraries as done in the initial library generation), each with a different "29th" nucleotide. Although the strand of DNA complementary to the equivalent of the oligonucleotide at the top of FIG. 4 is present in the single-extension reaction, only single-extension products of the recessed, first extension primer anneal to the hairpin-loop linker.

The sub-library for a given sequence is introduced into target cells as described in one of the above Examples, except that the original sequence is included among the controls. In some experiments, increased effectiveness of an shRNA construct in this context is defined as (1) a larger number of surviving cells under the original conditions used for selection, (2) longer survival under the original conditions used for selection, or (3) survival under more stringent conditions. For initially identified RNA molecules that show subtle improvement over the control shRNAs (such as survival for slightly longer under the original conditions used for selection), the second criterion will likely be the most important for selecting more effective sequences. For RNA molecules that rescue cells for extended periods in the initial confirmatory assay, the third criterion will be the most important for selecting more effective sequences; for such sequences, more stringent conditions are tested to establish new minimum conditions for 100% loss of viability.

In other experiments, the entire gene encoding the RNAi molecule of the present invention (i.e. both halves of the double-stranded region, and the intervening region; or "whole books") is copied by a low-fidelity method, then the sub-library of whole-books is inserted or subcloned into an expression vector, etc, and the resulting sub-library is introduced into target cells as described for the above method.

In other experiments, for HL60, U937, and G1E cells, increased effectiveness of an shRNA construct is defined as higher expression of differentiation markers, a larger number of cells expressing differentiation markers, or expression of a wider range of differentiation markers. For LRK1 cells, increased effectiveness of an shRNA construct is defined as a larger number of undifferentiated colonies, or maintenance of undifferentiated cells over more passages.

In other experiments, cells infected or transfected with vectors encoding the RNA molecules are followed and compared closely by microscopic examination to cells infected or transfected with the sub-library for that sequence. In another embodiment, sequences identified are retrieved by PCR. In another embodiment, the correctness and activity of the sequences is confirmed by re-introduction into cells, as described above.

Example 17

Use of RNA Molecules to Identify Drug Targets for Disease States and Stem Cell Applications In another embodiment, improved sequences implicate individual genes, which in turn suggest potential drug targets. Candidate genes are identified by homology searching the human genome database (with the first 22 nt of improved sequences in particular). Candidate genes are confirmed by using independent shRNAs targeting different mRNA sequences from the same gene. Additional confirmation is performed by Western analysis, Northern analysis, and/or quantitative RT-PCR, in comparison with control shRNAs to rule out non-specific effects. Optional, final confirmation involves reversing the phenotype (rescue from oxidant stress, for example) by re-expressing the target gene with mutations that abrogate the shRNA effect but do not change the encoded amino acids.

In other experiments, improved sequences implicate multiple target genes, which are confirmed by microarray analyses.

Materials and Methods (Examples 18-20)

Random Mutagenesis

A 132-mer oligo, which can form an internal partial hairpin, was synthesized by ChemGenes (FIG. 13A):
5'CCCTATATGCATGCTGAGGAAGAATTCAGCGG-
CCGCGATGACCTGAAA*A*A*N*N*NNNNNNN-
NNNNNNNNNNNNNNNNNNNGGTTTAAACAGGT-
GAGAATTCTATTCAGTCATAGAATTCTCACCTGCT-
TAAAGC-3' (SEQ ID NO: 161). The asterisks represent thio-ester bonds. The details of the three mutagenesis steps illustrated in FIG. 13A are shown below. The individual dNTPs are from Denville Scientific, and all buffers and enzymes are from New England Biolabs. Numbers listed in the steps below represent microliters unless indicated otherwise. Minus signs after nucleotides indicate that they are dropped out of the indicated extension mix.

Step 1:

|  | A- | C- | G- | T- |
|---|---|---|---|---|
| 132-mer (0.1 nmole/μL) | 1 | 1 | 1 | 1 |
| Water | 14.5 | 14.5 | 14.5 | 14.5 |
| dATP (100 mM) | — | 0.5 | 0.5 | 0.5 |
| dCTP (100 mM) | 0.5 | — | 0.5 | 0.5 |
| dGTP (100 mM) | 0.5 | 0.5 | — | 0.5 |
| dTTP (100 mM) | 0.5 | 0.5 | 0.5 | — |

Boil 3 min, quick spin. cool to 37° C.

| | | | | |
|---|---|---|---|---|
| NEB Buffer 2 | 2 | 2 | 2 | 2 |
| Klenow (exo–) (5 U/μL) | 1 | 1 | 1 | 1 |

37° C. × 30 min, followed by ethanol precipitation of DNA.

Step 2:

|  | A- | C- | G- | T- |
|---|---|---|---|---|

Mix components below first to a total volume of 95 μL, and use the mix to resuspend the DNA pellet from step 1.

| | | | | |
|---|---|---|---|---|
| Water | 82 | 82 | 82 | 82 |
| NEB RTase buffer | 10 | 10 | 10 | 10 |

Adjust each stock concentration such that when 1 μL is used, final concentrations are:

| | | | | |
|---|---|---|---|---|
| dATP | — | 1 mM | 0.1 mM | 0.5 mM |
| dCTP | 1 mM | — | 1 mM | 0.5 mM |
| dGTP | 0.01 mM | 0.2 mM | — | 1 mM |
| dTTP | 1 mM | 0.002 mM | 0.2 mM | — |

After resuspending pellet, add M-MuLV reverse transcriptase (RTase, NEB, 200 U/μl)

| | | | | |
|---|---|---|---|---|
| RTase volume | 2.5 | 2.5 + 2.5 | 2.5 + 2.5 | 2.5 + 2.5 |
| RTase incubation at 42 C. | 1 hr | 2 + 2 hr | 1 + 1 hr | 1 + 1 hr |

2.5+2.5/2+2 hr means that 2.5 μL of RTase is incubated for 2 hrs at 42° C. and another fresh 2.5 μL is added for another 2 hrs at 42° C. DNA is again ethanol precipitated.

Step 3:

|  | A- | C- | G- | T- |
|---|---|---|---|---|

Mix components below first for a total volume of 50 μL, and use that mix to resuspend the DNA pellet from step 2.

| | | | | |
|---|---|---|---|---|
| Water | 41 | 41 | 41 | 41 |
| dNTP (10 mM each) | 2 | 2 | 2 | 2 |
| NEB Buffer 2 | 5 | 5 | 5 | 5 |
| Klenow (exo–) (5 U/μL) | 2 | 2 | 2 | 2 |

37° C. for 30 min.

The remainder of the library synthesis is carried out as described in the making of the non-mismatch library. As in that library, the current oligo has a G at the end of the N29 random segment (i.e., the segment is N28+G), representing ¼ of the complete, random N29 library that can be made similarly using N28+A, N28+C, and N28+T.

Cell Culture, Retroviral Transduction

The FL5.12 pro-B cell line was a gift from Dr. Craig Thompson (Memorial Sloan-Kettering Cancer Center). FL5.12 cells were cultured in RPMI 1640 media with 10% FBS (Thermo Scientific), 10 mM Hepes pH 7.4, 100 U/mL Penicillin, 100 mg/mL Streptomycin, 55 mM β-Mercaptoethanol (all from Gibco), supplemented with 0.6 ng/mL IL3 (BD Pharmingen). To prepare retroviral supernatant for infection, 293T cells at ~70% confluency were transfected with Effectene reagent (Qiagen) according to manufacturer's instructions. The pSiren (Clontech) library was co-transfected with an ecotropic retroviral packaging plasmid pCL-Eco (Imgenex) at a dose of 2.5 μg total DNA per well in a 6-well plate. Supernatant was harvested to infect FL5.12 cells with 3 cycles of centrifugation (2500 g for 45 minutes) and incubation (2 hrs), in the presence of 5 μg/mL polybrene (Sigma). Infection efficiency was monitored by mCherry expression on a BD LSRII flow cytometer. Ideally the mCherry percent positivity was kept at ~33% or less whenever a library was used to transduce cells, so that, by Poisson distribution, the majority of the infected cells received only one construct.

Sequence Enrichment

To enrich for sequences that support cell survival during IL3 withdrawal, infected cells were subjected to cycles of IL3 withdrawal and recovery. In each cycle, apoptosis was induced in FL5.12 cells by washing three times with IL3-negative medium and resuspending in IL3-negative medium. After 72 or 96 hours cells were resuspended in medium containing IL3 to recover. No attempts were made to get rid of dead cells during this process. The cycling was repeated until the mCherry or GFP percentage of the FL5.12-cell population enriched to at least 2-fold higher than the post-infection percentage.

Sequence Retrieval

To retrieve shRNA-encoding sequences, cells that have been enriched for mCherry after IL3 starvation/recovery cycles were pelleted, and their genomic DNA was extracted using QIAamp® DNA Mini Kit (Qiagen). The shRNA-encoding cassette was amplified from genomic DNA using the following protocol: 95° C. for 5 min, 95° C./56° C./72° C. at 30 s/45 s/2 min for 30 cycles, and 72° C.×10 min, using Vent® exo-DNA polymerase (NEB) and 6 mM MgSO$_4$ with primers flanking the shRNA-encoding cassette on the vector pSiren. The sequences of the primers are 5'-CCGGAATT-GAAGATCTGGG-3' (SEQ ID NO: 162) and 5'-CCGTAAT-TGATTACTATTAATAACTAGAATTC-3' (SEQ ID NO: 163). Products amplified by Vent were subject to another round of amplification using fresh dNTPs and Bst DNA polymerase (NEB) by using the following protocol: before adding Bst, 95° C. for 5 min, 65° C. for 30 s; add Bst, 65° C. for 30 min Retrieved sequences were digested with Bgl II and EcoR I, and ligated into pSiren (GFP).

Hit Confirmation

Individual clones retrieved as described above were tested in FL5.12 cells for their ability to protect against IL3 withdrawal, against control, and against previous hit sequences (all in pSiren/GFP). Apoptosis was induced by washing three times with IL3-negative medium and resuspending in IL3-negative medium. Tests of individual clones were carried out with an overnight IL3 starvation of 22-26 hours. Cells were then stained with 10 nM To-Pro-3 iodide (Invitrogen). The percentage of GFP-positive (infected) and To-Pro-3-negative (live) cells relative to the start of the experiment (just prior to the IL3 withdrawal) were determined by flow cytometry on a BD FACSCalibur. Confirmed hits were then sequenced using the PCR primers.

Statistical Analysis

Pair-wise comparisons of means were conducted using Student's t-test. Error bars represent standard deviations. The data points for each bar graph were determined from 3 to 4 independent experiments.

Example 18

Library Synthesis

Our library design precludes methods of random mutagenesis based on PCR. Non-PCR methods that have been described include chemical mutagenesis of bases, with ethyl methane sulfonate (EMS), nitrous acid, formic acid, or hydrazine. Other methods use so-called "universal bases," such as inosine or novel synthetic bases, capable of pairing with any of the natural bases. However, the pairing preferences of these bases for the natural bases have never been optimal. Furthermore, all of the described methods are based on mutagenesis of a known, fixed sequence, whereas our target is completely random. Based on these aforementioned methods, multiple attempts to mutagenize random target sequences, in the context of our library synthesis procedure, were unsuccessful (data not shown).

Our eventual approach was based on the work of Lehtovaara et. al. ((1988) *Protein Eng* 2: 63-68)(Materials and Methods, FIG. 13A). Briefly, the first step involves four independent DNA-polymerase extension reactions, with each extension lacking one of the four deoxyribonucleotide triphosphates (dNTPs). FIG. 13A depicts the extension reaction lacking dGTP; theoretically, the polymerase should stall at the first template base whose complementary dNTP is missing, in this case at "C." The second step uses an error-prone polymerase to forcefully incorporate the wrong base where the initial polymerase stalled; the concentrations of the other three dNTPs are included at ratios that compensate for their differential pairing affinity with the template base. (The depiction of the second step in FIG. 13A is only schematic since it shows the same template generating three differently stalled extension reactions; however, the number of possible random 29-mer templates—$4^{29}$—mathematically precludes the chance of the same template being present twice at the reaction scale we used, hence in actuality each template can be mutagenized only once.) The third step is a final extension reaction with all four dNTPs.

The rest of the library synthesis is shown schematically in FIG. 13B. Each clone comprises a 29-nucleotide random sequence and its reverse complement in the same strand of DNA, separated by a non-complementary loop sequence (5'-CTAAAC-3'). In addition to the introduction of random mismatches between the two halves of the stem-encoding sequences, we increased the complexity of our second-generation library by 10-fold, from 300,000 clones in our first-generation library to 3 million clones. The fluorescent reporter was changed from Green Fluorescent Protein (GFP) to the Red Fluorescent Protein mCherry, which allows our library to be used with GFP reporter constructs in gene-activation screens.

Example 19

Library Characterization 50 random clones from our second-generation library were sequenced (Table 1).

TABLE 1

5'-TAAGCTAGAAAACGCGTGCGGAGCCTTAG CTAAAC-3'
(SEQ ID No: 54)
3'-ATTCGATCTTTTGCGCACGCCTCGGGATC -5'
(SEQ ID No: 55)

5'-TGTGTGGACAGAAACTGGGAGGGTTGCAG CTAAAC-3'
(SEQ ID No: 56)
3'-ACACACCTGTCTTTGACCCTCCCAACGTC -5'
(SEQ ID No: 57)

5'-CCTAACAATGATCTTCATTGTCTTCGTGG CTAAAC-3'
(SEQ ID No: 58)
3'-GGATTGTTACTAGAAGTATCAGAAGCACC -5'
(SEQ ID No: 59)

5'-TTAGATAATGGTTTCAAAATGATTTATTG CTAAAC-3'
(SEQ ID No: 60)
3'-GATCTGTTACCGAAGTTTTACTAAATAAC -5'
(SEQ ID No: 61)

5'-TGGGAGGGATACAAATAACACTACCCCCG CTAAAC-3'
(SEQ ID No: 62)
3'-ACCCTCCCCATGTCTACTGCGATCGGGGC -5'
(SEQ ID No: 63)

5'-TGGCTCGTACGGACATAAGCAAGGAGTGG CTAAAC-3'
(SEQ ID No: 64)
3'-ACCGAGCATGCCTGTATTCGTTCCTCACC -5'
(SEQ ID No: 65)

5'-TATCTTGCTTGTTTATTGTGTAGAATG CTAAAC-3'
(SEQ ID No: 66)
3'-GATAGAACGGACGAATAGCACATCTTAC -5'
(SEQ ID No: 67)

5'-TTTGTTGTGATCTGGCTTAATCCGCTTGG CTAAAC-3'
(SEQ ID No: 68)
3'-AAACAACACTAGACCGAATTAGGCGAACC -5'
(SEQ ID No: 69)

TABLE 1-continued

5'-<u>TATACCGTGGGGCTCTATTTGGACCTGG CTAAAC</u>-3'
(SEQ ID No: 70)
3'-<u>CGCTCGTACGGTACAGACGGAATTGGAAC</u> -5'
(SEQ ID No: 71)

5'-GCCCTCGAATAATTGATATCTGTTGATG CTAAAC-3'
(SEQ ID No: 72)
3'-CCGGGAGCTGATTAACTATGGACAACTAC -5'
(SEQ ID No: 73)

5'-GCCATGGCTTGCATACGCGAGTGGGAG-- CTAAAC-3'
(SEQ ID No: 74)
3'-CGGTACCGAACGTATGCGCGCACCCTCGC -5'
(SEQ ID No: 75)

5'-TATGTAGGTTAATGTTTGGTTTGGATGAG CTAAAC-3'
(SEQ ID No: 76)
3'-GTACGTCCAATTGCAAGCCAAGCCTACTC -5'
(SEQ ID No: 77)

5'-CTACGTTAGGTTATCCTTGTTGTTTGGGG CTAAAC-3'
(SEQ ID No: 78)
3'-GATGCAATCTAATAGGAACATCAAACCCC -5'
(SEQ ID No: 79)

5'-GACCGGACTTATTGTCTGGTCCAAATTCG CTAAAC-3'
(SEQ ID No: 80)
3'-CTGGCCTGAATAACAGACCACGTTTAAGC -5'
(SEQ ID No: 81)

5'-TACATTTACTGCCTTACTCTATGCTGCGG CTAAAC-3'
(SEQ ID No: 82)
3'-ATGTAAATGACGGAATGAGATACGACGCC -5'
(SEQ ID No: 83)

5'-<u>ATAGATTGGACAAAACTTAATCAACCCTG CTAAAC</u>-3'
(SEQ ID No: 84)
3'-<u>CCTAGCTTCTTGCACGCCACGTCACTCCTCC</u> -5'
(SEQ ID No: 85)

5'-GCTGATCATAATGTGTAAAATCCTCTAG CTAAAC-3'
(SEQ ID No: 86)
3'-GCGACTAGTATTACACAT-CTCGGACATC -5'
(SEQ ID No: 87)

5'-CCTGCTTTTTATTCCGCGCTCTGGTG-GG CTAAAC-3'
(SEQ ID No: 88)
3'-GGACGAAAAATAAGGCGCGAGACCACAGC -5'
(SEQ ID No: 89)

5'-GTCAGGGCTGT---AAATAGTTTATAGTGG C-AAA-3'
(SEQ ID No: 90)
3'-CAGTCCCGACAGGGTTTATCAAAGATCAC -5'
(SEQ ID No: 91)

5'-TGGCTCCAGAAACCAGCCCCTCCTTATG CTAAAC-3'
(SEQ ID No: 92)
3'-GACCGAGGTCTTTGGTCGCCGAGGAATAC -5'
(SEQ ID No: 93)

5'-CCTGCTTTTTATTCCGCGCTCTGGTGG-G CTAAAC-3'
(SEQ ID No: 94)
3'-GGACGAAAAATAAGGCGCGAGACCACAGC-5'
(SEQ ID No: 95)

5'-TAAAGGCATCGATGGAGATTTCGCGAAGG <u>CTAAAC</u>-3'
(SEQ ID No: 96)
3'-ATTTCCGTAGCTACCTCTAAAGCGCTTCC-5'
(SEQ ID No: 97)

5'-TCCACGGGCCGCTACAGTCCCTT--ATG CTAAAC-3'
(SEQ ID No: 98)
3'-AGGTGTCCGGCGATGTCAGGGAATCTAC-5'
(SEQ ID No: 99)

5'-TATTTTCCGTGGGTGCCGAATCCGATATG CTAAAC-3'
(SEQ ID No: 100)
3'-ATAAAAGGCACCCACGGCTTAGGCTGTAC-5'
(SEQ ID No: 101)

5'-CATTGATGAGATTGGTGGAGTTATTTTTG CTAAAC-3'
(SEQ ID No: 102)
3'-GTAGCTACTCTAGCCACCTCAGTGAAAAC-5'
(SEQ ID No: 103)

5'-GTGTGCTGGGGCTAATGCCTCGCCGGGCG CTAAC-3'
(SEQ ID No: 104)
3'-CACACGACCCTGATTACGGTGCGGCCCGC-5'
(SEQ ID No: 105)

5'-TGACCACACCTTCATCCCTCATCCCTGG CTAAAC-3'
(SEQ ID No: 106)
3'-CACTGGTGTGGAAGTAGGGAGTAGGGACC-5'
(SEQ ID No: 107)

5'-ATATTGGGGAAAGCTGGGATGGACTATTG GTAAAC-3'
(SEQ ID No: 108)
3'-TTAAGTCCCTTTCGACCCTACCTGATAAC-5'
(SEQ ID No: 109)

5'-TGCCAGGTTAGAGCGCAAAAGTTCGAACGG CTAAAC-3'
(SEQ ID No: 110)
3'-TAGG-CCAATCTCGCGTTTTCAAGCTTGC-5'
(SEQ ID No: 111)

5'-CGTTTGAGTGGTGTGGTAGGTGTGTTGGG CTAAAC-3'
(SEQ ID No: 112)
3'-GCGAGCTCACCACGCCATCCACGCAACCC-5'
(SEQ ID No: 113)

5'-TACGTTAGGTTATCCTTGTTGTTTGGGG CTAAAC-3'
(SEQ ID No: 114)
3'-GATGCAATCTAATAGGAACATCAAACCCC-5'
(SEQ ID No: 115)

5'-<u>TCAATTTACGGTCGTGCTGTAGAGAACCG CTAAAC</u>-3'
(SEQ ID No: 116)
3'-<u>GGCCCAAGGCTCCTTCCACCAAAGATTGC</u>-5'
(SEQ ID No: 117)

5'-CTGAGTCAATGCGCTATTTAAGGAGGATG CTAAAC-3'
(SEQ ID No: 118)
3'-GACTCAGTTACGCGGTAAGTTCCTCCTAC-5'
(SEQ ID No: 119)

5'--CAGTAGTCCAGTGTACCACTAAGTGAAG CTAAAC-3'
(SEQ ID No: 120)
3'-GGTCATCAGGTCACATGGTGGTTCACTTC-5'
(SEQ ID No: 121)

5'-CGAGGGAATCGGCCACTGTGCTGGTC--G CTAAAC-3'
(SEQ ID No: 122)
3'-GCTCCCTTAGCCGGTGACACGACCAGTGC-5'
(SEQ ID No: 123)

5'-CGGATCACCAGGCGTTTGAGTCCTAGCG CTAAAC-3'
(SEQ ID No: 124)
3'-GGCTAGTGGTCCGCAAACTCAGGATCGC-5'
(SEQ ID No: 125)

5'-GCGTGCCATCTTGTTGGATAGAATTTGG CTAAAC-3'
(SEQ ID No: 126)
3'-CCGCACGGTAGGACAACCTATCTTAGACC-5'
(SEQ ID No: 127)

5'-GTCACTCGGGGTTTCTTTCTGTCTTATAG CTAAAC-3'
(SEQ ID No: 128)
3'-CAGTGAGCCCCAAAGAAAGACAGACTATC-5'
(SEQ ID No: 129)

5'-ACACACGGCCTTTGCACGGTTGGTAGAG CTAAAC-3'
(SEQ ID No: 130)
3'-GTGTGTGCCGGAAACGTGCGGACCATCTC-5'
(SEQ ID No: 131)

5'-CGGTAGACCTAGGGGAGCCGTCGATCTAG CTAAAC-3'
(SEQ ID No: 132)
3'-GCCATCTGGATCCCCTCGGCAGCTAGATC-5'
(SEQ ID No: 133)

TABLE 1-continued

```
5'-TTGGTCCATCATTCGCGTTCATGTTGGGG CTAAAC-3'
(SEQ ID No: 134)
3'-AACCAGGTAGTAAGCGCAAGTACAACGCC-5'
(SEQ ID No: 135)

5'-TCAGCCATGCGTGCGTTGGGGCTTGTACG CTAAAC-3'
(SEQ ID No: 136)
3'-AGTCGGGACACACGCAACCCCGAACATGC-5'
(SEQ ID No: 137)

5'-GGTAGACCTAGGGGAGCCGTCGATCTAG CTAAAC-3'
(SEQ ID No: 138)
3'-GCCATCTGGATCCCCTCGGCAGCTAGATC-3'
(SEQ ID No: 139)

5'-AAGGCATGGTTTGTTCGACTTTGCCCTCTGG C-AAAC-3'
(SEQ ID No: 140)
3'-TTC-GTACCAAACTAGCTGAATCGGGAGAC-5'
(SEQ ID No: 141)

5'-GGTTTCTGTCGCGTGCTGTTATATAATG CTAAC-3'
(SEQ ID No: 142)
3'-CCAAAGACAGCGCACGGCAATATATTAC-5'
(SEQ ID No: 143)

5'-CGGTAGACCTAGGGGAGCCGTCGATCTAG CTAAAC-3'
(SEQ ID No: 144)
3'-GCCATCTGGATCCCCTCGGCAGCTAGATC-5'
(SEQ ID No: 145)

5'-TAGGAGCGTTCGGCCTTACGGTGTTATGG CTAAAC-3'
(SEQ ID No: 146)
3'-ATCCTCGCTAGCCGGTTTGCCACAATACC-5'
(SEQ ID No: 147)

5'-CACGGGCTGATCGTAAGTGACTGGTCAG CTAAAC-3'
(SEQ ID No: 148)
3'-GTGCCCGACTAGCATTCACTGACCAGTC-5'
(SEQ ID No: 149)

5'-ACTATCAAGGGGCTTGTGGGACAAGAG CTAAAC-3'
(SEQ ID No: 150)
3'-TGATAGTTCCCCGAACACCCCTGTTCTC-5'
(SEQ ID No: 153)

5'-CGCGCATGGATGCCCGGTATGGATTTACG CTAAAC-3'
(SEQ ID No: 154)
3'-GCGCGTACCTACGGGCCATACCTAAATGC-5'
(SEQ ID No: 155)
```

Thirty-five (70%) have mismatches (shown in bold) between the two halves of the stem, 12 (24%) lack mismatches, and three (6%) have (essentially) non-complementary halves (underlined) and would not be expected to encode shRNAs or form a hairpin structure. (Of the many clones sequenced from the first-generation library, clones with non-complementary halves were never observed.) Among the different types of mismatches, T-G is the most common, even with the intentional skewing of the three dNTPs in step 2 (Table 2).

Unexpected deletions were observed (e.g., clones 11 (SEQ ID NOs: 74-75), 17-19 (SEQ ID NOs: 86-91), 21 (SEQ ID NOs: 94-95), as well as deletions/mutations occurring in the loop sequence (clone 19 (SEQ ID NOs: 90-11), 28 (SEQ ID NO: 108-109), 44 (SEQ ID NOs: 140-141)). Also, some clones "skipped" mutations where we would have expected them to occur. Based on FIG. 13, the method should introduce mutations starting with the first available G, and potentially every following G (depending on the length of incubation with the reverse transcriptase). However, this rule was not always followed. For example, in clone 4 (SEQ ID NOs: 60-61), the first template G in the extension reaction was matched with a C, whereas the following Gs were mismatched with Ts, as expected. In clone 13 (SEQ ID NOs: 78-79), a T-A match is flanked by two mismatches (T-G and T-T).

The library was designed to encode 29-bp stems. Both the first- and second-generation libraries contain occasional clones with 28- and 30-bp stems, probably due to 1-nt errors in the length of the original template oligo. Both libraries also contain occasional clones with 28-nt-29-nt stems, probably due to the inherent imprecision of the downstream-cutting enzyme BtgZ I in one of the initial steps of the library synthesis. Assuming that most of the mismatches and deletions arose from the mutagenesis process in the construction of our second-generation library (and not from the original oligo template), ~80 mistakes in ~1400 positions from 50 clones sequenced were observed, leading to an estimated mutation rate of ~5.7%.

Example 20

Library Validation

As with the first-generation library, the second-generation library was validated by packaging the library as retroviruses and screening for shRNAs that protect the IL3-dependent, murine pro-B cell line FL5.12 from IL3 withdrawal. After 2-3 days in the absence of IL3, ~100% of FL5.12 cells die by apoptosis; if Bcl-xL is expressed, >90% of the cells are rescued. To minimize the chance that a weak hit sequence would be diluted by inactive shRNAs, we aimed to achieve 30% infectivity, thereby ensuring that most cells would express only one shRNA. Consistently lower infectivity with mCherry vectors than with GFP vectors suggested that mCherry is slightly more toxic to FL5.12 cells. In the end, ~150 million FL5.12 cells were infected to ~6% mCherry positivity (~9 million infected cells), ensuring adequate coverage of the three-million-clone, second-generation library. Cells infected to ~10% mCherry positivity with a single, randomly selected shRNA were used as a control.

Figure 13:
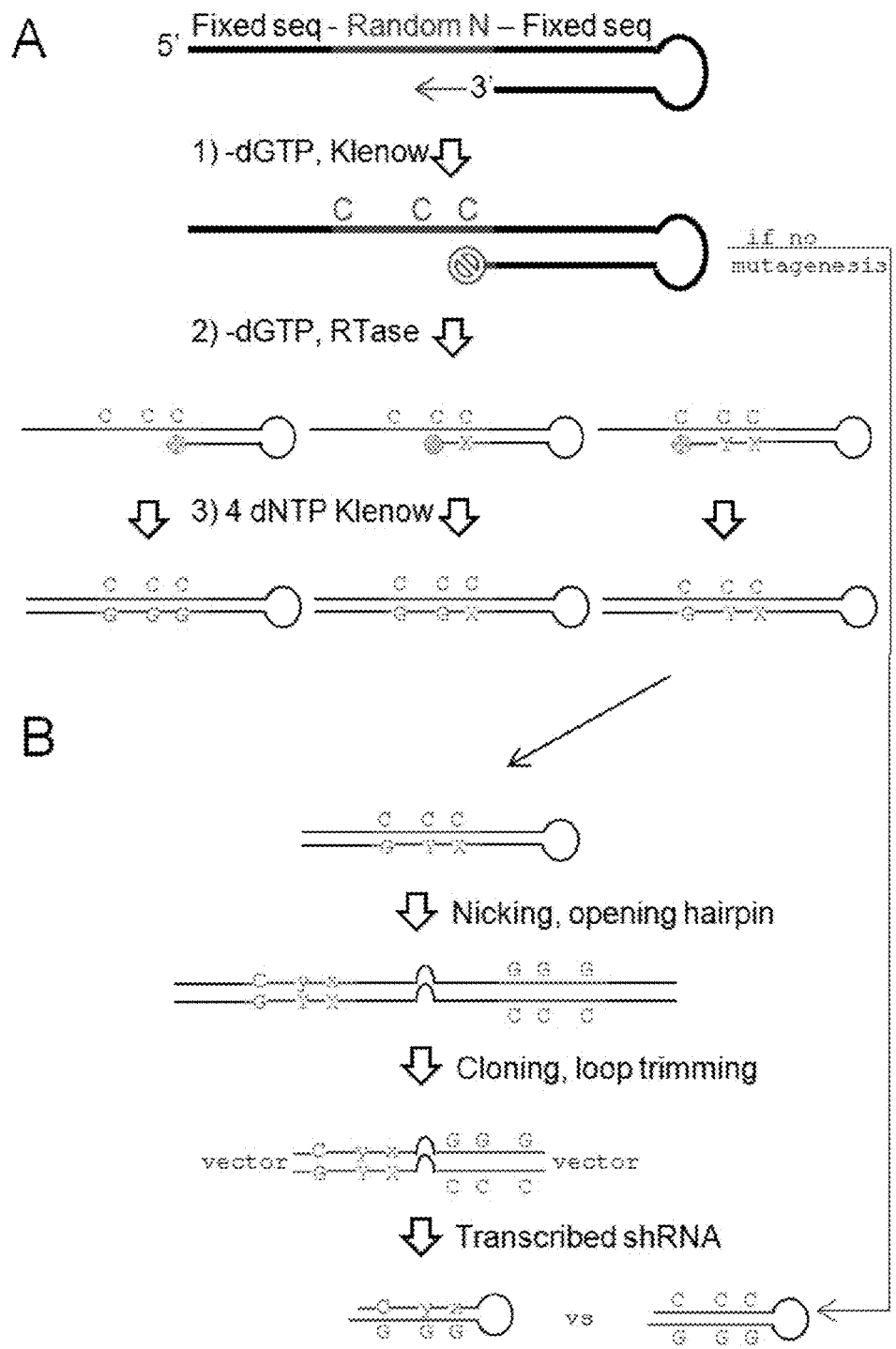
FIG. 13. Shows the introduction of mismatches by random mutagenesis. (A) Three steps were used to introduce mutations into the random template. Step 1: Extension reaction, minus one of the four dNTPs; in this example, minus dGTP. The extension should in theory stop at the first C. Step 2: Error prone reverse transcription forcefully incorporate a mismatched base opposite the C, still minus dGTP, but with different ratios of dATP, dCTP, and dTTP to compensate for their different paring affinities with C. Depending on the length of incubation, different lengths of stalled fragments will result. Step 3: After mutations are introduced, the extension reaction is completed with all four dNTPs present. (B) Abbreviated depiction of the rest of the library synthesis. Briefly the (single-stranded) DNA is nicked near the 5' end, the hairpin is opened with an extension reaction using a strand-displacing polymerase, the ends are digested for cloning, the loop is digested asymmetrically and re-ligated to form a final loop sequence of 6 nucleotides (5'-CTAAAC'-3). For comparison, a non-mutagenized hairpin is also shown.
Figure 14:
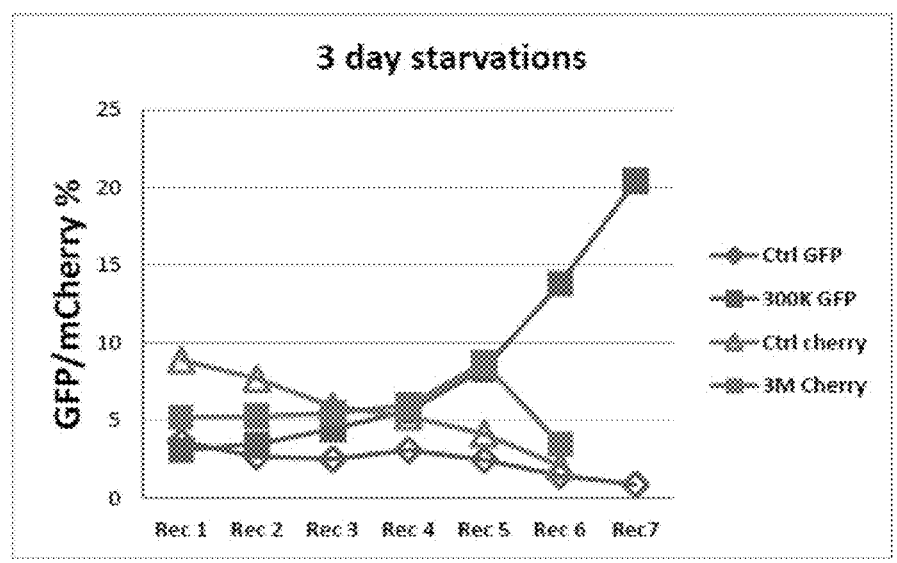
FIG. 14. GFP and mCherry percentage after IL3 starvation/recovery cycles. FL5.12 cells were screened side-by-side with transduction of the first-generation (300K GFP) or second-generation (3M mCherry) library, along with the corresponding control shRNA. Cells were subject to IL3-withdrawal of three days (A) or four days (B). GFP or mCherry percentages after each recovery (Rec) are shown.
Figure 14:
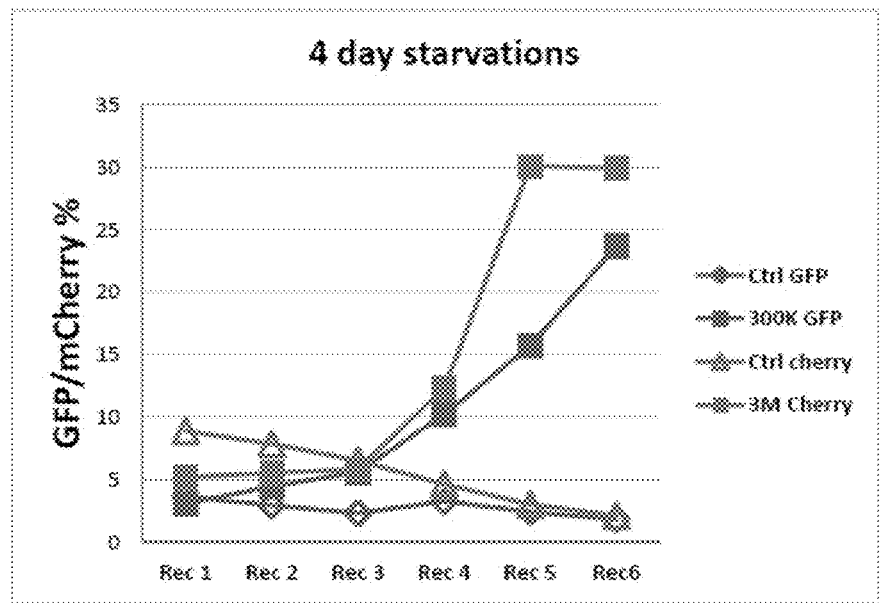

To compare the first- and second-generation libraries directly, we screened both libraries, side by side. True positives were enriched for by subjecting the cells infected with our second-generation library to repeated withdrawal from IL3 for three days, followed by recovery (Materials and Methods). Whereas previous hit sequences from the first-generation library were isolated by withdrawing IL3 for three days per cycle, the side-by-side comparison screens were performed using both three-day and four-day withdrawals from IL3, having hypothesized that the mismatches introduced into the second-generation library would increase biological activity. As expected with the presence of hit shRNAs, the percentage of fluorophore-positive cells started to increase after 3-4 cycles in all four arms of the experiment (FIG. 13). In both the three-day- and four-day-cycle experiments with the second-generation library, the mCherry percentage stopped increasing in later cycles (FIG. 13), most likely due to the emergence of mCherry-negative, IL3-independent clones.

Figure 15A:
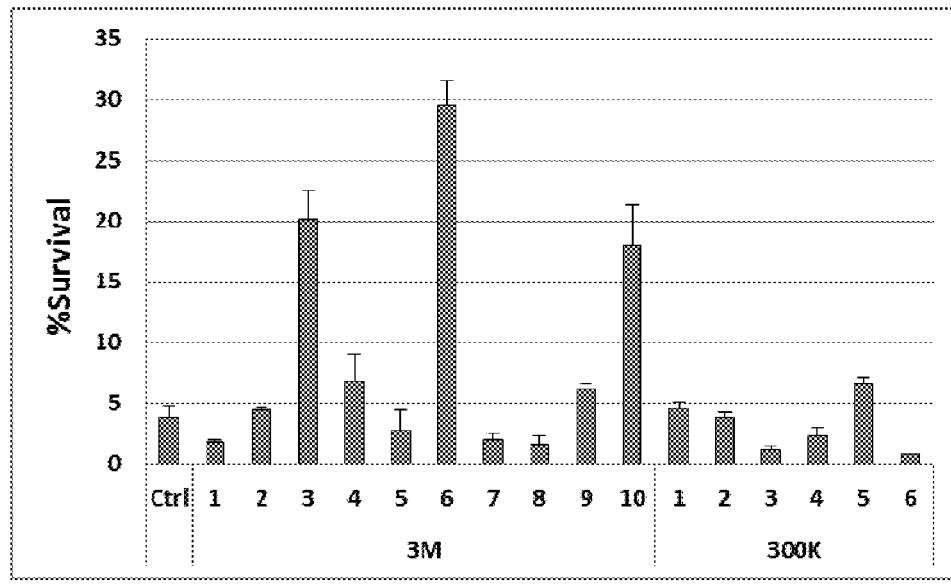
FIG. 15. shRNAs selected from the second-generation library better protect FL5.12 cells from IL3 withdrawal. (A) FL5.12 cells were transduced with different shRNA clones isolated from the side-by-side screens of the first-generation (300K) and second-generation (3M) libraries. The cells were subjected to an overnight IL3 withdrawal. Survival percentages (percentages of GFP+/To-Pro-3-cells) are shown, relative to the beginning of IL3 starvation. The six clones offering the most protection, relative to a control shRNA, were clones 3M-3 ($p<0.0001$), 3M-4 ($p=0.10$), 3M-6 ($p<0.0001$), 3M-9 ($p=0.019$), 3M-10 ($p<0.0001$) and 300K-5 ($p=0.011$). Three clones from the second-generation library (3M-3, -6, and -10) were all significantly more protective than clone 300K-5 ($p<0.0001$ for all three). (B) Clones 3M-3, -6, and -10 were compared to two hit shRNAs (1p and 3p) isolated in our previous study from the first-generation library. The improved survival was highly statistically significant, with $p<0.0001$ by Student's t-test in pair-wise comparisons between any of the three clones (3M-3, -6, or -10) versus either 1p or 3p. (C) Sequences of clones 3M-3, -6, and -10 from the second-generation, mismatched library, and of clones 1p, 3p and 300K-5 from the first-generation, non-mismatched library.
Figure 15B:
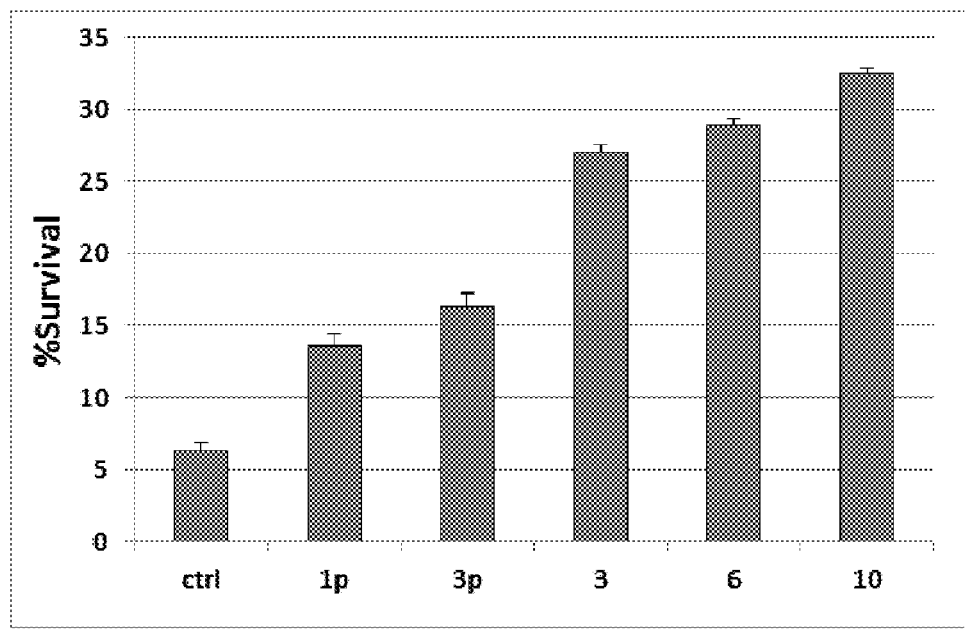

After five cycles of IL3 withdrawal and recovery, we isolated genomic DNA, amplified the shRNA-encoding cassettes by PCR, and cloned back into pSiren/GFP. Selected clones were tested individually against a control random shRNA, as well as against hit sequences identified previously from the first-generation library (clones "1p" and "3p"), all in the context of GFP. Clones 1p and 3p doubled survival, as reported previously, while three of the new clones, 3, 8 and 12, were significantly more protective than 1p or 3p, quadrupling and quintupling survival relative to the random control clone (FIG. 15B). Other clones were more protective than control, but less protective than 1p or 3p (data not shown). The sequences of clones 3, 8, and 12 are shown in FIG. 15C, alongside the sequences of 1p and 3p.

Figure 16:
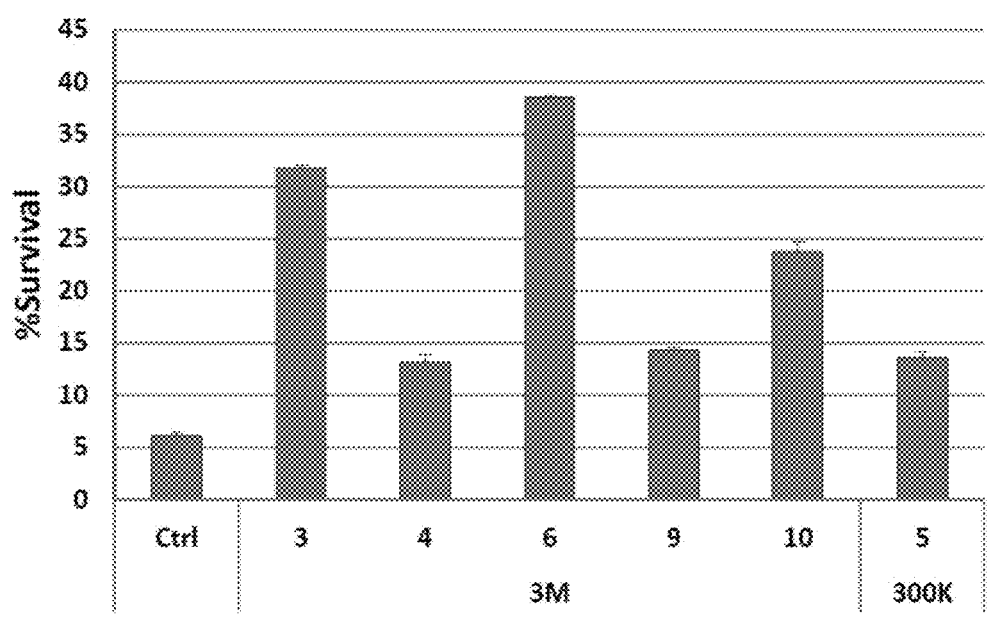
FIG. 16. shRNAs selected from the second-generation library better protect FL5.12 cells from IL3 withdrawal. FL5.12 cells were transduced with different shRNA clones obtained from the side-by-side screen. The cells were subject to an overnight IL3 withdrawal. Survival percentages (percentages of GFP+/To-Pro-3-cells) are shown, relative to the beginning of IL3 starvation. All six clones, five from the second-generation (3M) library and one from the first-generation (300K) library were significantly more protective than control ($p<0.0001$ for all). Clones 3M-3, -6, and -10 were also significantly more protective than clone 300K-5 ($p<0.001$ for all).

Cells were harvested at their respective peak percentages of fluorophore-positive cells, genomic DNA was isolated, the shRNA-encoding cassettes were amplified by PCR, and were cloned back into pSiren/GFP. Randomly selected clones enriched from both the first- and second-generation libraries were tested side-by-side against a control random shRNA (FIG. 15A). Of the six clones tested from the first-generation library, only one was active (and only slightly) in protecting the cells from IL3 withdrawal, whereas of the 10 clones tested from the second-generation library, two were slightly active and three were highly active (FIG. 15A). The active clones from both libraries were tested again and similar results were obtained (FIG. 16). The three highly active hit clones from the second-generation library were also tested against the most active hit clones isolated from the first-generation library (clones "1p" and "3p"), and all three of the clones from the second-generation library were significantly more active (FIG. 15B), though their relative activities varied somewhat from experiment to experiment (FIG. 15A, FIG. 15B, and data not shown). However, these three clones consistently offered an approximately four-to-five-fold survival advantage relative to a random control clone, whereas hit clones from the first-generation library, as described in Example 7 above and from the present side-by-side comparison, offered an approximately two-fold survival advantage. The sequences of the three highly active clones are shown in FIG. 15C, alongside the sequences of 1p, 3p and the slightly active clone from the direct-comparison screen with the first-generation library.

TABLE 2

List of mismatches from the 50 clones sequenced from the three-million-clone, second-generation library.

| Mismatch (descending order) | Total | % |
|---|---|---|
| TG | 30 | 45 |
| TT | 10 | 15 |
| AC | 5 | 7.5 |
| GT | 5 | 7.5 |
| AG | 4 | 6 |
| GG | 4 | 6 |
| CC | 3 | 4.5 |
| TC | 2 | 3 |
| AA | 1 | 1.5 |
| GA | 1 | 1.5 |
| CA | 1 | 1.5 |
| CT | 0 | 0 |

Of the more than 20 clones retrieved after biologic selection and PCR retrieval, all of them had mismatches between the two halves of the stem, whereas the mismatch percentage in 50 sequenced clones from the library itself was ~70%, again consistent with the hypothesis that the introduction of mismatches increased potency and/or retrieval efficiency. In parallel with the selection described above, the same selection was repeated with the first-generation library, with both three-day and four-day cycles of IL3-withdrawal, and clones after GFP-positivity increased significantly were retrieved. Some of these clones protected FL5.12 cells from IL3 withdrawal better than a random control clone, but none were more protective than 1p. Among all the hit sequences identified from the two libraries, strong or weak, there were no obvious sequence similarities.

By random mutagenesis and re-screening, one of the first-generation hit sequences we was optimized, and now improves the survival of FL5.12 cells 3- to 4-fold upon IL3 withdrawal. An analysis of the optimized sequence showed that the potency was improved in part by the introduction of a mismatch between the two halves of the stem, leading to a structure more closely resembling the structure of endogenous miRNAs. We hypothesized that the introduction of mismatches between the two halves of the stem-encoding sequences in the second-generation library would improve the potency of initial hit sequences, as well as the efficiency of retrieval by PCR, thereby expanding the range of feasible phenotypic screens.

Consistent with the first hypothesis, the introduction of mismatches between the two halves of the stem-encoding sequences significantly improved the potency of initial hit sequences when compared with the first-generation library in the same screen: Whereas initial hit sequences from the first-generation library doubled survival of FL5.12 cells after IL3 withdrawal, initial hit sequences from the second-generation library quadrupled and quintupled survival relative to a random control clone. Consistent with the second hypothesis, retrieval of hit sequences was apparently more efficient: Whereas ~70% of the second-generation library sequences have mismatches, all of the sequences retrieved at the end of the screen had mismatches. In addition, the sequencing of clones without mismatches often stalls part way through the 29-nucleotide stem (presumably due to the hairpin-loop structure); reading through the entire 29-nucleotide stem was successful at a noticeably higher frequency in sequencing clones with mismatches.

The random-mutagenesis methodology for creating mismatches is not perfectly random since each specific template molecule will be mutated at only one of four bases, depending on whether that specific template molecule ends up in the tube lacking A, C, T, or G. In addition, even if two identical template molecules ended up in the same tube, the first instance of a base whose complementary dNTP is missing is likely mutated at a different frequency than that of the second instance of the same base. Fortunately, the infidelity of the M-MuLV reverse transcriptase was greater than was expected, and more types of mutations (including deletions) were introduced than were predicted theoretically. T-G mismatches were most common (despite the fact the least amount of T in the reaction lacking C was used), likely due to the fact that G and U can form a wobble base pair in RNA and T possesses the same G-pairing —NH and =O groups as U possesses. Refinements can be made by adjusting the ratios of different dNTPs.

Advantages of the random shRNA approach include that it is unbiased with respect to mechanism(s) of action, of which the understanding remains incomplete, and that it leverages the capacity of small RNAs to alter the expression of many genes simultaneously. Using sequence homologies, existing miRNA target-identification algorithms provide hundreds of putative targets for hit shRNAs from the random library, but it is unclear whether, or how much, each putative target contributes to the phenotype, and it is unclear how much of the phenotype is even associated with canonical RNAi.

Among the hit shRNAs identified, none show any discernable sequence homologies, either overall or in the seed sequences (assuming canonical RNAi). The approach is functional in that it allow the cells to identify which sequences are most effective, and least toxic, without prior assumptions.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of generating a set or library of recombinant expression vectors, wherein said set or library of recombinant expression vectors is capable of expressing a set or library of short hairpin ribonucleic acid (shRNA) molecules, said method comprising the steps of:
   a. providing a nucleic acid intermediate I, wherein said single-stranded nucleic acid intermediate I comprises:
      (i) a first constant region;
      (ii) a variable region consisting of a sequence, wherein said sequence is either (I) substantially random; or (II) comprises a first sub-region and a second sub-region, wherein said first sub-region is substantially random and said second sub-region has a first sequence common to said set or library of shRNA molecules; and
      (iii) a second constant region;
   b. annealing a first primer to said second constant region of said single-stranded nucleic acid intermediate I;
   c. obtaining double-stranded intermediates I B for each of the four nucleotides (A, C, T and G) by extending said primer hybridized to nucleic acid intermediate I with the following polymerization reaction:
  (i) using a high-fidelity polymerase to extend said first primer in the absence of one of the four nucleotides;
  (ii) using a low-fidelity polymerase to continue the polymerization reaction in the absence of one of the four nucleotides;
  (iii) using a high-fidelity polymerase to continue the polymerization reaction in the presence of all four nucleotides;

thereby obtaining double-stranded intermediates I B from said single-stranded nucleic acid intermediate I, said double-stranded intermediate I B comprising said single-stranded nucleic acid intermediate I and an additional single-stranded nucleic acid molecule, wherein said additional single-stranded nucleic acid molecule hybridizes with said single-stranded nucleic acid intermediate I;

d. obtaining nucleic acid intermediates II from said double-stranded intermediates I B, and wherein said nucleic acid intermediates II comprise:
  (i) said single-stranded nucleic acid intermediate I;
  (ii) an intervening region; and
  (iii) a region that hybridizes with said single-stranded nucleic acid intermediate I;

e. obtaining double-stranded intermediates III from nucleic acid intermediates II, comprising said nucleic acid intermediate II and an additional nucleic acid molecule that hybridizes with said nucleic acid intermediate II, and wherein said double-stranded intermediates III comprise:
  (i) a first, double-stranded copy of said first constant region or a fragment thereof;
  (ii) a first, double-stranded copy of said variable region;
  (iii) a first, double-stranded copy of said second constant region;
  (iv) a double-stranded copy of said intervening region;
  (v) a second, inverted double-stranded copy of said second constant region;
  (vi) a second, inverted double-stranded copy of said variable region; and
  (vii) a second, inverted double-stranded copy of said first constant region or a fragment thereof;

wherein when said first, double-stranded copy of said variable region and said second, inverted double-stranded copy of said variable region from one strand of double-stranded intermediates III are hybridized a region of double-stranded secondary structure is formed where at least 10% contain at least one mismatched basepair; and wherein said first, double-stranded copy of said second constant region and said second, inverted double-stranded copy of said second constant region have a restriction enzyme site asymmetry, such that
  (A) said first, double-stranded copy of said second constant region, but not said second, inverted double-stranded copy of said second constant region, is a substrate for a first restriction enzyme, and;
  (B) said second, inverted, double-stranded copy of said second constant region, but not said first double-stranded copy of said second constant region, is a substrate for a second restriction enzyme;

thereby generating a set or library of recombinant expression vectors, wherein said set or library of recombinant expression vectors is capable of expressing a set or library of shRNA molecules.

2. The method of claim 1, wherein said variable region is 8-29 nucleotides long.

3. The method of claim 1, wherein said first sub-region is 8-29 nucleotides long.

4. The method of claim 1, wherein said first constant region, when in double-stranded form, is a substrate for a nicking endonuclease.

5. The method of claim 4, wherein the step of obtaining said double-stranded intermediates III comprise the steps of contacting said nucleic acid intermediate II with said nicking endonuclease, thereby generating a 3' end suitable for use as a second primer; and copying the un-nicked strand of said nucleic acid intermediate II with a DNA polymerase that uses said 3' end as said second primer.

6. The method of claim 5, wherein said DNA polymerase is a strand-displacing DNA polymerase.

7. The method of claim 1, wherein the step of obtaining said double-stranded intermediates III comprise the steps of (a) annealing a second primer to said nucleic acid intermediate II and (b) extending said second primer.

8. The method of claim 7, wherein said second primer contains a mismatched residue with respect to said nucleic acid intermediates II.

9. The method of claim 8, wherein said mismatched residue creates an additional restriction enzyme site asymmetry in said double-stranded intermediates III, such that a restriction enzyme digests one but not the other of: (a) said first, double-stranded copy of said first constant region or fragment thereof; and (b) said second, inverted double-stranded copy of said first constant region or fragment thereof.

10. The method of claim 7, wherein said step of extending said second primer is performed with a strand-displacing polymerase.

11. The method of claim 1, wherein said restriction enzyme site asymmetry is generated by either:
  a. incorporating a mismatched residue between said single-stranded nucleic acid intermediate I and said region that hybridizes with said single-stranded nucleic acid intermediate I, wherein, in said double-stranded intermediates III, said first, double-stranded copy of said second constant region has a different sequence from said second, inverted double-stranded copy of said second constant region;
  b. incorporating a residue with an altered backbone or base composition in said single-stranded nucleic acid intermediate I or said region that hybridizes with said single-stranded nucleic acid intermediate I; or
  c. a combination of (a) and (b).

12. The method of claim 1, wherein said double-stranded intermediates III have an additional restriction enzyme site asymmetry, such that either:
  (a) said first, double-stranded copy of said first constant region or fragment thereof, but not said second, inverted, double-stranded copy of said first constant region or fragment thereof, is a substrate for a third restriction enzyme; or
  (b) said second, inverted, double-stranded copy of said first constant region or fragment thereof, but not said first, double-stranded copy of said first constant region or fragment thereof, is a substrate for a third restriction enzyme;

said method further comprising the step of contacting said double-stranded intermediate III with said third restriction enzyme.

13. The method of claim 12, wherein said additional restriction enzyme site asymmetry is generated by either:
  a. incorporating a mismatched residue between said single-stranded nucleic acid intermediate I and said region that hybridizes with said single-stranded nucleic acid intermediate I, wherein, in said double-stranded intermediate III, said first, double-stranded copy of said first constant region or fragment thereof has a different sequence from said second, inverted double-stranded copy of said first constant region or fragment thereof;

b. incorporating a residue with an altered backbone or base composition in said single-stranded nucleic acid intermediate I or said region that hybridizes with said single-stranded nucleic acid intermediate I; or c. a combination of (a) and (b).

14. The method of claim 1, wherein step (c) is repeated four times prior to step (d), once for each of the four nucleotides and the four sets of products are pooled prior to step (d).

15. The method of claim 1, wherein all the steps of the method are repeated four times, once each of the four nucleotides and the four sets of products are pooled afterwards.

16. The method of claim 1, wherein said first primer contains a mismatched residue with respect to said second constant region.

17. The method of claim 1, wherein said step of obtaining said nucleic acid intermediates II from said double-stranded intermediates I B comprise ligating a linker nucleic acid molecule to the 3' end of said single-stranded nucleic acid intermediate I and the 5' end of said additional single-stranded nucleic acid molecule.

18. The method of claim 17, wherein said linker nucleic acid molecule is hairpin-shaped.

19. The method of claim 1, further comprising the step of obtaining circular intermediates IV from said double-stranded intermediates III, said circular intermediates IV comprising an expression vector backbone and, as an insert, either:

a. said double-stranded intermediates III; or b. a fragment of said double-stranded intermediates III, wherein said fragment comprises said first, double-stranded copy of said variable region and said second, inverted double-stranded copy of said variable region.

20. The method of claim 19, further comprising the step of digesting said circular intermediates IV with said first restriction enzyme and said second restriction enzyme, thereby generating linear intermediates V.

21. The method of claim 20, further comprising the step of intra-molecularly ligating said linear intermediates V, thereby generating circular products VI.

22. The method of claim 1, wherein individual recombinant expression vectors of said set or library of recombinant expression vectors comprise a gene encodes said shRNA molecule and contains a transcription termination site.

23. The method of claim 1, wherein individual recombinant expression vectors of said set or library of recombinant expression vectors comprise a promoter of an RNA polymerase.

24. The method of claim 1, wherein said set or library of said recombinant expression vectors is a set or library of recombinant viruses.

25. The method of claim 1, further comprising the step of contacting said set or library of said expression vectors with an RNA polymerase, thereby generating a set or library of said shRNA molecules.

26. A set or library of recombinant expression vectors generated by the method of claim 1.

27. The set or library of recombinant expression vectors of claim 26, wherein said set or library of recombinant expression vectors is a set or library of recombinant viruses.

28. A set or library of recombinant expression vectors, wherein said set or library of recombinant expression vectors expresses a set or library of short hairpin ribonucleic acid (shRNA) molecules, each shRNA molecule comprises contiguously:

(a) a variable region consisting of a sequence, wherein said sequence is either (I) substantially random; or (II) comprises a first sub-region and a second sub-region, wherein said first sub-region is substantially random and said second sub-region has a first sequence common to said set or library of shRNA molecules;

(b) a non self-complementary region consisting of a second sequence common to said library; and (c) a complementary region consisting of a sequence, wherein said sequence is the reverse complement of the variable region except for containing at least one mismatch in at least 10% of the shRNA molecules.

\* \* \* \* \*

```
                              SEQUENCE LISTING

<160> NUMBER OF SEQ ID NOS: 168

<210> SEQ ID NO 1
<211> LENGTH: 29
<212> TYPE: DNA
<213> ORGANISM: Artificial Sequence
<220> FEATURE:
<223> OTHER INFORMATION: Chemically synthesized

<400> SEQUENCE: 1
gggtagctac atttgcatat gtggatatg                                        29

<210> SEQ ID NO 2
<211> LENGTH: 29
<212> TYPE: DNA
<213> ORGANISM: Artificial Sequence
<220> FEATURE:
<223> OTHER INFORMATION: Chemically synthesized

<400> SEQUENCE: 2
gtggatcagt gtgttatagc tcgggcagg                                        29

<210> SEQ ID NO 3
<211> LENGTH: 19
<212> TYPE: DNA
<213> ORGANISM: Artificial Sequence
<220> FEATURE:
<223> OTHER INFORMATION: Chemically synthesized

<400> SEQUENCE: 3
acctcccgta ggtgatgca                                                   19

<210> SEQ ID NO 4
<211> LENGTH: 15
<212> TYPE: DNA
<213> ORGANISM: Artificial Sequence
<220> FEATURE:
<223> OTHER INFORMATION: Chemically synthesized

<400> SEQUENCE: 4
tcacctgcgg gagct                                                       15

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5
acctcccgta ggtgatgcag                                                  20

<210> SEQ ID NO 6
<211> LENGTH: 20
<212> TYPE: DNA
<213> ORGANISM: Artificial Sequence
<220> FEATURE:
<223> OTHER INFORMATION: Chemically synthesized

<400> SEQUENCE: 6
```

-continued ctgcatcacc tgcgggagct                                               20

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized

<400> SEQUENCE: 7
ctgcatcacc tacgggaggt                                               20

<210> SEQ ID NO 8
<211> LENGTH: 19
<212> TYPE: DNA
<213> ORGANISM: Artificial Sequence
<220> FEATURE:
<223> OTHER INFORMATION: Chemically synthesized

<400> SEQUENCE: 8
agctcccgca ggtgatgca                                                19

<210> SEQ ID NO 9
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (21)..(21)
<223> OTHER INFORMATION: n is a, c, g, or t

<400> SEQUENCE: 9
ctgcatcacc tgcgggagct n                                             21

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: n is a, c, g, or t

<400> SEQUENCE: 10
nagctcccgc aggtgatgca                                               20

<210> SEQ ID NO 11
<211> LENGTH: 10
<212> TYPE: DNA
<213> ORGANISM: Artificial Sequence
<220> FEATURE:
<223> OTHER INFORMATION: Chemically synthesized

<400> SEQUENCE: 11
acctcccgct                                                          10

<210> SEQ ID NO 12
<211> LENGTH: 10
<212> TYPE: DNA
<213> ORGANISM: Artificial Sequence
<220> FEATURE:
<223> OTHER INFORMATION: Chemically synthesized

<400> SEQUENCE: 12
agcgggaggt                                                             10

<210> SEQ ID NO 13
<211> LENGTH: 73
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (27)..(54)
<220> FEATURE:
<221> NAME/KEY: misc_feature
<222> LOCATION: (27)..(54)
<223> OTHER INFORMATION: n is a, c, g, or t

<400> SEQUENCE: 13
tctccgtaga gcgatgacct gaaaaannnn nnnnnnnnnn nnnnnnnnnn nnnnggttta    60
aacaggtggt cga                                                      73

<210> SEQ ID NO 14
<211> LENGTH: 15
<212> TYPE: DNA
<213> ORGANISM: Artificial Sequence
<220> FEATURE:
<223> OTHER INFORMATION: Chemically synthesized

<400> SEQUENCE: 14
ccacctgctt aaagc                                                    15

<210> SEQ ID NO 15
<211> LENGTH: 80
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (27)..(54)
<223> OTHER INFORMATION: n is a, c, g, or t

<400> SEQUENCE: 15
tctccgtaga gcgatgacct gaaaaannnn nnnnnnnnnn nnnnnnnnnn nnnnttttc    60 aggtcatcgc tctacggaga                                               80

<210> SEQ ID NO 16
<211> LENGTH: 44
<212> TYPE: DNA
<213> ORGANISM: Artificial Sequence
<220> FEATURE:
<223> OTHER INFORMATION: Chemically synthesized

<400> SEQUENCE: 16
ggaagcatgc cgcagcttca gtcagctgcg gcatgcttcc tcga                    44

<210> SEQ ID NO 17
<211> LENGTH: 186
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (27)..(54)
<223> OTHER INFORMATION: n is a, c, g, or t
<220> FEATURE:
<221> NAME/KEY: misc_feature -continued

```
<222> LOCATION: (133)..(160)
<223> OTHER INFORMATION: n is a, c, g, or t

<400> SEQUENCE: 17
tctccgtaga gcgatgacct gaaaaannnn nnnnnnnnnn nnnnnnnnnn nnnnggttta     60
aacaggtggt cgaggaagca tgccgcagct tcagtcagct gcggcatgct tcctcgacca    120
cctgcttaaa gcnnnnnnnn nnnnnnnnnn nnnnnnnnnn tttttcaggt catcgctcta    180
cggaga                                                                186

<210> SEQ ID NO 18
<211> LENGTH: 55
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (27)..(54)
<223> OTHER INFORMATION: n is a, c, g, or t

<400> SEQUENCE: 18
tctccgtaga gcgatgacct gaaaaannnn nnnnnnnnnn nnnnnnnnnn nnnng          55

<210> SEQ ID NO 19
<211> LENGTH: 55
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 19
cnnnnnnnnn nnnnnnnnnn nnnnnnnnnt ttttcaggtc atcgctctac ggaga          55

<210> SEQ ID NO 20
<211> LENGTH: 18
<212> TYPE: DNA
<213> ORGANISM: Artificial Sequence
<220> FEATURE:
<223> OTHER INFORMATION: Chemically synthesized

<400> SEQUENCE: 20
ccgtagaccg atgacctg                                                   18

<210> SEQ ID NO 21
<211> LENGTH: 52
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (24)..(51)
<223> OTHER INFORMATION: n is a, c, g, or t

<400> SEQUENCE: 21
ccgtagaccg atgacctgaa aaannnnnnn nnnnnnnnnn nnnnnnnnnn ng              52

<210> SEQ ID NO 22
<211> LENGTH: 55
<212> TYPE: DNA
<213> ORGANISM: Artificial Sequence
<220> FEATURE:
```

<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 22
cnnnnnnnnn nnnnnnnnnn nnnnnnnnnt ttttcaggtc atcgcactac ggaga         55

<210> SEQ ID NO 23
<211> LENGTH: 52
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (24)..(51)
<223> OTHER INFORMATION: n is a, c, g, or t

<400> SEQUENCE: 23
ccgtagaccg atgacctgaa aaannnnnnn nnnnnnnnnn nnnnnnnnnn ng              52

<210> SEQ ID NO 24
<211> LENGTH: 37
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (9)..(36)
<223> OTHER INFORMATION: n is a, c, g, or t

<400> SEQUENCE: 24
ccagctttnn nnnnnnnnn nnnnnnnnnn nnnnnng                              37

<210> SEQ ID NO 25
<211> LENGTH: 60
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 25
cnnnnnnnnn nnnnnnnnnn nnnnnnnnnt ttttcaggtc atcgctctac ggagatggcc    60

<210> SEQ ID NO 26
<211> LENGTH: 60
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (32)..(59)
<223> OTHER INFORMATION: n is a, c, g, or t

<400> SEQUENCE: 26
ggccatctcc gtagaccgat gacctgaaaa annnnnnnnn nnnnnnnnnn nnnnnnnnng    60

<210> SEQ ID NO 27
<211> LENGTH: 37
<212> TYPE: DNA
<213> ORGANISM: Artificial Sequence

```
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 27
cnnnnnnnnn nnnnnnnnnn nnnnnnnnna aagctgg                            37

<210> SEQ ID NO 28
<211> LENGTH: 134
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(28)
<223> OTHER INFORMATION: n is a, c, g, or t
<220> FEATURE:
<221> NAME/KEY: misc_feature
<222> LOCATION: (107)..(134)
<223> OTHER INFORMATION: n is a, c, g, or t

<400> SEQUENCE: 28
nnnnnnnnnn nnnnnnnnnn nnnnnnnngg tttaaacagg tggtcgagga agcatgccgc    60
agcttcagtc agctgcggca tgcttcctcg accacctgct taaagcnnnn nnnnnnnnnn   120
nnnnnnnnnn nnnn                                                    134

<210> SEQ ID NO 29
<211> LENGTH: 134
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(28)
<223> OTHER INFORMATION: n is a, c, g, or t
<220> FEATURE:
<221> NAME/KEY: misc_feature
<222> LOCATION: (107)..(134)
<223> OTHER INFORMATION: n is a, c, g, or t

<400> SEQUENCE: 29
nnnnnnnnnn nnnnnnnnnn nnnnnnnngc tttaagcagg aggacgagga agcatgccgc    60
agctgactga agctgcggca tgcttcctcg accacctgtt taaaccnnnn nnnnnnnnnn   120
nnnnnnnnnn nnnn                                                    134

<210> SEQ ID NO 30
<211> LENGTH: 33
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(28)
<223> OTHER INFORMATION: n is a, c, g, or t

<400> SEQUENCE: 30
nnnnnnnnnn nnnnnnnnnn nnnnnnnngg ttt                                33

<210> SEQ ID NO 31
<211> LENGTH: 33
<212> TYPE: DNA
```

```
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (6)..(33)
<223> OTHER INFORMATION: n is a, c, g, or t

<400> SEQUENCE: 31
aaaccnnnnn nnnnnnnnnn nnnnnnnnnn nnn                           33

<210> SEQ ID NO 32
<211> LENGTH: 103
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (9)..(36)
<223> OTHER INFORMATION: n is a, c, g, or t
<220> FEATURE:
<221> NAME/KEY: misc_feature
<222> LOCATION: (45)..(72)
<223> OTHER INFORMATION: n is a, c, g, or t

<400> SEQUENCE: 32
ccagctttnn nnnnnnnnnn nnnnnnnnnn nnnnnnggtt tagcnnnnnn nnnnnnnnnn    60
nnnnnnnnnn nnttttcag gtcatctcac tacggagatg gcc                      103

<210> SEQ ID NO 33
<211> LENGTH: 103
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (32)..(59)
<223> OTHER INFORMATION: n is a, c, g, or t
<220> FEATURE:
<221> NAME/KEY: misc_feature
<222> LOCATION: (68)..(95)
<223> OTHER INFORMATION: n is a, c, g, or t

<400> SEQUENCE: 33
ggccatctcc gtagtgagat gacctgaaaa annnnnnnnn nnnnnnnnnn nnnnnnnng    60 ctaaaccnnn nnnnnnnnnn nnnnnnnnnn nnnnnaaagc tgg                    103

<210> SEQ ID NO 34
<211> LENGTH: 96
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (47)..(51)
<223> OTHER INFORMATION: n is a, c, g, or t
<220> FEATURE:
<221> NAME/KEY: misc_feature
<222> LOCATION: (52)..(77)
<223> OTHER INFORMATION: n is a, c, g, or t

<400> SEQUENCE: 34
cccttatgca tgctgaggaa gaattcagcg gccgcgatga cctgaaaaan nnnnnnnnn    60 nnnnnnnnnn nnnnnnnggt ttaaacaggt ggtcga                            96
```

```
<210> SEQ ID NO 35
<211> LENGTH: 92
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (16)..(43)
<223> OTHER INFORMATION: n is a, c, g, or t

<400> SEQUENCE: 35
ccacctgctt aaagcnnnnn nnnnnnnnnn nnnnnnnnnn nnnttttttca ggtcatcgcg      60 gccgctgaat tcttcctcag catgcataag gg                                    92

<210> SEQ ID NO 36
<211> LENGTH: 44
<212> TYPE: DNA
<213> ORGANISM: Artificial Sequence
<220> FEATURE:
<223> OTHER INFORMATION: Chemically synthesized

<400> SEQUENCE: 36
ggaagcatga attctattca gtcatagaat tcatgcttcc tcga                       44

<210> SEQ ID NO 37
<211> LENGTH: 232
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (47)..(51)
<223> OTHER INFORMATION: phosphorothioate
<220> FEATURE:
<221> NAME/KEY: misc_feature
<222> LOCATION: (52)..(77)
<223> OTHER INFORMATION: n is a, c, g, or t
<220> FEATURE:
<221> NAME/KEY: misc_feature
<222> LOCATION: (156)..(183)
<223> OTHER INFORMATION: n is a, c, g, or t

<400> SEQUENCE: 37
cccttatgca tgctgaggaa gaattcagcg gccgcgatga cctgaaaaan nnnnnnnnn       60 nnnnnnnnnn nnnnnnnggt ttaaacaggt ggtcgaggaa gcatgaattc tattcagtca     120
tagaattcat gcttcctcga ccacctgctt aaagcnnnnn nnnnnnnnnn nnnnnnnnnn     180 nnnttttttca ggtcatcgcg gccgctgaat tcttcctcag catgcataag gg            232

<210> SEQ ID NO 38
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (17)..(44)
<223> OTHER INFORMATION: n is a, c, g, or t

<400> SEQUENCE: 38
gcgatgacct gaaaaannnn nnnnnnnn nnnnnnnnnn nnnng                        45

<210> SEQ ID NO 39
<211> LENGTH: 65
<212> TYPE: DNA
```

```
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 39
cnnnnnnnnn nnnnnnnnnn nnnnnnnnnt ttttcaggtc atcgcggccg ctgaattctt    60
cctca                                                                65

<210> SEQ ID NO 40
<211> LENGTH: 65
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (34)..(48)
<223> OTHER INFORMATION: phosphorothioate
<220> FEATURE:
<221> NAME/KEY: misc_feature
<222> LOCATION: (49)..(64)
<223> OTHER INFORMATION: n is a, c, g, or t

<400> SEQUENCE: 40
tgaggaagaa ttcagcggcc gcgatgacct gaaaaannnn nnnnnnnnn nnnnnnnnnn    60 nnnng                                                                65

<210> SEQ ID NO 41
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 41
cnnnnnnnnn nnnnnnnnnn nnnnnnnnnt ttttcaggtc atcgc                     45

<210> SEQ ID NO 42
<211> LENGTH: 65
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 42
cnnnnnnnnn nnnnnnnnnn nnnnnnnnnt ttttcaggtc atcgcggccg ctgaattctt    60
cctca                                                                65

<210> SEQ ID NO 43
<211> LENGTH: 65
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
```

<222> LOCATION: (37)..(64)
<223> OTHER INFORMATION: n is a, c, g, or t

<400> SEQUENCE: 43
tgaggaagaa ttcagcggcc gcgatgacct gaaaaannnn nnnnnnnnnn nnnnnnnnnn    60 nnnng                                                                65

<210> SEQ ID NO 44
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 44
cnnnnnnnnn nnnnnnnnnn nnnnnnnnnt ttttcaggtc atcgc                    45

<210> SEQ ID NO 45
<211> LENGTH: 49
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (21)..(49)
<223> OTHER INFORMATION: n is a, c, g, or t

<400> SEQUENCE: 45
ggccgcgatg acctgaaaaa nnnnnnnnnn nnnnnnnnnn nnnnnnnng               49

<210> SEQ ID NO 46
<211> LENGTH: 19
<212> TYPE: DNA
<213> ORGANISM: Artificial Sequence
<220> FEATURE:
<223> OTHER INFORMATION: Chemically synthesized

<400> SEQUENCE: 46
accacagatc tccggccgc                                                 19

<210> SEQ ID NO 47
<211> LENGTH: 15
<212> TYPE: DNA
<213> ORGANISM: Artificial Sequence
<220> FEATURE:
<223> OTHER INFORMATION: Chemically synthesized

<400> SEQUENCE: 47
gcggagatct gtggt                                                     15

<210> SEQ ID NO 48
<211> LENGTH: 42
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (14)..(41)
<223> OTHER INFORMATION: n is a, c, g, or t

<400> SEQUENCE: 48
accacagatc tccnnnnnnn nnnnnnnnnn nnnnnnnnnn ng                    42

<210> SEQ ID NO 49
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 49
cnnnnnnnnn nnnnnnnnnn nnnnnnnnnt ttttcaggtc atcgc                 45

<210> SEQ ID NO 50
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (23)..(50)
<223> OTHER INFORMATION: n is a, c, g, or t

<400> SEQUENCE: 50
gcggccgcga tgacctgaaa aannnnnnnn nnnnnnnnnn nnnnnnnnnn g          51

<210> SEQ ID NO 51
<211> LENGTH: 42
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(29)
<223> OTHER INFORMATION: n is a, c, g, or t

<400> SEQUENCE: 51
cnnnnnnnnn nnnnnnnnnn nnnnnnnnng gagatctgtg gt                    42

<210> SEQ ID NO 52
<211> LENGTH: 99
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (14)..(41)
<223> OTHER INFORMATION: n is a, c, g, or t
<220> FEATURE:
<221> NAME/KEY: misc_feature
<222> LOCATION: (50)..(77)
<223> OTHER INFORMATION: n is a, c, g, or t

<400> SEQUENCE: 52
accacagatc tccnnnnnnn nnnnnnnnnn nnnnnnnnn ngcttaaccn nnnnnnnnn    60 nnnnnnnnnn nnnnnnnttt ttcaggtcat cgcggccgc                        99

<210> SEQ ID NO 53
<211> LENGTH: 99
<212> TYPE: DNA
<213> ORGANISM: Artificial Sequence
<220> FEATURE:
<223> OTHER INFORMATION: Chemically synthesized

```
<220> FEATURE:
<221> NAME/KEY: misc_feature
<222> LOCATION: (23)..(50)
<223> OTHER INFORMATION: n is a, c, g, or t
<220> FEATURE:
<221> NAME/KEY: misc_feature
<222> LOCATION: (59)..(86)
<223> OTHER INFORMATION: n is a, c, g, or t

<400> SEQUENCE: 53
gcggccgcga tgacctgaaa aannnnnnnn nnnnnnnnnn nnnnnnnnnn ggttaagcnn      60
nnnnnnnnnn nnnnnnnnnn nnnnnnggag atctgtggt                            99

<210> SEQ ID NO 54
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 54
taagctagaa aacgcgtgcg gagccttagc taaac                                35

<210> SEQ ID NO 55
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 55
attcgatctt ttgcgcacgc ctcgggatc                                       29

<210> SEQ ID NO 56
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 56
tgtgtggaca gaaactggga gggttgcagc taaac                                35

<210> SEQ ID NO 57
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 57
acacacctgt ctttgaccct cccaacgtc                                       29

<210> SEQ ID NO 58
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 58
cctaacaatg atcttcattg tcttcgtggc taaac                                35

<210> SEQ ID NO 59
<211> LENGTH: 29
<212> TYPE: DNA
```

```
<213> ORGANISM: Artificial Sequence
<220> FEATURE:
<223> OTHER INFORMATION: Insert sequence of clone from library

<400> SEQUENCE: 59
ggattgttac tagaagtatc agaagcacc                                       29

<210> SEQ ID NO 60
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 60
ttagataatg gtttcaaaat gatttattgc taaac                                35

<210> SEQ ID NO 61
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 61
gatctgttac cgaagtttta ctaaataac                                       29

<210> SEQ ID NO 62
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 62
tgggagggat acaaataaca ctaccccgc taaac                                 35

<210> SEQ ID NO 63
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 63
accctcccca tgtctactgc gatcggggc                                       29

<210> SEQ ID NO 64
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 64
tggctcgtac ggacataagc aaggagtggc taaac                                35

<210> SEQ ID NO 65
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 65
accgagcatg cctgtattcg ttcctcacc                                       29
```

<210> SEQ ID NO 66
<211> LENGTH: 33
<212> TYPE: DNA
<213> ORGANISM: Artificial Sequence
<220> FEATURE:
<223> OTHER INFORMATION: Insert sequence of clone from library

<400> SEQUENCE: 66
tatcttgctt gtttattgtg tagaatgcta aac					33

<210> SEQ ID NO 67
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 67
gatagaacgg acgaatagca catcttac						28

<210> SEQ ID NO 68
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 68
tttgttgtga tctggcttaa tccgcttggc taaac					35

<210> SEQ ID NO 69
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 69
aaacaacact agaccgaatt aggcgaacc						29

<210> SEQ ID NO 70
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 70
tataccgtgg ggctctattt ggacctggct aaac					34

<210> SEQ ID NO 71
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 71
cgctcgtacg gtacagacgg aattggaac						29

<210> SEQ ID NO 72
<211> LENGTH: 34
<212> TYPE: DNA
<213> ORGANISM: Artificial Sequence
<220> FEATURE:

```
<223> OTHER INFORMATION: Insert sequence of clone from library

<400> SEQUENCE: 72
gccctcgaat aattgatatc tgttgatgct aaac                              34

<210> SEQ ID NO 73
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 73
ccgggagctg attaactatg gacaactac                                   29

<210> SEQ ID NO 74
<211> LENGTH: 33
<212> TYPE: DNA
<213> ORGANISM: Artificial Sequence
<220> FEATURE:
<223> OTHER INFORMATION: Insert sequence of clone from library

<400> SEQUENCE: 74
gccatggctt gcatacgcga gtgggagcta aac                              33

<210> SEQ ID NO 75
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 75
cggtaccgaa cgtatgcgcg caccctcgc                                   29

<210> SEQ ID NO 76
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 76
tatgtaggtt aatgtttggt ttggatgagc taaac                            35

<210> SEQ ID NO 77
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 77
gtacgtccaa ttgcaagcca agcctactc                                   29

<210> SEQ ID NO 78
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 78
ctacgttagg ttatccttgt tgtttggggc taaac                            35
```

```
<210> SEQ ID NO 79
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 79
gatgcaatct aataggaaca tcaaacccc                                        29

<210> SEQ ID NO 80
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 80
gaccggactt attgtctggt ccaaattcgc taaac                                 35

<210> SEQ ID NO 81
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 81
ctggcctgaa taacagacca cgtttaagc                                        29

<210> SEQ ID NO 82
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 82
tacatttact gccttactct atgctgcggc taaac                                 35

<210> SEQ ID NO 83
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 83
atgtaaatga cggaatgaga tacgacgcc                                        29

<210> SEQ ID NO 84
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 84
atagattgga caaaacttaa tcaaccctgc taaac                                 35

<210> SEQ ID NO 85
<211> LENGTH: 31
<212> TYPE: DNA
<213> ORGANISM: Artificial Sequence
<220> FEATURE:
<223> OTHER INFORMATION: Insert sequence of clone from library
```

```
<400> SEQUENCE: 85
cctagcttct tgcacgccac gtcactcctc c                               31

<210> SEQ ID NO 86
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 86
gctgatcata atgtgtaaaa tcctctagct aaac                            34

<210> SEQ ID NO 87
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 87
gcgactagta ttacacatct cggacatc                                   28

<210> SEQ ID NO 88
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 88
cctgcttttt attccgcgct ctggtgggct aaac                            34

<210> SEQ ID NO 89
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 89
ggacgaaaaa taaggcgcga gaccacagc                                  29

<210> SEQ ID NO 90
<211> LENGTH: 31
<212> TYPE: DNA
<213> ORGANISM: Artificial Sequence
<220> FEATURE:
<223> OTHER INFORMATION: Insert sequence of clone from library

<400> SEQUENCE: 90
gtcagggctg taaatagttt atagtggcaa a                               31

<210> SEQ ID NO 91
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 91
cagtcccgac agggtttatc aaagatcac                                  29

<210> SEQ ID NO 92
<211> LENGTH: 34
```

```
<212> TYPE: DNA
<213> ORGANISM: Artificial Sequence
<220> FEATURE:
<223> OTHER INFORMATION: Insert sequence of clone from library

<400> SEQUENCE: 92
tggctccaga aaccagcccc tccttatgct aaac                                   34

<210> SEQ ID NO 93
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 93
gaccgaggtc tttggtcgcc gaggaatac                                         29

<210> SEQ ID NO 94
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 94 cctgctttt attccgcgct ctggtgggct aaac                                    34

<210> SEQ ID NO 95
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 95
ggacgaaaaa taaggcgcga gaccacagc                                         29

<210> SEQ ID NO 96
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 96
taaaggcatc gatggagatt tcgcgaaggc taaac                                  35

<210> SEQ ID NO 97
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 97
atttccgtag ctacctctaa agcgcttcc                                         29

<210> SEQ ID NO 98
<211> LENGTH: 32
<212> TYPE: DNA
<213> ORGANISM: Artificial Sequence
<220> FEATURE:
<223> OTHER INFORMATION: Insert sequence of clone from library

<400> SEQUENCE: 98
```
tccacgggcc gctacagtcc cttatgctaa ac                                      32

<210> SEQ ID NO 99
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 99
aggtgtccgg cgatgtcagg gaatctac                                           28

<210> SEQ ID NO 100
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 100
tattttccgt gggtgccgaa tccgatatgc taaac                                   35

<210> SEQ ID NO 101
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 101
ataaaaggca cccacggctt aggctgtac                                          29

<210> SEQ ID NO 102
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 102
cattgatgag attggtggag ttatttttgc taaac                                   35

<210> SEQ ID NO 103
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 103
gtagctactc tagccacctc agtgaaaac                                          29

<210> SEQ ID NO 104
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 104
gtgtgctggg gctaatgcct cgccgggcgc taaac                                   35

<210> SEQ ID NO 105
<211> LENGTH: 29
<212> TYPE: DNA
<213> ORGANISM: Artificial Sequence

```
<220> FEATURE:
<223> OTHER INFORMATION: Insert sequence of clone from library

<400> SEQUENCE: 105
cacacgaccc tgattacggt gcggcccgc                                  29

<210> SEQ ID NO 106
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 106
tgaccacacc ttcatccctc atccctggct aaac                            34

<210> SEQ ID NO 107
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 107
cactggtgtg gaagtaggga gtagggacc                                  29

<210> SEQ ID NO 108
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 108
atattgggga aagctgggat ggactattgg taaac                           35

<210> SEQ ID NO 109
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 109
ttaagtccct ttcgaccta cctgataac                                   29

<210> SEQ ID NO 110
<211> LENGTH: 36
<212> TYPE: DNA
<213> ORGANISM: Artificial Sequence
<220> FEATURE:
<223> OTHER INFORMATION: Insert sequence of clone from library

<400> SEQUENCE: 110
tgccaggtta gagcgcaaaa gttcgaacgg ctaaac                          36

<210> SEQ ID NO 111
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 111
taggccaatc tcgcgttttc aagcttgc                                   28
```

<210> SEQ ID NO 112
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 112
cgtttgagtg gtgtggtagg tgtgttgggc taaac                              35

<210> SEQ ID NO 113
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 113
gcgagctcac cacgccatcc acgcaaccc                                     29

<210> SEQ ID NO 114
<211> LENGTH: 34
<212> TYPE: DNA
<213> ORGANISM: Artificial Sequence
<220> FEATURE:
<223> OTHER INFORMATION: insert sequence of clone from library

<400> SEQUENCE: 114
tacgttaggt tatccttgtt gtttggggct aaac                               34

<210> SEQ ID NO 115
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 115
gatgcaatct aataggaaca tcaaacccc                                     29

<210> SEQ ID NO 116
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 116
tcaatttacg gtcgtgctgt agagaaccgc taaac                              35

<210> SEQ ID NO 117
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 117
ggcccaaggc tccttccacc aaagattgc                                     29

<210> SEQ ID NO 118
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 118
ctgagtcaat gcgctattta aggaggatgc taaac                          35

<210> SEQ ID NO 119
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 119
gactcagtta cgcggtaagt tcctcctac                                 29

<210> SEQ ID NO 120
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 120
cagtagtcca gtgtaccact aagtgaagct aaac                           34

<210> SEQ ID NO 121
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 121
ggtcatcagg tcacatggtg gttcacttc                                 29

<210> SEQ ID NO 122
<211> LENGTH: 33
<212> TYPE: DNA
<213> ORGANISM: Artificial Sequence
<220> FEATURE:
<223> OTHER INFORMATION: Insert sequence of clone from library

<400> SEQUENCE: 122
cgagggaatc ggccactgtg ctggtcgcta aac                            33

<210> SEQ ID NO 123
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 123
gctcccttag ccggtgacac gaccagtgc                                 29

<210> SEQ ID NO 124
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 124
cggatcacca ggcgtttgag tcctagcgct aaac                           34

<210> SEQ ID NO 125

```
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 125
ggctagtggt ccgcaaactc aggatcgc                                         28

<210> SEQ ID NO 126
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 126
gcgtgccatc ttgttggata gaatttggct aaac                                  34

<210> SEQ ID NO 127
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 127
ccgcacggta ggacaaccta tcttagacc                                        29

<210> SEQ ID NO 128
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 128
gtcactcggg gtttctttct gtcttatagc taaac                                 35

<210> SEQ ID NO 129
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 129
cagtgagccc caaagaaaga cagactatc                                        29

<210> SEQ ID NO 130
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 130
acacacggcc tttgcacggt tggtagagct aaac                                  34

<210> SEQ ID NO 131
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 131
```
gtgtgtgccg aaacgtgcg gaccatctc                                   29

<210> SEQ ID NO 132
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 132
cggtagacct aggggagccg tcgatctagc taaac                           35

<210> SEQ ID NO 133
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 133
gccatctgga tccctcggc agctagatc                                   29

<210> SEQ ID NO 134
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 134
ttggtccatc attcgcgttc atgttggggc taaac                           35

<210> SEQ ID NO 135
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 135
aaccaggtag taagcgcaag tacaacgcc                                  29

<210> SEQ ID NO 136
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 136
tcagccatgc gtgcgttggg gcttgtacgc taaac                           35

<210> SEQ ID NO 137
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 137
agtcgggaca cacgcaaccc cgaacatgc                                  29

<210> SEQ ID NO 138
<211> LENGTH: 34
<212> TYPE: DNA

```
<213> ORGANISM: Artificial Sequence
<220> FEATURE:
<223> OTHER INFORMATION: Insert sequence of clone from library

<400> SEQUENCE: 138
ggtagaccta ggggagccgt cgatctagct aaac                           34

<210> SEQ ID NO 139
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 139
gccatctgga tcccctcggc agctagatc                                 29

<210> SEQ ID NO 140
<211> LENGTH: 36
<212> TYPE: DNA
<213> ORGANISM: Artificial Sequence
<220> FEATURE:
<223> OTHER INFORMATION: Insert sequence of clone from library

<400> SEQUENCE: 140
aaggcatggt ttgttcgact ttgccctctg gcaaac                         36

<210> SEQ ID NO 141
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 141
ttcgtaccaa actagctgaa tcgggagac                                 29

<210> SEQ ID NO 142
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 142
ggtttctgtc gcgtgctgtt atataatgct aaac                           34

<210> SEQ ID NO 143
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 143
ccaaagacag cgcacggcaa tatattac                                  28

<210> SEQ ID NO 144
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 144
cggtagacct aggggagccg tcgatctagc taaac                          35
```

<210> SEQ ID NO 145
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 145
gccatctgga tcccctcggc agctagatc                              29

<210> SEQ ID NO 146
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 146
taggagcgtt cggccttacg gtgttatggc taaac                       35

<210> SEQ ID NO 147
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 147
atcctcgcta gccggtttgc cacaatacc                              29

<210> SEQ ID NO 148
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 148
cacgggctga tcgtaagtga ctggtcagct aaac                        34

<210> SEQ ID NO 149
<211> LENGTH: 28
<212> TYPE: DNA
<213> ORGANISM: Artificial Sequence
<220> FEATURE:
<223> OTHER INFORMATION: Insert sequence of clone from library

<400> SEQUENCE: 149
gtgcccgact agcattcact gaccagtc                               28

<210> SEQ ID NO 150
<211> LENGTH: 34
<212> TYPE: DNA
<213> ORGANISM: Artificial Sequence
<220> FEATURE:
<223> OTHER INFORMATION: Insert sequence of clone from library

<400> SEQUENCE: 150
actatcaagg ggcttgtggg gacaagagct aaac                        34

<210> SEQ ID NO 151
<211> LENGTH: 28
<212> TYPE: DNA
<213> ORGANISM: Artificial Sequence
<220> FEATURE:

<223> OTHER INFORMATION: Insert sequence of clone from library

<400> SEQUENCE: 151
tgatagttcc ccgaacaccc ctgttctc                                              28

<210> SEQ ID NO 152
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 152
cgcgcatgga tgcccggtat ggatttacgc taaac                                      35

<210> SEQ ID NO 153
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 153
gcgcgtacct acgggccata cctaaatgc                                             29

<210> SEQ ID NO 154
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 154
gcattcaatg acccgtgtta ccagggtgc                                             29

<210> SEQ ID NO 155
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 155
tccgcagcta aatattccgt ctgccggtc                                             29

<210> SEQ ID NO 156
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 156
gtcttccaac tatgtactcg gtcccatac                                             29

<210> SEQ ID NO 157
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 157
cccatcgatg taaacgtata cacctatac                                             29

```
<210> SEQ ID NO 158
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 158
cacctagtca cacaatatcg agcccgtcc                                          29

<210> SEQ ID NO 159
<211> LENGTH: 132
<212> TYPE: DNA
<213> ORGANISM: Artificial Sequence
<220> FEATURE:
<223> OTHER INFORMATION: Insert sequence of clone from library
<220> FEATURE:
<221> NAME/KEY: misc_feature
<222> LOCATION: (51)..(78)
<223> OTHER INFORMATION: n is a, c, g, or t

<400> SEQUENCE: 159
ccctatatgc atgctgagga agaattcagc ggccgcgatg acctgaaaaa nnnnnnnnnn        60
nnnnnnnnnn nnnnnnnngg tttaaacagg tgagaattct attcagtcat agaattctca       120
cctgcttaaa gc                                                           132

<210> SEQ ID NO 160
<211> LENGTH: 19
<212> TYPE: DNA
<213> ORGANISM: Artificial Sequence
<220> FEATURE:
<223> OTHER INFORMATION: Insert sequence of clone from library

<400> SEQUENCE: 160
ccggaattga agatctggg                                                     19

<210> SEQ ID NO 161
<211> LENGTH: 32
<212> TYPE: DNA
<213> ORGANISM: Artificial Sequence
<220> FEATURE:
<223> OTHER INFORMATION: Insert sequence of clone from library

<400> SEQUENCE: 161
ccgtaattga ttactattaa taactagaat tc                                      32

<210> SEQ ID NO 162
<211> LENGTH: 36
<212> TYPE: DNA
<213> ORGANISM: Artificial Sequence
<220> FEATURE:
<223> OTHER INFORMATION: Insert sequence of clone from library

<400> SEQUENCE: 162
cgtaggttac tgggcacaat ggtcatacgg ctaaac                                  36

<210> SEQ ID NO 163
<211> LENGTH: 35
<212> TYPE: DNA
<213> ORGANISM: Artificial Sequence
<220> FEATURE:
```

```
<223> OTHER INFORMATION: Insert sequence of clone from library

<400> SEQUENCE: 163
aggcatcgat ttataaggca tacagccagc taaac                              35

<210> SEQ ID NO 164
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 164
tagaaggttg atatatgagt tagggtatgc taaac                              35

<210> SEQ ID NO 165
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 165
gggtagctac atttgcatat gtggatatgc taaac                              35

<210> SEQ ID NO 166
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 166
gtggatcagt gtgttatagc tcgggcaggc taaac                              35

<210> SEQ ID NO 167
<211> LENGTH: 35
<212> TYPE: DNA
<213> ORGANISM: Artificial Sequence
<220> FEATURE:
<223> OTHER INFORMATION: Insert sequence of clone from library

<400> SEQUENCE: 167
ggtagagggg atgtcaaact tgattgatgc taaac                              35

<210> SEQ ID NO 168
<211> LENGTH: 29
<212> TYPE: DNA
<213> ORGANISM: Artificial Sequence
<220> FEATURE:
<223> OTHER INFORMATION: Insert sequence of clone from library

<400> SEQUENCE: 168
ccatctcccc tacagtttga actaactac                                     29
```